(12) United States Patent
Suzuki et al.

(10) Patent No.: US 9,346,821 B2
(45) Date of Patent: *May 24, 2016

(54) HETEROCYCLIC CARBOXYLIC ACID ESTER DERIVATIVE

(71) Applicant: AJINOMOTO CO., INC., Tokyo (JP)

(72) Inventors: Tamotsu Suzuki, Kawasaki (JP); Takahiro Koshiba, Kawasaki (JP); Munetaka Tokumasu, Kawasaki (JP); Koji Ohsumi, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/098,774

(22) Filed: Dec. 6, 2013

(65) Prior Publication Data

US 2014/0094489 A1 Apr. 3, 2014

Related U.S. Application Data

(63) Continuation of application No. PCT/JP2012/064664, filed on Jun. 7, 2012.

(30) Foreign Application Priority Data

Jun. 7, 2011 (JP) ................................. 2011-127700

(51) Int. Cl.
| | | |
|---|---|---|
| C07D 495/04 | (2006.01) | |
| C07D 307/68 | (2006.01) | |
| C07D 333/38 | (2006.01) | |
| C07D 405/06 | (2006.01) | |
| C07D 409/06 | (2006.01) | |
| C07D 417/06 | (2006.01) | |
| A61K 38/00 | (2006.01) | |

(52) U.S. Cl.
CPC ............ *C07D 495/04* (2013.01); *C07D 307/68* (2013.01); *C07D 333/38* (2013.01); *C07D 405/06* (2013.01); *C07D 409/06* (2013.01); *C07D 417/06* (2013.01); *A61K 38/00* (2013.01)

(58) Field of Classification Search
CPC .. C07D 307/68; C07D 405/06; C07D 417/06; C07D 495/04; C07D 333/38; C07D 409/06; A61K 38/00
USPC ......... 514/301, 422, 471, 314, 448, 326, 365; 546/123, 114, 165; 548/517, 201, 527; 549/484, 71
See application file for complete search history.

(56) References Cited

U.S. PATENT DOCUMENTS

| | | | | |
|---|---|---|---|---|
| 4,563,527 | A * | 1/1986 | Fujii et al. ...................... | 546/169 |
| 5,532,267 | A * | 7/1996 | Nakayama ........... | C07D 407/12 514/467 |
| 6,358,960 | B1 | 3/2002 | Senokuchi et al. | |
| 8,609,715 | B2 | 12/2013 | Konishi et al. | |
| 8,877,805 | B2 * | 11/2014 | Konishi et al. ................. | 514/471 |
| 9,024,044 | B2 * | 5/2015 | Koshiba et al. ............... | 549/377 |
| 9,115,107 | B2 * | 8/2015 | Konishi ............... | C07D 277/20 |
| 2007/0298025 | A1 | 12/2007 | Harosh et al. | |
| 2008/0009537 | A1 | 1/2008 | Sakai | |
| 2010/0311690 | A1 | 12/2010 | Harosh et al. | |
| 2012/0283222 | A1 | 11/2012 | Konishi et al. | |
| 2013/0338132 | A1 | 12/2013 | Koshiba et al. | |
| 2015/0011511 | A1 * | 1/2015 | Konishi et al. .................. | 514/99 |
| 2015/0099733 | A1 * | 4/2015 | Koshiba et al. .......... | 514/210.18 |
| 2015/0313889 | A1 | 11/2015 | Konishi et al. | |

FOREIGN PATENT DOCUMENTS

| | | | |
|---|---|---|---|
| EP | 0071433 | * | 2/1983 |
| EP | 0 556 024 A1 | | 8/1993 |
| EP | 2 757 093 A1 | | 7/2014 |
| JP | 55-167275 A | | 12/1980 |
| JP | 59-5115 A | | 1/1984 |
| JP | 61-22075 A | | 1/1986 |

(Continued)

OTHER PUBLICATIONS

Dorwald; "Side Reactions in Organic Synthesis: A Guide to Successful Synthesis Design" 2005 Wiley-VCH Verlag GmbH & Co. KGaA, Wienheim, Chapter 1, pp. 1-16.*
U.S. Appl. No. 14/089,040, filed Nov. 25, 2013, Konishi, et al.
International Search Report issued Jul. 17, 2012 in PCT/JP2012/064664.

*Primary Examiner* — Janet L Andres
*Assistant Examiner* — Daniel Carcanague
(74) *Attorney, Agent, or Firm* — Oblon, McClelland, Maier & Neustadt, L.L.P.

(57) ABSTRACT

The present invention provides a blood glucose elevation inhibitor having a serine protease inhibitory action, which is a novel therapeutic or prophylactic agent for obesity. A compound represented by the following formula (I)

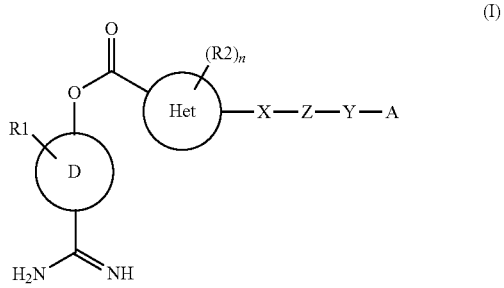

wherein each symbol is as described in the specification, or a pharmaceutically acceptable salt thereof.

21 Claims, No Drawings

(56) References Cited

FOREIGN PATENT DOCUMENTS

| | | |
|---|---|---|
| JP | 5-213927 A | 8/1993 |
| WO | WO 99/41231 A1 | 8/1999 |
| WO | WO 2006/050999 A2 | 5/2006 |
| WO | WO 2006/057152 A1 | 6/2006 |
| WO | WO 2009/071601 A1 | 6/2009 |
| WO | WO 2011/071048 A1 | 6/2011 |
| WO | WO 2013/039187 A1 | 3/2013 |
| WO | WO 2013/187533 A1 | 12/2013 |

\* cited by examiner

HETEROCYCLIC CARBOXYLIC ACID ESTER DERIVATIVE

CROSS REFERENCES TO RELATED APPLICATIONS

This application is a Continuation of International Patent Application No. PCT/JP2012/064664, filed on Jun. 7, 2012, and claims priority to Japanese Patent Application No. 2011-127700, filed on Jun. 7, 2011.

BACKGROUND OF THE INVENTION

1. Field of the Invention

The present invention relates to novel heterocyclic carboxylic acid ester derivatives having a serine protease (particularly trypsin and enteropeptidase) inhibitory activity. The present invention also relates to pharmaceutical compositions which contain such a heterocyclic carboxylic acid ester derivative and drugs for the prophylaxis or treatment of diabetes.

2. Discussion of the Background

At present, insulin secretagogues (sulfonylureas), glucose absorption inhibitors (α-glucosidase inhibitors), insulin sensitizers (biguanide, thiazolidine derivatives), and the like are clinically used as therapeutic drugs for diabetes. However, since all of them are accompanied by side effects such as hypoglycemia, diarrhea, lactic acidosis, edema, and the like, show an insufficient effect, and the like, a medicament satisfying clinical needs is still demanded.

In recent years, a benzoic acid ester having a protease inhibitory activity, which is represented by the following compound, has been reported to show a blood glucose elevation suppressing action in diabetes animal model (patent document 1). The following compound is considered to show an enzyme inhibitory activity on trypsin, thrombin, pancreatic, and plasma kallikreins, plasmin and the like and a leukotriene receptor antagonistic action. Moreover, an enteropeptidase inhibitory activity of the following compound has also been reported (non-patent document 1). However, many unclear points remain in the relationship between such actions and a blood glucose elevation suppressing action.

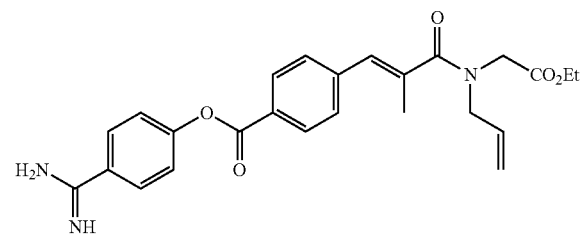 [SMILES: C=CCN(CC(=O)OCC)C(=O)/C(C)=C/c1ccc(C(=O)Oc2ccc(C(=N)N)cc2)cc1]

On the other hand, as for a heterocyclic carboxylic acid ester structure, patent document 2 discloses a compound as a therapeutic drug for pancreatitis. In this document, only heterocyclic carboxylic acid ester compounds wherein the substituent of the heterocyclic carboxylic acid moiety is a methyl group or a methoxy group or unsubstituted compounds are disclosed, as represented by the following formula. While these compounds are disclosed as showing an inhibitory activity on trypsin, chymotrypsin and thrombin, no description is given as to the enteropeptidase inhibitory activity and blood glucose elevation suppressing action.

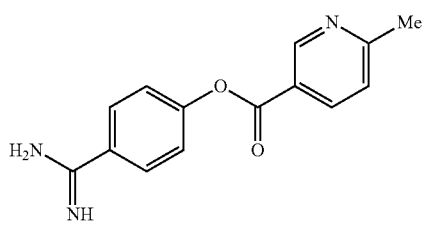 [SMILES: Cc1ccc(C(=O)Oc2ccc(C(=N)N)cc2)cn1]

In addition, non-patent document 2 also describes a heterocyclic carboxylic acid ester having a protease inhibitory activity, which is represented by the following formula. However, only compounds wherein the heterocyclic moiety is unsubstituted are disclosed, and no description is given as to the enteropeptidase inhibitory activity and blood glucose elevation suppressing action of these compounds.

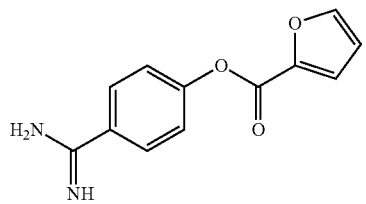 [SMILES: N=C(N)c1ccc(OC(=O)c2ccco2)cc1]

Furthermore, patent document 3 describes a compound represented by the following formula. However, it has a structure wherein an aryl group is directly bonded to the heterocyclic moiety, which is completely different from the compound of the present invention. The document discloses an inhibitory activity against blood coagulation factor VIIa; however, no description is given as to the enteropeptidase inhibitory activity and blood glucose elevation suppressing action.

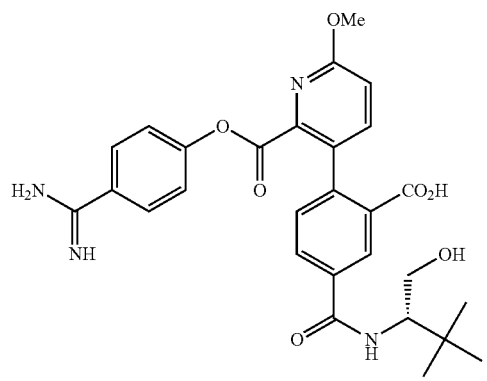 [SMILES: COc1ccc(-c2ccc(C(=O)N[C@H](CO)C(C)(C)C)cc2C(=O)O)c(C(=O)Oc2ccc(C(=N)N)cc2)n1]

On the other hand, trypsin is one of the intestinal serine proteases and is produced by degradation of inactive trypsinogen by enteropeptidase. Trypsin is known to activate various digestive enzymes by acting on chymotrypsinogen, proelastase, procarboxylesterase, procolipase and pro-sucrase-isomaltase, and the like. Therefore, it is considered that an inhibitor of enteropeptidase and trypsin lowers the digestive capacity for protein, lipid, and carbohydrates, and is effective as a drug for the prophylaxis or treatment of obesity and hyperlipidemia.

Patent document 4 describes that a medicament that inhibits both enteropeptidase and trypsin is interesting as a body fat-reducing agent. In addition, patent document 5 reports a compound having an inhibitory activity against enteropeptidase, trypsin, plasmin, kallikrein, and the like as an antiobesity drug. However, neither of these publications describe suppression of blood glucose elevation and hypoglycemic effect afforded by simultaneous inhibition of enteropeptidase and trypsin, and the protease inhibitor described therein has a structure completely different from that of the compound of the present invention.

DOCUMENT LIST

Patent Documents patent document 1: WO2006/057152
patent document 2: JP-A-55-167275,
patent document 3: WO99/41231
patent document 4: WO2006/050999
patent document 5: WO2009/071601

Non-Patent Documents non-patent document 1: Biomedical Research (2001), 22(5) 257-260
non-patent document 2: Advances in Experimental Medicine and Biology (1989), 247B (Kinins 5, Pt. B), 271-6

SUMMARY OF THE INVENTION

Therefore, to further satisfy the clinical needs from the aspects of effect, safety and the like, a hyperglycemic inhibitor having a serine protease inhibitory action, which is a new drug for the prophylaxis or treatment of diabetes, is desired.

The present invention aims to provide a heterocyclic carboxylic acid ester derivative, which is a novel compound having a serine protease inhibitory action.

The present invention also aims to provide a serine protease (particularly trypsin and enteropeptidase) inhibitor.

The present invention also aims to provide novel hyperglycemic inhibitors or hypoglycemic agents, and further, drug for the prophylaxis and/or treatment of any of diabetes, obesity, hyperlipidemia, diabetic complication, and metabolic syndrome.

In view of the above-mentioned current situation, the present inventors have conducted intensive studies and considered that simultaneous inhibition of trypsin and enteropeptidase is particularly effective for the suppression of blood glucose elevation. They have synthesized various heterocyclic carboxylic acid ester derivatives, which are novel compounds, evaluated trypsin and enteropeptidase inhibitory activity, and found that certain heterocyclic carboxylic acid ester derivatives are protease inhibitors that simultaneously inhibit them, which resulted in the completion of the present invention. Furthermore, they have also found that such representative compounds show a blood glucose elevation suppressing effect in diabetes animal model.

Accordingly, the present invention provides a heterocyclic carboxylic acid ester derivative represented by the following formula (I) or a pharmaceutically acceptable salt thereof (hereinafter sometimes to be simply referred to as "the compound of the present invention"), pharmaceutical composition containing the same, and a serine protease inhibitor containing the same as an active ingredient.

The present invention relates to the following.
[1] A compound represented by the following formula (I), or a pharmaceutically acceptable salt thereof:

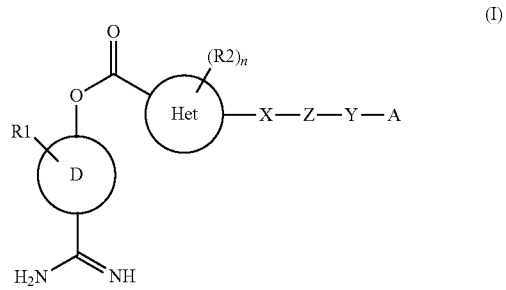

wherein
D is a benzene ring, a naphthalene ring or a pyridine ring,
Het is a hetero ring,
R1 is a hydrogen atom, a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, or a sulfamoyl group,
n is an integer of 0 to 3,
R2 are each independently a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, or a sulfamoyl group,
X is a lower alkylene group optionally having substituent(s) (provided when the lower alkylene group has substituent(s) and
A is —CO$_2$R6, then the substituent is other than an oxo group),
Z is —N(R3)- wherein R3 is a hydrogen atom, a lower alkyl group optionally having substituent(s), a lower alkenyl group optionally having substituent(s), a lower alkynyl group optionally having substituent(s), or a lower cycloalkyl group optionally having substituent(s),
Y is a single bond or —(CH$_2$)$_p$—C(R4a)(R4b)-(CH$_2$)$_q$— wherein R4a and R4b are each independently a hydrogen atom, a lower alkyl group, or an aralkyl group, p and q are each an integer of 0 to 5, and p+q is an integer of 0 to 5,
A is —CO$_2$R6 wherein R6 is a hydrogen atom or a lower alkyl group, or a group represented by the formula (II)

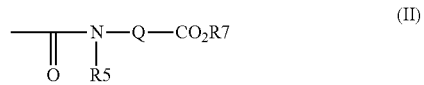

wherein
R5 is a hydrogen atom, a lower alkyl group optionally having substituent(s), a lower alkenyl group optionally having substituent(s), or a lower alkynyl group optionally having substituent(s), Q is a lower alkylene group optionally having substituent(s), and R7 is a hydrogen atom or a lower alkyl group, R2 and R3 are optionally bonded to form a hetero ring, R3 and R4a, or R3 and R4a and R4b are optionally bonded to form a hetero ring, and R4a and R4b are optionally bonded to form lower cycloalkane.

[2] The compound of the aforementioned [1], wherein D is a benzene ring or a naphthalene ring, or a pharmaceutically acceptable salt thereof.

[3] The compound of the aforementioned [1], wherein D is a benzene ring, or a pharmaceutically acceptable salt thereof.

[4] The compound of any one of the aforementioned [1] to [3], wherein R1 is a hydrogen atom or a halogen atom, or a pharmaceutically acceptable salt thereof.

[5] The compound of any one of the aforementioned [1] to [4], wherein Het is a 5- to 10-membered aromatic ring containing 1 to 3 hetero atoms, or a pharmaceutically acceptable salt thereof.

[6] The compound of the aforementioned [5], wherein, in the formula (I), the moiety represented by

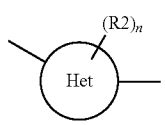

is a hetero ring represented by the formula (III-1) or (III-2)

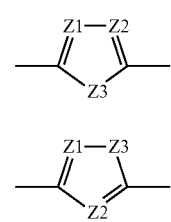

wherein Z1 and Z2 may be the same or different and each is independently CRa or a nitrogen atom, and Z3 is an oxygen atom, a sulfur atom or NRb wherein Ra and Rb may be the same or different and each is independently a hydrogen atom, a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group or a sulfamoyl group, and Ra and R3, or Rb and R3 are optionally bonded to form a hetero ring, or a pharmaceutically acceptable salt thereof.

[7] The compound of the aforementioned [6], wherein, in the formula (I), the moiety represented by

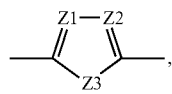

is a hetero ring represented by the formula (III-1)

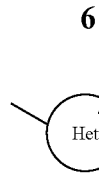

Z1 and Z2 are each CRa, and Z3 is an oxygen atom or a sulfur atom, or a pharmaceutically acceptable salt thereof.

[8] The compound of any one of the aforementioned [1] to [7], wherein X is a lower alkylene group optionally having substituent(s), wherein the substituent is selected from the group consisting of a halogen atom, a hydroxyl group, an amino group, a lower alkoxyl group, a lower acyl group, and an oxo group, or a pharmaceutically acceptable salt thereof.

[9] The compound of any one of the aforementioned [1] to [5] and [8], wherein n is 0, or n is 1 or 2, and R2 is a lower alkyl group, or a pharmaceutically acceptable salt thereof.

[10] The compound of any one of the aforementioned [1] to [9], wherein R3 is a hydrogen atom, a lower alkyl group optionally having substituent(s), a lower alkenyl group optionally having substituent(s), or a lower cycloalkyl group optionally having substituent(s), wherein the substituent is selected from the group consisting of a carboxyl group and —CONH—CH$_2$—CO$_2$H, or a pharmaceutically acceptable salt thereof.

[11] The compound of any one of the aforementioned [1] to [5] and [8], wherein R2 and R3 are bonded to form tetrahydropyridine, or a pharmaceutically acceptable salt thereof.

[12] The compound of any one of the aforementioned [1] to [11], wherein Y is a single bond or —C(R4a)(R4b)- wherein R4a and R4b are each independently a hydrogen atom, a lower alkyl group, or an aralkyl group, or a pharmaceutically acceptable salt thereof.

[13] The compound of any one of the aforementioned [1] to [9], wherein Y is —C(R4a)(R4b)-, R4b is a hydrogen atom, and R3 and R4a are bonded to form a hetero ring selected from the group consisting of pyrrolidine, piperidine, thiazolidine, and tetrahydroisoquinoline, or a pharmaceutically acceptable salt thereof.

[14] The compound of any one of the aforementioned [1] to [9], wherein Y is —C(R4a)(R4b)-, and R3 and R4a and R4b are bonded to form pyrrole, or a pharmaceutically acceptable salt thereof.

[15] The compound of any one of the aforementioned [1] to [11], wherein Y is —C(R4a)(R4b)-, and R4a and R4b are bonded to form a lower cycloalkane, or a pharmaceutically acceptable salt thereof.

[16] The compound of any one of the aforementioned [1] to [15], wherein A is —CO$_2$R6 wherein R6 is a hydrogen atom or a lower alkyl group, or a pharmaceutically acceptable salt thereof.

[17] The compound of any one of the aforementioned [1] to [15], wherein A is a group represented by the formula (II)

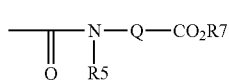
(II)

wherein
R5 is a hydrogen atom, a lower alkyl group optionally having substituent(s), a lower alkenyl group optionally having substituent(s), or a lower alkynyl group optionally having substituent(s),
Q is a lower alkylene group optionally having substituent(s), wherein the substituent is selected from the group consisting of a nitro group, a halogen atom, a cyano group, a hydroxyl group, a thiol group, an amino group, a guanidino group, a formyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, an arylsulfonylamino group optionally having substituent(s), a lower cycloalkyl group optionally having substituent(s), an aryl group optionally having substituent(s), an aryloxy group optionally having substituent(s), an arylthio group optionally having substituent(s), an aralkyl group optionally having substituent(s), an aralkyloxy group optionally having substituent(s), an aralkylthio group optionally having substituent(s), a heterocyclic group optionally having substituent(s), a heterocyclic oxy group optionally having substituent(s), a heterocyclic thio group optionally having substituent(s), and an oxo group, and
R7 is a hydrogen atom or a lower alkyl group, or a pharmaceutically acceptable salt thereof.
[18] The compound of the aforementioned [17], wherein X is a lower alkylene group substituted by an oxo group, or a pharmaceutically acceptable salt thereof.
[19] The compound of any one of the aforementioned [1] to [15], [17] and [18], wherein R5 is a hydrogen atom, a lower alkyl group optionally having substituent(s), or a lower alkenyl group optionally having substituent(s), wherein the substituent is selected from the group consisting of a hydroxyl group, a carboxyl group, a sulfo group, and a phosphono group, or a pharmaceutically acceptable salt thereof.
[20] The compound of any one of the aforementioned [1] to [15], [17], [18] and [19], wherein Q is a lower alkylene group optionally having substituent(s), wherein the substituent is selected from the group consisting of a carboxyl group and a sulfo group, or a pharmaceutically acceptable salt thereof.
[21] A compound of any of the formulas described below, or a pharmaceutically acceptable salt thereof:

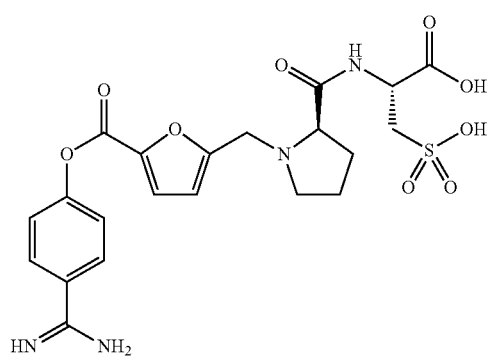

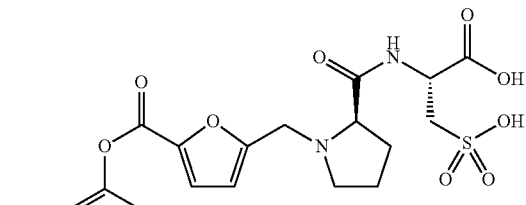

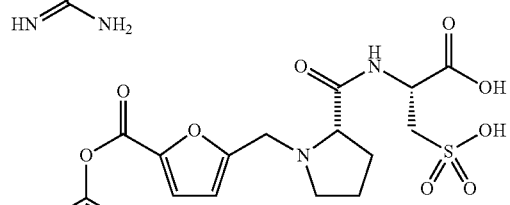

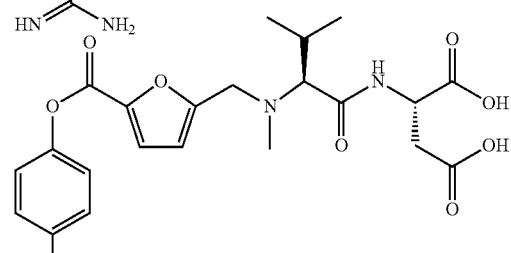

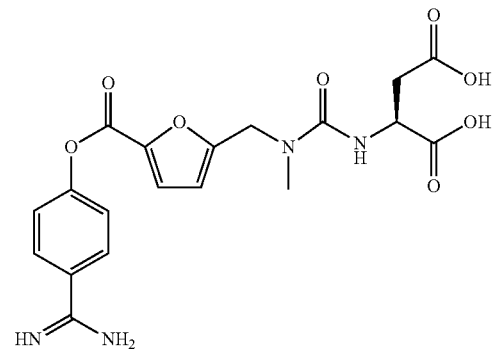

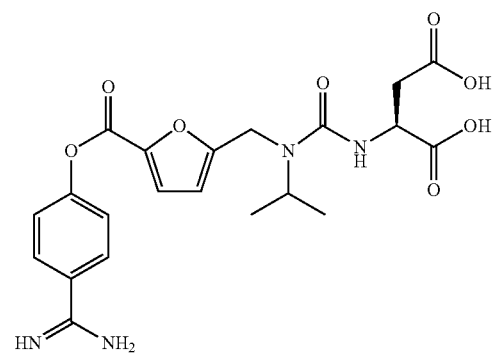

-continued
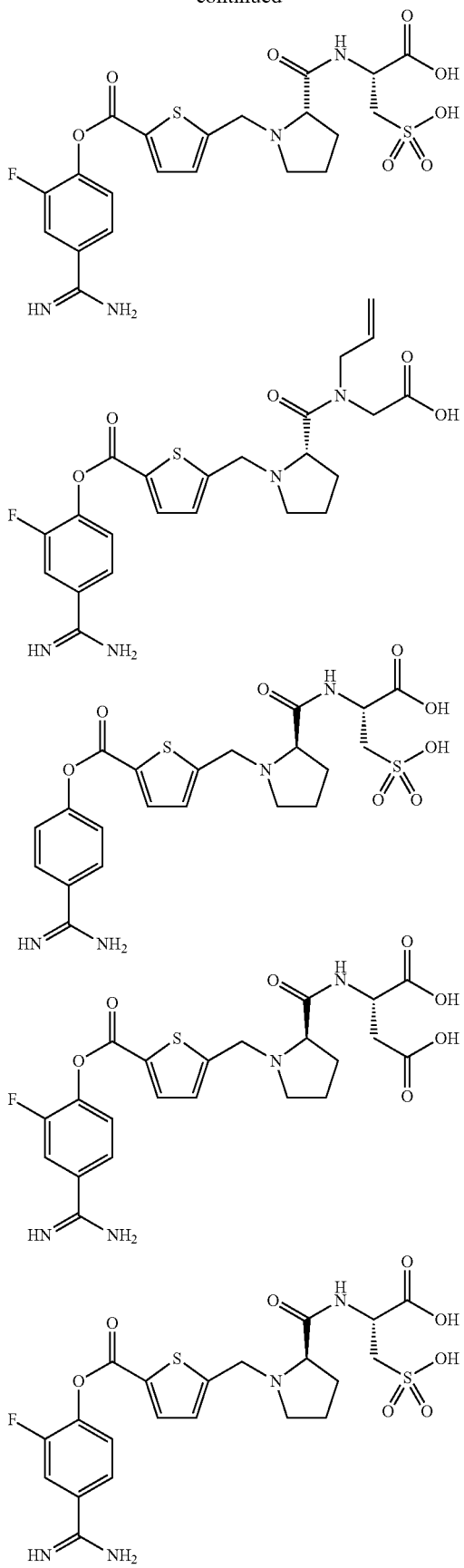
-continued
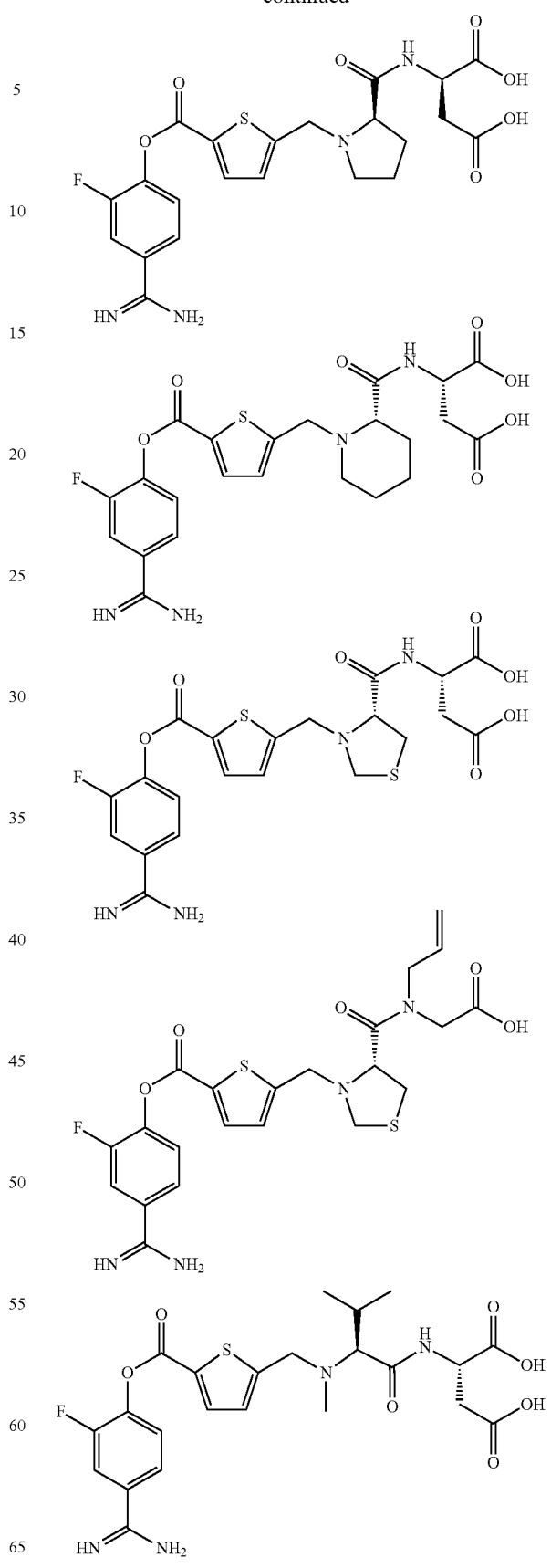

11
-continued
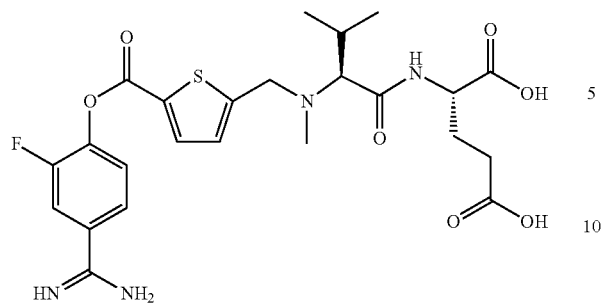
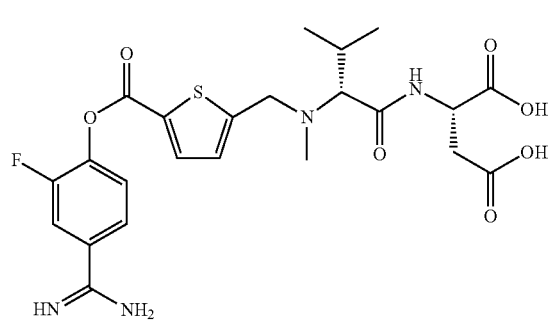
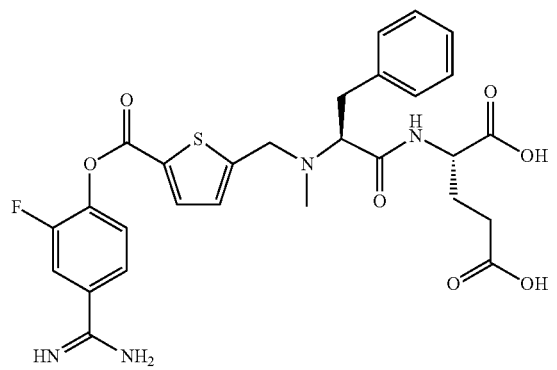
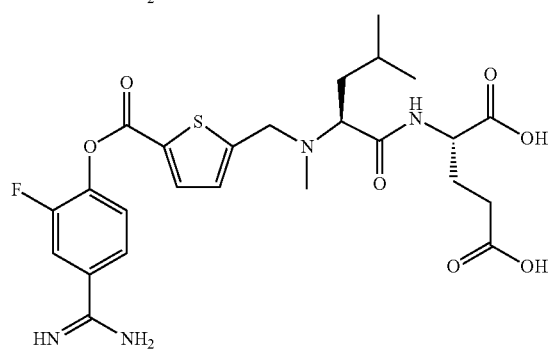
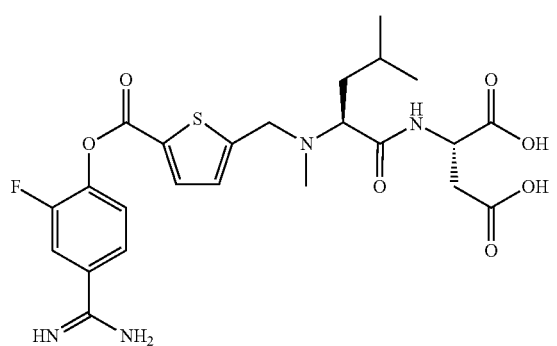
12
-continued
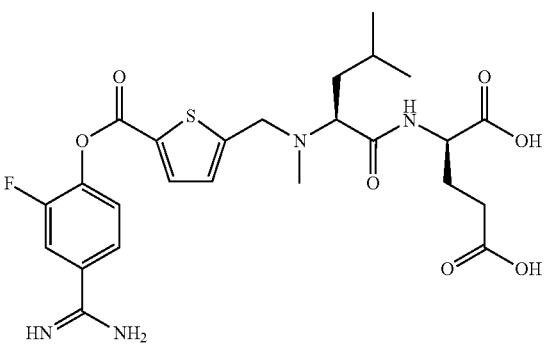
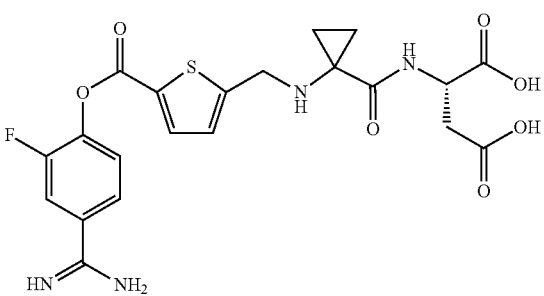
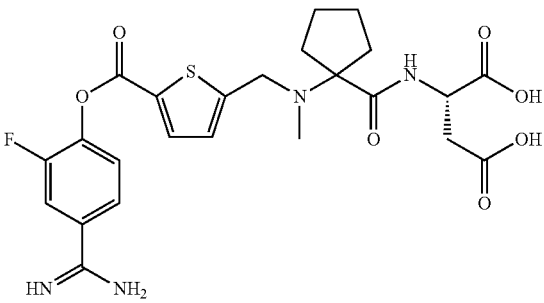
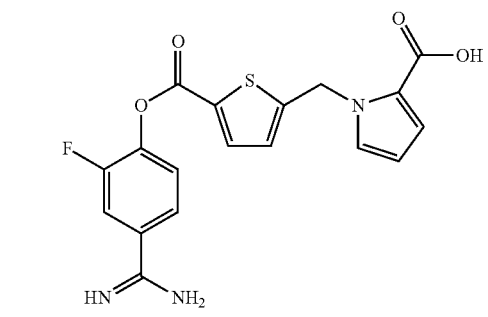
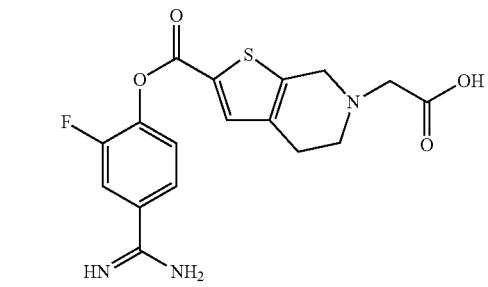

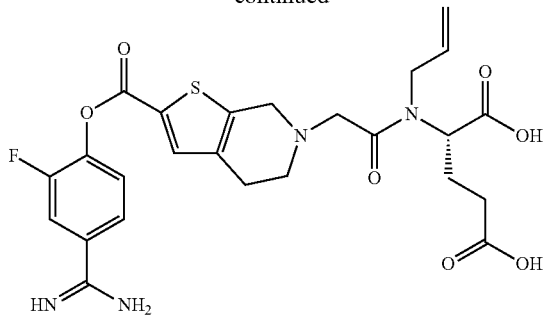

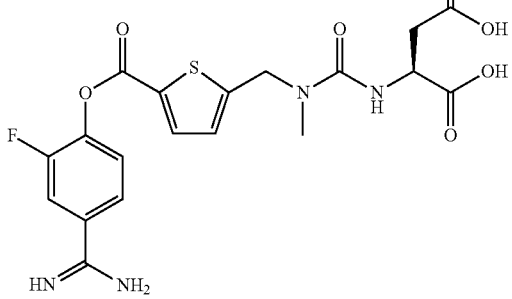

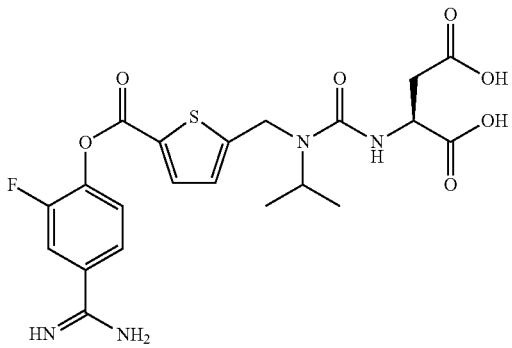

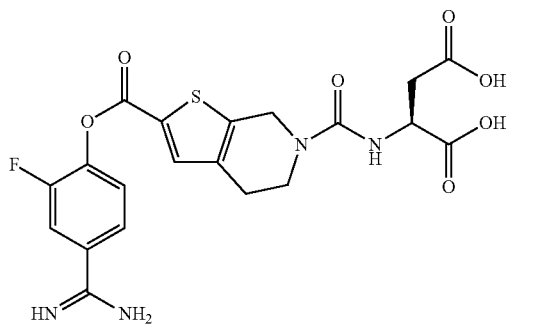

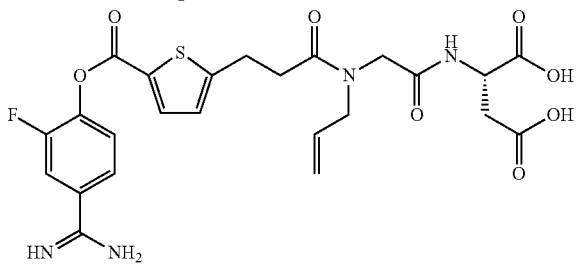

[22] A pharmaceutical composition comprising the compound of any one of the aforementioned [1] to [21], or a pharmaceutically acceptable salt thereof as an active ingredient.

[23] A serine protease inhibitor, comprising the compound of any one of the above-mentioned [1] to [21], or a pharmaceutically acceptable salt thereof as an active ingredient.

[24] An intestinal serine protease inhibitor, comprising the compound of any one of the above-mentioned [1] to [21], or a pharmaceutically acceptable salt thereof as an active ingredient.

[25] A dual inhibitor of trypsin and enteropeptidase, comprising the compound of any one of the above-mentioned [1] to [21], or a pharmaceutically acceptable salt thereof as an active ingredient.

[26] A hyperglycemic inhibitor or hypoglycemic agent, comprising the compound of any one of the above-mentioned [1] to [21], or a pharmaceutically acceptable salt thereof as an active ingredient.

[27] A prophylactic or therapeutic drug for diabetes, comprising the compound of any one of the above-mentioned [1] to [21], or a pharmaceutically acceptable salt thereof as an active ingredient.

[28] An insulin sensitizer comprising the compound of any one of the above-mentioned [1] to [21], or a pharmaceutically acceptable salt thereof as an active ingredient.

[29] A prophylactic or therapeutic drug for obesity, hyperlipidemia, diabetic complication or metabolic syndrome, comprising the compound of any one of the above-mentioned [1] to [21], or a pharmaceutically acceptable salt thereof as an active ingredient.

The present invention also relates to the following.

[30] A method for preventing or treating diabetes, comprising administering an effective amount of the compound of any one of the above-mentioned [1] to [21], or a pharmaceutically acceptable salt thereof.

[31] A method for improving insulin resistance, comprising administering an effective amount of the compound of any one of the above-mentioned [1] to [21], or a pharmaceutically acceptable salt thereof.

[32] A method for preventing or treating obesity, hyperlipidemia, diabetic complication or metabolic syndrome, comprising administering an effective amount of the compound of any one of the above-mentioned [1] to [21], or a pharmaceutically acceptable salt thereof.

[33] Use of the compound of any one of the above-mentioned [1] to [21], or a pharmaceutically acceptable salt thereof for the prophylaxis or treatment of diabetes.

[34] Use of the compound of any one of the above-mentioned [1] to [21], or a pharmaceutically acceptable salt thereof for the improvement of insulin resistance.

[35] Use of the compound of any one of the above-mentioned [1] to [21], or a pharmaceutically acceptable salt thereof for the prophylaxis or treatment of obesity, hyperlipidemia, diabetic complication or metabolic syndrome.

Effect of the Invention

Since the compound of the present invention has a serine protease inhibitory activity and a blood glucose elevation suppressive action, it can be preferably used as a drug for the prophylaxis or treatment of diabetes.

DESCRIPTION OF EMBODIMENTS

The present invention is explained in detail in the following.

In the present specification, the phrase "optionally having substituent(s)" means "being substituted or unsubstituted". Unless otherwise specified, the position and number of the substituents may be any, and are not particularly limited.

When substituted by two or more substituents, the substituents may be the same or different. Examples of the substituent include a nitro group, a halogen atom, a cyano group, a hydroxyl group, a thiol group, an amino group, a guanidino group, a formyl group, a phenyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, —CONH—CH$_2$—CO$_2$H, and the like.

In the present specification, examples of the substituent of the "arylsulfonylamino group optionally having substituent(s)", "cycloalkyl group optionally having substituent(s)", "aryl group optionally having substituent(s)", "aryloxy group optionally having substituent(s)", "arylthio group optionally having substituent(s)", "aralkyl group optionally having substituent(s)", "aralkyloxy group optionally having substituent(s)", "aralkylthio group optionally having substituent(s)", "heterocyclic group optionally having substituent(s)", "heterocyclic oxy group optionally having substituent(s)" and "heterocyclic thio group optionally having substituent(s)" include a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, —CONH—CH$_2$—CO$_2$H, and the like.

In the present specification, the "hetero ring" is a 5- to 10-membered hetero ring containing 1 to 3 hetero atoms such as a nitrogen atom, an oxygen atom, a sulfur atom, and the like, and a monocyclic and a fused hetero ring wherein two rings are fused can be mentioned.

As the "hetero ring", a "heteroaromatic ring" is preferable. The "heteroaromatic ring" is a 5- to 10-membered aromatic ring containing 1 to 3 hetero atoms such as a nitrogen atom, an oxygen atom, a sulfur atom, and the like, and examples thereof include a monocyclic, and a fused aromatic ring wherein two aromatic rings are fused. Examples of the monocyclic include furan, thiophene, pyrrole, oxazole, isoxazole, thiazole, isothiazole, imidazole, pyrazole, oxadiazole, thiadiazole, pyridine, pyridazine, pyrimidine, pyrazine, and the like. Examples of the fused aromatic ring include indole, isoindole, benzofuran, benzothiophene, indolizine, quinoline, isoquinoline, purine, 1H-indazole, quinazoline, cinnoline, quinoxaline, phthalazine, benzoxazole, benzothiazole, benzimidazole, and the like.

The "cyclic amino group" in the present specification is a saturated or unsaturated cyclic amino group having a carbon number of 2 to 7, which may contain one or more hetero atoms in the ring, such as a nitrogen atom, an oxygen atom, a sulfur atom, and the like. For example, a pyrrolidinyl group, a pyrrolinyl group, a piperidinyl group, a morpholinyl group, a piperazinyl group, a thiomorpholinyl group, a piperidinonyl group, a piperazinonyl group, and the like can be mentioned.

The "lower alkyl group" is a straight chain or branched chain or cyclic alkyl group having a carbon number of 1 to 6. For example, a methyl group, an ethyl group, an n-propyl group, an n-butyl group, an n-pentyl group, an n-hexyl group, an isopropyl group, an isobutyl group, a sec-butyl group, a tert-butyl group, an isopentyl group, a tert-pentyl group, a neopentyl group, a 2-pentyl group, a 3-pentyl group, a 2-hexyl group, a cyclopropyl group, a cyclopentyl group, and the like can be mentioned.

The "lower alkenyl group" is a straight chain or branched chain alkenyl group having a carbon number of 2 to 6, which includes each isomer. For example, a vinyl group, an allyl group, a propenyl group, a butenyl group, a pentenyl group, a hexenyl group, and the like can be mentioned.

The "lower alkynyl group" is a straight chain or branched chain alkynyl group having a carbon number of 2 to 6, which includes each isomer. For example, an ethynyl group, a 1-propynyl group, a 2-propynyl group, a 2-butynyl group, a 3-butynyl group, a pentynyl group, and the like can be mentioned.

The "lower alkylene group" is a straight chain or branched chain or cyclic alkylene group having a carbon number of 1 to 6, with preference given to a straight chain or a branched chain. For example, methylene group, ethylene group, trimethylene group (—(CH$_2$)$_3$—), tetramethylene group (—(CH$_2$)$_4$—), pentamethylene group (—(CH$_2$)$_5$—), hexamethylene group (—(CH$_2$)$_6$—), —CH$_2$—CH(CH$_3$)—, —CH$_2$—CH(CH$_2$CH$_3$)—, —CH$_2$—CH(CH$_2$CH$_2$CH$_3$)—, —CH$_2$—CH(CH$_3$)—CH$_2$CH$_2$—, —CH$_2$—CH(CH(CH$_3$)$_2$), —CH(CH$_2$CH$_3$)—CH(CH$_3$)—, —CH$_2$—C(CH$_3$)$_2$—, and the like can be mentioned.

Examples of the "halogen atom" include a fluorine atom, a chlorine atom, a bromine atom, an iodine atom, and the like.

The "lower acyl group" is an acyl group having a straight chain or branched chain or cyclic alkyl group or alkenyl group having a carbon number of 1 to 6. For example, an acetyl group, a propionyl group, a butyryl group, an isobutyryl group, a valeryl group, an isovaleryl group, a pivaloyl group, a hexanoyl group, an acryloyl group, a methacryloyl group, a crotonoyl group, an isocrotonoyl group, a cyclopropanoyl group, a cyclobutanoyl group, a cyclopentanoyl group, a cyclohexanoyl group, and the like can be mentioned.

The "lower alkoxyl group" is an alkoxyl group having a straight chain, a branched chain or a cyclic alkyl group having a carbon number of 1 to 6. For example, a methoxy group, an ethoxy group, an n-propoxy group, an n-butoxy group, an n-pentyloxy group, an n-hexyloxy group, an isopropoxy group, an isobutoxy group, a sec-butoxy group, a tert-butoxy group, a cyclopropyloxy group, a cyclobutyloxy group, a cyclopentyloxy group, and a cyclohexyloxy group can be mentioned.

The "lower alkylthio group" is an alkylthio group having a straight chain, a branched chain or a cyclic alkyl group having a carbon number of 1 to 6. For example, a methylthio group, an ethylthio group, an n-propylthio group, an isopropylthio group, an n-butylthio group, an isobutylthio group, a sec-butylthio group, a tert-butylthio group, a cyclopropylthio group, a cyclobutylthio group, a cyclopentylthio group, a cyclobutylthio group, and the like can be mentioned.

The "lower alkylamino group" is an amino group mono- or di-substituted by the aforementioned "lower alkyl group". For example, a methylamino group, an ethylamino group, a propylamino group, an isopropylamino group, a dimethylamino group, a diethylamino group, a dipropylamino group, a diisopropylamino group, an ethylmethylamino group, and the like can be mentioned.

The "lower acyloxy group" is a group wherein an oxygen atom is bonded to the carbon of the carbonyl moiety of the aforementioned "lower acyl group". For example, an acetyloxy group, a propionyloxy group, a butyryloxy group, an isobutyryloxy group, a valeryloxy group, an isovaleryloxy group, a pivaloyloxy group, a hexanoyloxy group, an acryloyloxy group, a methacryloyloxy group, a crotonoyloxy group, an isocrotonoyloxy group, and the like can be mentioned.

The "lower acylamino group" is a group wherein a nitrogen atom is bonded to the carbon of the carbonyl moiety of the aforementioned "lower acyl group". For example, an acetylamino group, a propionylamino group, a butyrylamino group, an isobutyrylamino group, a valerylamino group, an isovalerylamino group, a pivaloylamino group, a hexanoylamino group, an acryloylamino group, a methacryloylamino group, a crotonoylamino group, an isocrotonoylamino group, and the like can be mentioned.

The "lower alkoxycarbonyl group" is a carbonyl group having the aforementioned "lower alkoxyl group". For example, a methoxycarbonyl group, an ethoxycarbonyl group, a propoxycarbonyl group, an isopropoxycarbonyl group, an n-butoxycarbonyl group, an isobutoxycarbonyl group, a sec-butoxycarbonyl group, a tert-butoxycarbonyl group, and the like can be mentioned.

The "lower alkylcarbamoyl group" is a group wherein a nitrogen atom of the aforementioned "lower alkylamino group" or "cyclic amino group", and a carbon atom of the carbonyl group are bonded. For example, an N-methylcarbamoyl group, an N-ethylcarbamoyl group, an N,N-dimethylcarbamoyl group, a 1-pyrrolidinylcarbonyl group, a 1-piperidinylcarbonyl group, a 4-morpholinylcarbonyl group, and the like can be mentioned.

The "lower alkylsulfonylamino group" is a group wherein a nitrogen atom is bonded to a sulfonyl group wherein the aforementioned "lower alkyl group" is bonded to a sulfur atom. For example, a methylsulfonylamino group, an ethylsulfonylamino group, a propylsulfonylamino group, an isopropylsulfonylamino group, a butylsulfonylamino group, an isobutylsulfonylamino group, and the like can be mentioned.

The "lower cycloalkane" is cycloalkane having 3-6 carbon atoms. For example, cyclopropane, cyclobutane, cyclopentane, and cyclohexane can be mentioned.

The "arylsulfonylamino group" is a group wherein a nitrogen atom is bonded to a sulfur atom of a sulfonyl group substituted by an aryl group. For example, a phenylsulfonylamino group, a naphthylsulfonylamino group, and the like can be mentioned.

The "lower cycloalkyl group" is a cycloalkyl group having 3-6 carbon atoms. For example, a cyclopropyl group, a cyclobutyl group, a cyclopentyl group, and a cyclohexyl group can be mentioned.

The "aryl group" is an aryl group having 6-14 carbon atoms. For example, a phenyl group, a naphthyl group, and the like can be mentioned.

The "aryloxy group" is an aryloxy group having 6-14 carbon atoms. For example, a phenoxy group, a naphthyloxy group, and the like can be mentioned.

The "arylthio group" is an arylthio group having 6-14 carbon atoms. For example, a phenylthio group, a naphthylthio group, and the like can be mentioned.

The "aralkyl group" is an arylalkyl group wherein the aryl moiety has 6-14 carbon atoms and the alkyl moiety has 1-6 carbon atoms. For example, a benzyl group, a phenethyl group, a naphthylmethyl group, and the like can be mentioned.

The "aralkyloxy group" is an arylalkyloxy group wherein the aryl moiety has 6-14 carbon atoms and the alkyl moiety has 1-6 carbon atoms. For example, a benzyloxy group, a phenethyloxy group, a naphthylmethyloxy group, and the like can be mentioned.

The "aralkylthio group" is an arylalkylthio group wherein the aryl moiety has 6-14 carbon atoms and the alkyl moiety has 1-6 carbon atoms. For example, a benzylthio group, a phenethylthio group, a naphthylmethylthio group, and the like can be mentioned.

The "heterocyclic group" is a 5- to 14-membered monocyclic to tricyclic heterocyclic group containing, as a ring atom, 1 to 4 hetero atoms selected from an oxygen atom, a sulfur atom, and a nitrogen atom. Any carbon atom as a ring atom may be substituted by an oxo group, and a sulfur atom or a nitrogen atom may be oxidized to form an oxide. In addition, it may be fused with a benzene ring. For example, a pyridyl group, a pyridazinyl group, a pyrimidinyl group, a pyrazinyl group, a furyl group, a thienyl group, a pyrrolyl group, an isoxazolyl group, an oxazolyl group, an isothiazolyl group, a thiazolyl group, a pyrazolyl group, an imidazolyl group, an oxadiazolyl group, a thiadiazolyl group, a triazolyl group, a tetrazolyl group, a benzofuranyl group, a benzothienyl group, an indolyl group, an isoindolyl group, a benzoxazolyl group (=a benzoxazolyl group), a benzothiazolyl group, a benzimidazolyl group (=a benzimidazolyl group), an indazolyl group, a benzisoxazolyl group, a benzisothiazolyl group, a benzofurazanyl group, a benzothiadiazolyl group, a purinyl group, a quinolinyl group, an isoquinolyl group, a cinnolinyl group, a phthalazinyl group, a quinazolinyl group, a quinoxalinyl group, a pteridinyl group, an imidazooxazolyl group, an imidazothiazolyl group, an imidazoimidazolyl group, a dibenzofuranyl group, a dibenzothienyl group, a carbazolyl group, an acridinyl group, a pyrrolidinyl group, a pyrazolidinyl group, an imidazolidinyl group, a pyrrolinyl group, a pyrazolinyl group, an imidazolinyl group, a tetrahydrofuranyl group, a tetrahydrothiophenyl group, a thiazolidinyl group, a piperidinyl group, a piperazinyl group, a quinuclidinyl group, a tetrahydropyranyl group, a tetrahydrothiopyranyl group, a morpholinyl group, a thiomorpholinyl group, a dioxolanyl group, a homopiperidinyl group, a homopiperazinyl group, an indolinyl group, an isoindolinyl group, a chromanyl group, an isochromanyl group, a tetrahydronaphthyridinyl group, an azaindolyl group, and the like can be mentioned. Preferably, a thiadiazolyl group, an imidazolyl group, a tetrazolyl group, a piperidinyl group, a piperazinyl group, a thiazolidinyl group, and the like can be mentioned.

The "heterocyclic oxy group" is a heterocyclic oxy group wherein the heterocyclic moiety is the aforementioned "heterocyclic group". For example, a thiadiazolyloxy group, an imidazolyloxy group, a tetrazolyloxy group, a piperidinyloxy group, a piperazinyloxy group, a thiazolidinyloxy group, and the like can be mentioned.

The "heterocyclic thio group" is a heterocyclic thio group wherein the heterocyclic moiety is the aforementioned "heterocyclic group". For example, a thiadiazolylthio group, an imidazolylthio group, a tetrazolylthio group, a piperidinylthio group, a piperazinylthio group, a thiazolidinylthio group, and the like can be mentioned.

The "serine protease" in the present specification is a protease having, as a catalytic residue, a serine residue having nucleophilicity. For example, trypsin, chymotrypsin, elastase, enteropeptidase, kallikrein, thrombin, factor Xa, tryptase, and the like can be mentioned. In addition, the "serine protease inhibition" in the present specification means decrease or disappearance of the aforementioned serine protease activity. Preferably, it is an inhibition of the activity of intestinal serine proteases such as trypsin, enteropeptidase, chymotrypsin, elastase, and the like, particularly preferably inhibition of trypsin and enteropeptidase activities.

The serine protease inhibitor of the present invention is a dual inhibitor that simultaneously inhibits at least trypsin and enteropeptidase.

The diabetes in the present specification means type I diabetes mellitus and type II diabetes mellitus, with preference given to type II diabetes mellitus.

In the present invention, the heterocyclic carboxylic acid ester derivative represented by the formula (I) or a pharmaceutically acceptable salt thereof is preferably as follows.

In the formula (I), D is preferably a benzene ring or a naphthalene ring, more preferably a benzene ring In the formula (I), R1 is preferably a hydrogen atom, a nitro group, a halogen atom, and the like. Furthermore, a hydrogen atom, a halogen atom (e.g., a fluorine atom, a chlorine atom, a bromine atom), and the like are more preferable, and a hydrogen atom, a fluorine atom and the like are particularly preferable.

In the formula (I), the hetero ring represented by Het is preferably a 5- to 10-membered aromatic ring containing 1 to 3 hetero atoms, and furan, thiophene, oxazole, isoxazole, thiazole, isothiazole, benzofuran, benzothiophene, benzoxazole, benzothiazole, and the like can be mentioned. A 5-membered heteroaromatic ring is more preferable, and furan, thiophene, oxazole, isoxazole, thiazole, isothiazole, and the like can be mentioned, further preferably, furan, thiophene, thiazole, and the like can be mentioned, and particularly preferably furan, thiophene, and the like can be mentioned.

Here, as the hetero atom, an oxygen atom, a sulfur atom, a nitrogen atom, and the like can be mentioned.

R2 are each independently a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, or a sulfamoyl group. Preferably, a halogen atom, a hydroxyl group, an amino group, a lower alkyl group, a lower alkenyl group, a lower alkynyl group, a lower acyl group, a carboxyl group, a sulfo group, a phosphono group, a lower alkoxyl group, a lower alkylamino group, a lower alkoxycarbonyl group, a carbamoyl group, a lower alkylcarbamoyl group, a lower alkylsulfonylamino group, a sulfamoyl group, and the like can be mentioned. More preferably, a halogen atom, a hydroxyl group, an amino group, a lower alkyl group, a lower alkoxyl group, a lower alkylamino group, and the like can be mentioned. Particularly preferably, a lower alkyl group can be mentioned.

n is an integer of 0 to 3, more preferably an integer of 0 to 2, further preferably 0 or 1. In addition, n is preferably 0.

In a preferable embodiment, n is 0, or n is 1 or 2 and R2 is a lower alkyl group.

Moreover, R2 and R3 are optionally bonded to form a hetero ring. Examples of the hetero ring formed by R2 and R3 bonded to each other include a 5- or 6-membered hetero ring having 1 or 2 nitrogen atoms, preferably, a 6-membered hetero ring having one nitrogen atom (e.g., tetrahydropyridine etc.).

In the formula (I), the moiety represented by

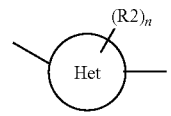

is also preferably a hetero ring represented by the following formula (III-1) or (III-2):

(III-1)

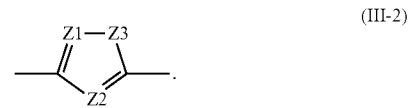

(III-2)

In the formula (III-1) or (III-2), Z1 and Z2 are each independently CRa or a nitrogen atom, and Z3 is an oxygen atom, a sulfur atom or NRb, wherein Ra and Rb may be the same or different, and are each independently selected from a hydrogen atom, a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, and a sulfamoyl group, and Ra and R3, or Rb and R3 are optionally bonded to form a hetero ring.

In the formulas (III-1) and (III-2), Z1 is preferably CH or a nitrogen atom, and CH is particularly preferable.

In the formulas (III-1) and (III-2), Z2 is preferably CH.

In the formulas (III-1) and (III-2), Z3 is preferably an oxygen atom or a sulfur atom.

In the formulas (III-1) and (III-2), preferably, Ra and Rb are each independently a hydrogen atom, a halogen atom, a hydroxyl group, an amino group, a lower alkyl group, a lower alkenyl group, a lower alkynyl group, a lower acyl group, a carboxyl group, a sulfo group, a phosphono group, a lower alkoxyl group, a lower alkylamino group, a lower alkoxycarbonyl group, a carbamoyl group, a lower alkylcarbamoyl group, a lower alkylsulfonylamino group, a sulfamoyl group, and the like, and a hydrogen atom, a halogen atom, a hydroxyl group, an amino group, a lower alkyl group, a lower alkoxyl group, a lower alkylamino group, and the like are more preferable, and a hydrogen atom and a lower alkyl group are further preferable.

In addition, Ra and R3, or Rb and R3 are optionally bonded to form a hetero ring. Examples of the hetero ring formed by Ra and R3, or Rb and R3 bonded to each other include a 5- or 6-membered hetero ring having 1 or 2 nitrogen atoms, with preference given to a 6-membered hetero ring having one nitrogen atom (e.g., tetrahydropyridine etc.).

More preferably, in the formula (I), the moiety represented by

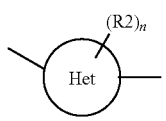

is a hetero ring represented by the aforementioned formula (III-1), Z1 and Z2 are each CRa, and Z3 is an oxygen atom or a sulfur atom.

Ra is preferably a hydrogen atom or a lower alkyl group, more preferably a hydrogen atom.

Ra and R3 are optionally bonded to form a hetero ring. Examples of the hetero ring formed by Ra and R3 bonded to each other include a 5- or 6-membered hetero ring having 1 or 2 nitrogen atoms, preferably, a 6-membered hetero ring having one nitrogen atom (e.g., tetrahydropyridine etc.).

In the formula (I), X is preferably a straight chain or branched chain lower alkylene group having 1 to 6 carbon atoms, more preferably a straight chain or branched chain lower alkylene group having 1 to 5 carbon atoms, further preferably a methylene group, an ethylene group or a trimethylene group.

In the formula (I), when a lower alkylene group for X has substituent(s), examples of the substituent include a nitro group, a halogen atom, a cyano group, a hydroxyl group, a thiol group, an amino group, a lower alkyl group, a guanidino group, a formyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, a sulfamoyl group, an oxo group, and the like. Preferred are a halogen atom, a hydroxyl group, an amino group, a lower alkyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, a sulfamoyl group, an oxo group, and the like. When the lower alkylene group for X has substituent(s) and A is —$CO_2R6$, the substituent is other than an oxo group. The number of the substituents is preferably 1 to 3, more preferably 1 or 2, further preferably 1. The lower alkylene group for X is also preferably unsubstituted.

An embodiment wherein X is a lower alkylene group optionally having substituent(s), and wherein substituent is selected from the group consisting of a halogen atom, a hydroxyl group, an amino group, a lower alkoxyl group, a lower acyl group, and oxo group is also preferable. When the lower alkylene group for X has substituent(s) and A is —$CO_2R6$, the substituent is other than an oxo group. The number of the substituents is preferably 1 to 3, more preferably 1 or 2, further preferably 1. The lower alkylene group for X is also preferably unsubstituted.

An embodiment wherein X is a straight chain or branched chain lower alkylene group having 1 to 6 carbon atoms (e.g., methylene group, ethylene group, trimethylene group) optionally having an oxo group is also preferable. However, when A is —$CO_2R6$, the lower alkylene group for X is unsubstituted.

In the formula (I), Z is —N(R3)- wherein R3 is a hydrogen atom, a lower alkyl group optionally having substituent(s), a lower alkenyl group optionally having substituent(s), a lower alkynyl group optionally having substituent(s), or a lower cycloalkyl group optionally having substituent(s).

When the group for R3 has substituent(s), examples of the substituent include a nitro group, a halogen atom, a cyano group, a hydroxyl group, a thiol group, an amino group, a lower alkyl group, a guanidino group, a formyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, a sulfamoyl group, —CONH—$CH_2$—$CO_2H$, and the like. Preferred are a hydroxyl group, a carboxyl group, a sulfo group, a phosphono group, —CONH—$CH_2$—$CO_2H$, and the like. More preferred are a carboxyl group, —CONH—$CH_2$—$CO_2H$, and the like. The number of the substituents is preferably 1 to 3, more preferably 1 or 2, further preferably 1. The group for X is also preferably unsubstituted.

An embodiment wherein R3 is a hydrogen atom, a lower alkyl group optionally having substituent(s), a lower alkenyl group optionally having substituent(s), or a lower cycloalkyl group optionally having substituent(s), wherein the substituent is selected from the group consisting of a carboxyl group and —CONH—$CH_2$—$CO_2H$ is preferable. The number of the substituents is preferably 1 to 3, more preferably 1 or 2, further preferably 1. The group for R3 is also preferably unsubstituted.

In the formula (I), Y is a single bond or —$(CH_2)_p$—C(R4a)(R4b)-$(CH_2)_q$— wherein R4a and R4b are each independently a hydrogen atom, a lower alkyl group, or an aralkyl group, p and q are each an integer of 0 to 5, and p+q is an integer of 0 to 5.

p and q are preferably each an integer of 0 to 2, more preferably 0 or 1, further preferably 0.

An embodiment wherein Y is a single bond or —C(R4a)(R4b)- wherein R4a and R4b are each independently a hydrogen atom, a lower alkyl group, or an aralkyl group is preferable.

An embodiment wherein Y is —C(R4a)(R4b)-, R4b is a hydrogen atom, and R3 and R4a are bonded to form a hetero ring is also preferable. Examples of the hetero ring formed by R3 and R4a bonded to each other include a 5- to 10-membered hetero ring having one nitrogen atom and further optionally having one hetero atom selected from an oxygen atom, a sulfur atom and a nitrogen atom (e.g., pyrrolidine, piperidine, thiazolidine, and tetrahydroisoquinoline etc.).

An embodiment wherein Y is —C(R4a)(R4b)-, and R3 and R4a and R4b are bonded to form a hetero ring is also preferable. Examples of the hetero ring formed by R3 and R4a and R4b bonded to each other include a 5- or 6-membered hetero ring having one nitrogen atom and further optionally having one hetero atom selected from an oxygen atom, a sulfur atom, and a nitrogen atom, with preference given to a 5-membered hetero ring having one nitrogen atom (e.g., pyrrole etc.).

An embodiment wherein Y is —C(R4a)(R4b)-, and R4a and R4b are bonded to form lower cycloalkane is also preferable. Examples of the lower cycloalkane formed by R4a and R4b bonded to each other include cyclopropane, cyclobutane, cyclopentane, and cyclohexane. Particularly preferred are cyclopropane and cyclopentane.

In the formula (I), A is —$CO_2R6$ wherein R6 is a hydrogen atom or a lower alkyl group, or a group represented by the formula (II)

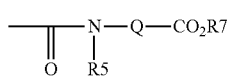
(II)

wherein

R5 is a hydrogen atom, a lower alkyl group optionally having substituent(s), a lower alkenyl group optionally having substituent(s), or a lower alkynyl group optionally having substituent(s), Q is a lower alkylene group optionally having substituent(s), and R7 is a hydrogen atom or a lower alkyl group.

When a group represented by A is —CO$_2$R6, R6 is preferably a hydrogen atom.

In the formula (II), R5 is preferably a hydrogen atom, a lower alkyl group optionally having substituent(s) or a lower alkenyl group optionally having substituent(s). Particularly, a methyl group, an ethyl group, a propyl group, or an allyl group is preferable.

In the formula (II), when a group for R5 has substituent(s), examples of the substituent include a hydroxyl group, a carboxyl group, a sulfo group, a phosphono group, and the like. Preferred are a carboxyl group, a sulfo group, and the like. The number of the substituents is preferably 1 to 3, more preferably 1 or 2, further preferably 1. The group for R5 is also preferably unsubstituted.

In the formula (II), Q is preferably a straight chain or branched chain alkylene group having 1 to 6 carbon atoms, more preferably a straight chain or branched chain alkylene group having 1 to 3 carbon atoms. For example, —CH$_2$—, —CH(CH$_3$)—, —CH(CH$_2$CH$_3$)—, and the like can be mentioned.

In the formula (II), when the lower alkylene group for Q has substituent(s), examples of the substituent include a nitro group, a halogen atom, a cyano group, a hydroxyl group, a thiol group, an amino group, a guanidino group, a formyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, an arylsulfonylamino group optionally having substituent(s), a lower cycloalkyl group optionally having substituent(s), an aryl group optionally having substituent(s), an aryloxy group optionally having substituent(s), an arylthio group optionally having substituent(s), an aralkyl group optionally having substituent(s), an aralkyloxy group optionally having substituent(s), an aralkylthio group optionally having substituent(s), a heterocyclic group optionally having substituent(s), a heterocyclic oxy group optionally having substituent(s), a heterocyclic thio group optionally having substituent(s), an oxo group, and the like. Preferred are a hydroxyl group, a carboxyl group, a sulfo group, a phosphono group, and the like, and more preferred are a carboxyl group and a sulfo group. The number of the substituents is preferably 1 to 3, more preferably 1 or 2, further preferably 1. The group for Q is also preferably unsubstituted.

As Q, a straight chain or branched chain alkylene group having 1-3 carbon atoms, which is substituted by one substituent selected from a carboxyl group and a sulfo group, can be mentioned.

In the formula (II), R7 is preferably a hydrogen atom.

A heterocyclic carboxylic acid ester derivative represented by any of the following formulas or a pharmaceutically acceptable salt thereof is preferable.

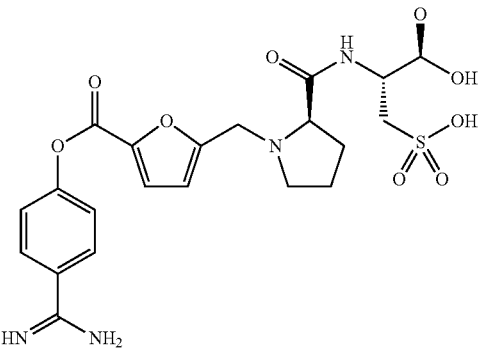

A-5

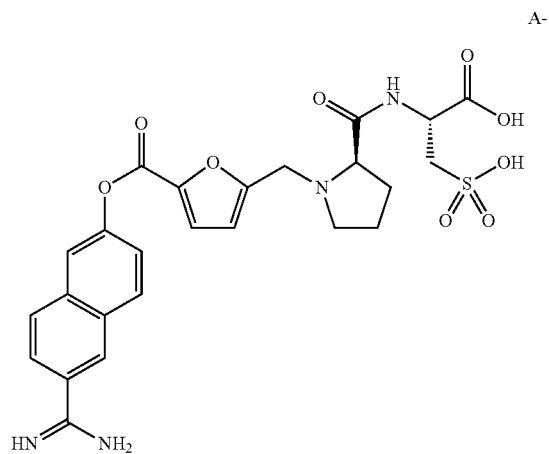

A-6

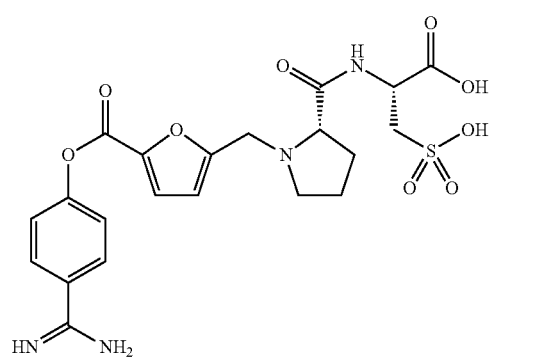

A-10

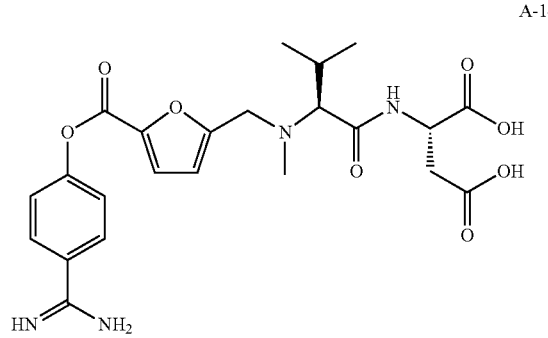

A-14

-continued
A-20
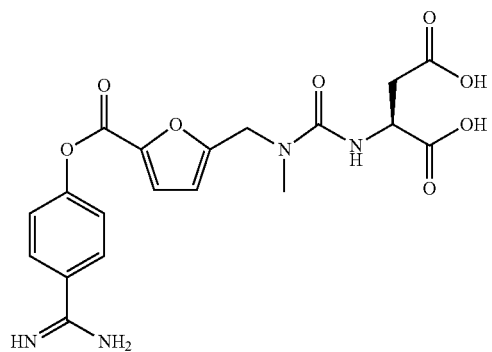
B-12
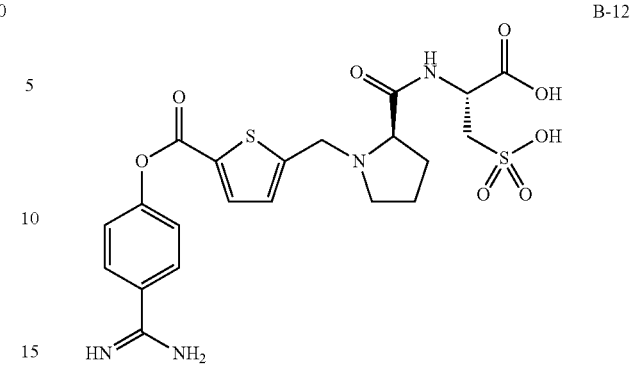
A-21
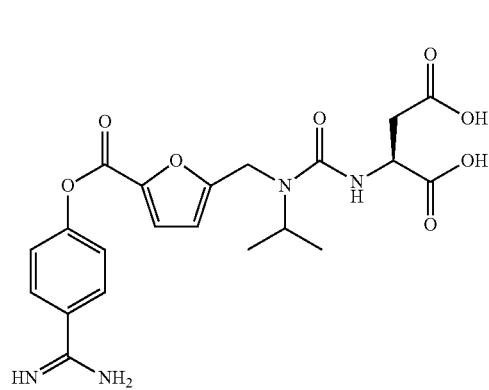
B-13
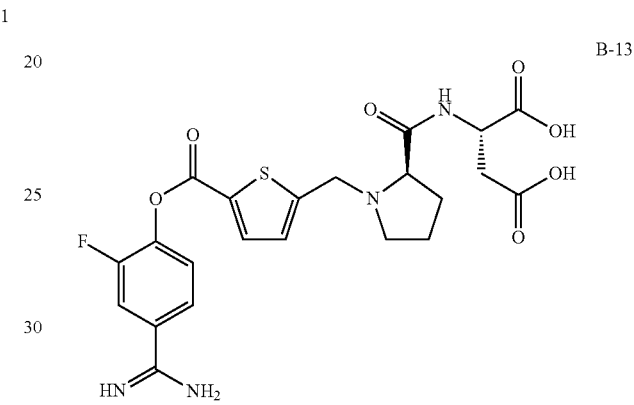
B-10
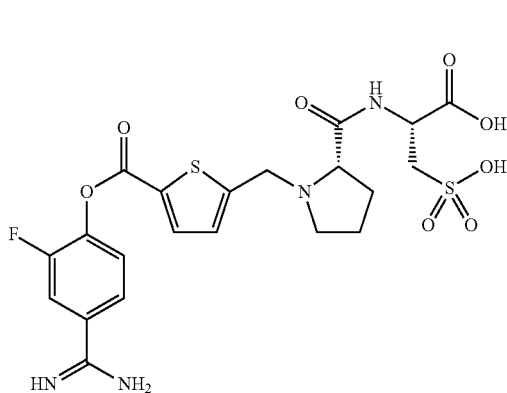
B-14
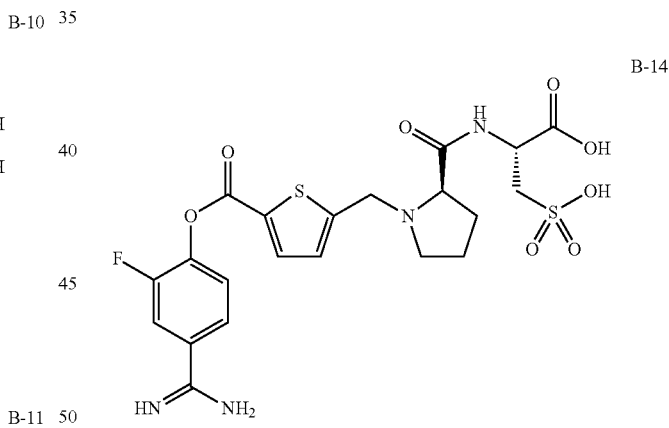
B-11
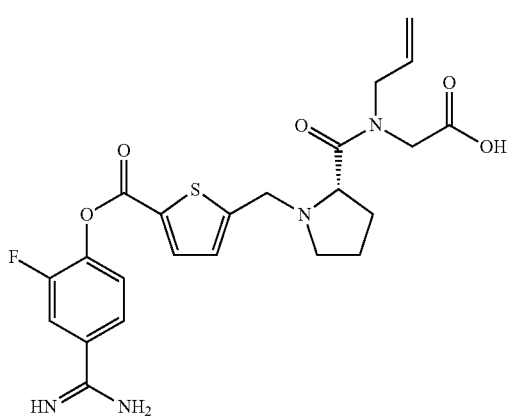
B-15
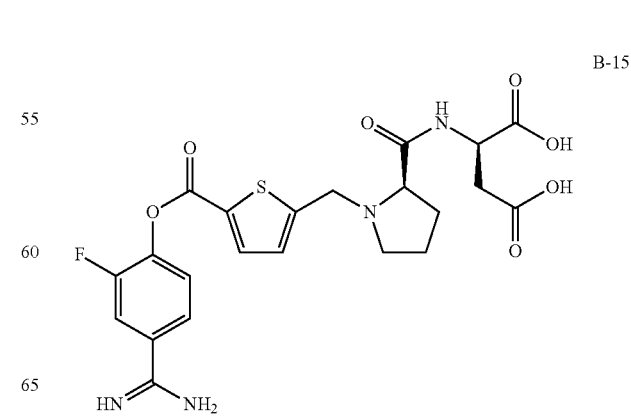

B-18
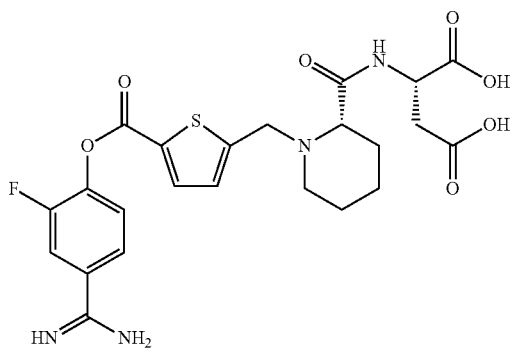
B-20
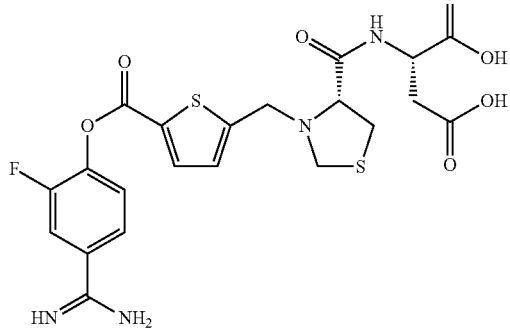
B-21
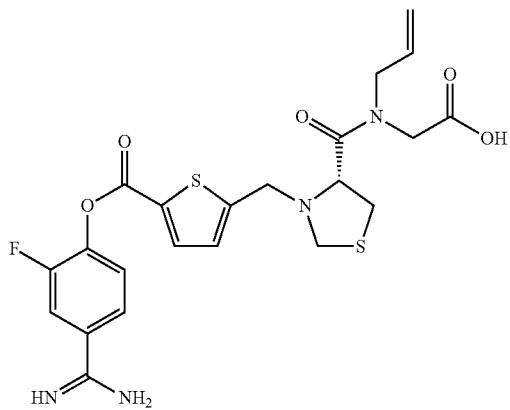
B-23
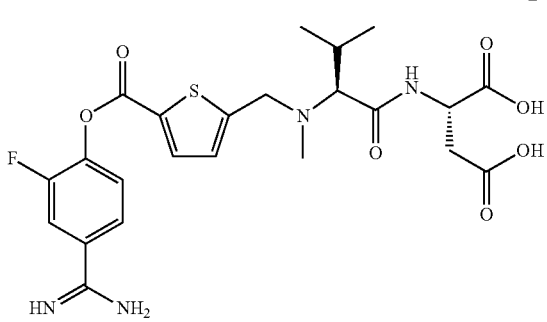
B-26
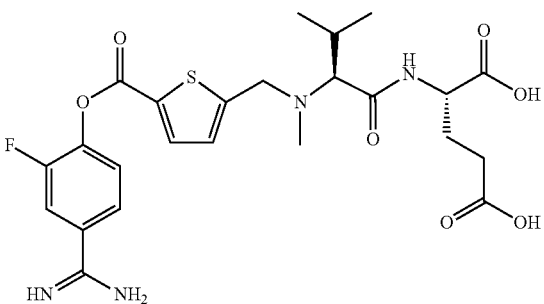
B-27
B-29
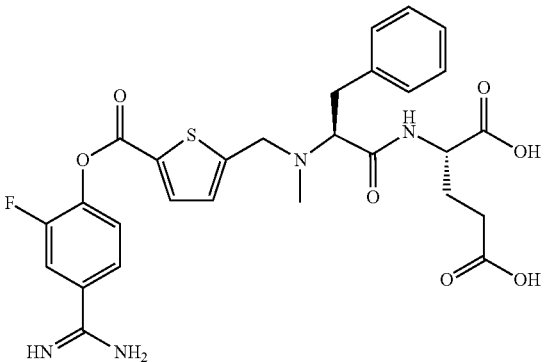
B-32
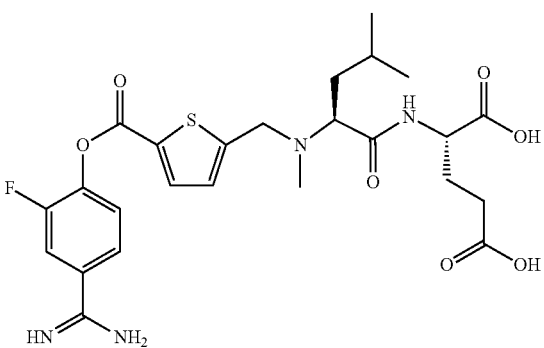

B-35
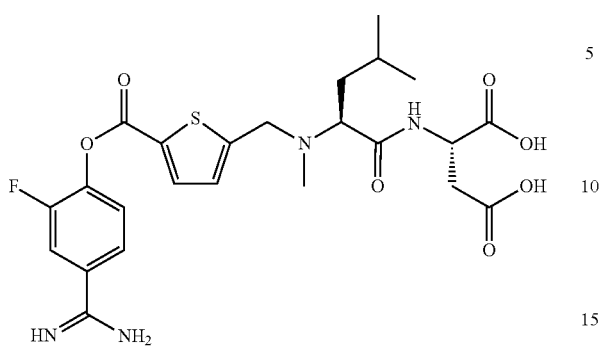
B-36
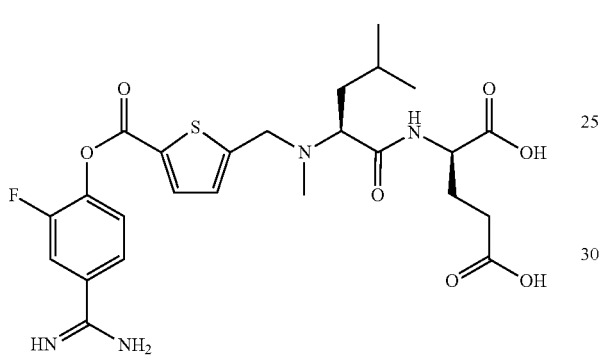
B-37
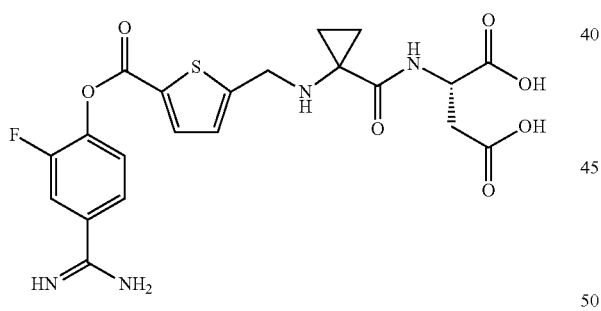
B-41
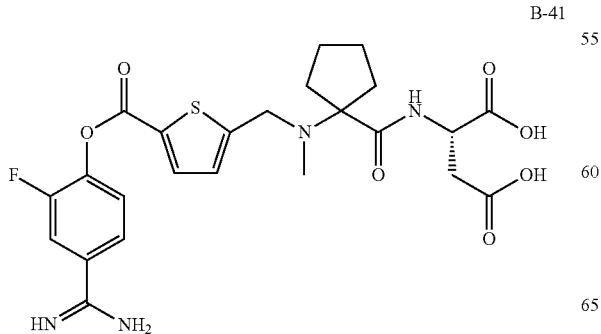
B-42
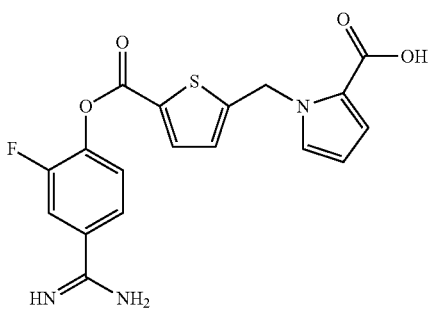
B-43
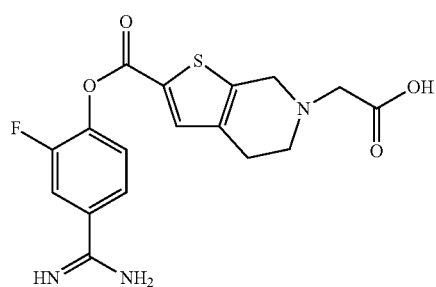
B-45
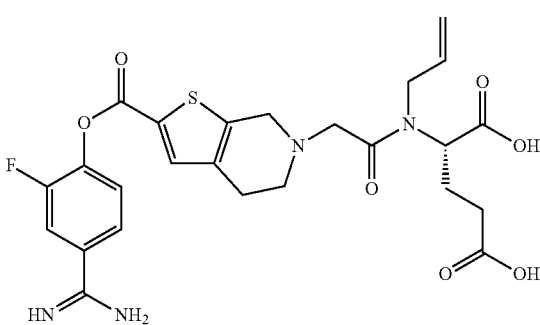
B-46
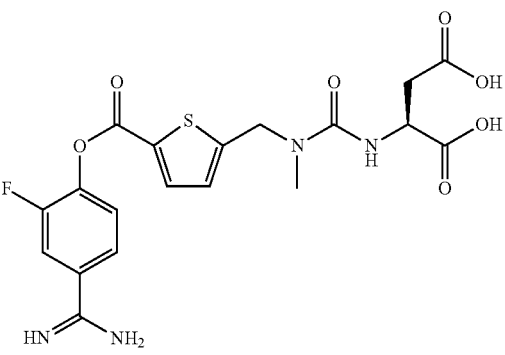

-continued

B-47
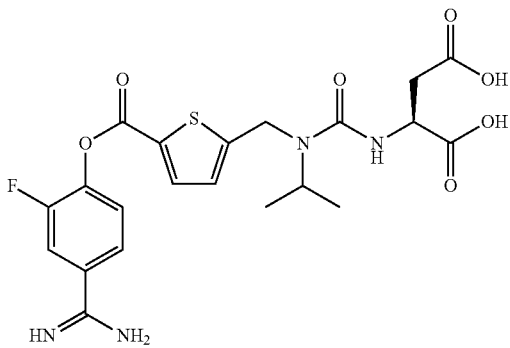

B-55
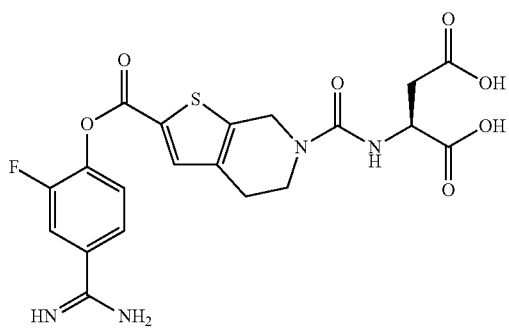

B-56
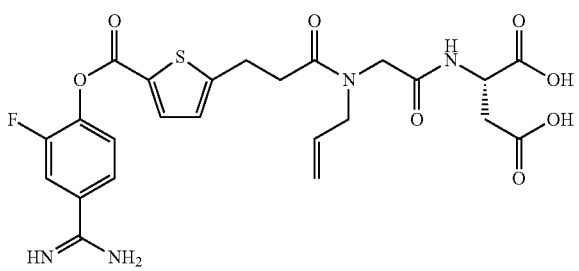

As preferable embodiments of the heterocyclic carboxylic acid ester derivative represented by the formula (I) or a pharmaceutically acceptable salt thereof, the following can also be mentioned.

[Compound a]

A compound represented by the formula (I), wherein
D is a benzene ring or a naphthalene ring,
R1 is a hydrogen atom or a halogen atom,
Het is furan or thiophene,
n is 0, or n is 1 or 2, and R2 is a lower alkyl group,
X is a lower alkylene group optionally having substituent(s), wherein the substituent is selected from the group consisting of a halogen atom, a hydroxyl group, an amino group, a lower alkoxyl group, a lower acyl group and an oxo group (provided when the lower alkylene group has substituent(s) and A is —CO$_2$R6, then the substituent is other than an oxo group),
Z is —N(R3)- wherein R3 is a hydrogen atom, a lower alkyl group optionally having substituent(s), a lower alkenyl group optionally having substituent(s), or a lower cycloalkyl group optionally having substituent(s), wherein the substituent is selected from the group consisting of a carboxyl group and —CONH—CH$_2$—CO$_2$H,
Y is a single bond or —C(R4a)(R4b)- wherein R4a and R4b are each independently a hydrogen atom, a lower alkyl group or an aralkyl group, A is —CO$_2$R6 wherein R6 is a hydrogen atom or a lower alkyl group, or a group represented by the formula (II)

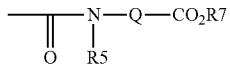

wherein
R5 is a hydrogen atom, a lower alkyl group optionally having substituent(s), or a lower alkenyl group optionally having substituent(s), wherein the substituent is selected from the group consisting of a hydroxyl group, a carboxyl group, a sulfo group, and a phosphono group,
Q is a lower alkylene group optionally having substituent(s), wherein the substituent is selected from the group consisting of a carboxyl group and a sulfo group,
R7 is a hydrogen atom or a lower alkyl group,
R2 and R3 are optionally bonded to form tetrahydropyridine,
R3 and R4a are optionally bonded to form a hetero ring selected from the group consisting of pyrrolidine, piperidine, thiazolidine, and tetrahydroisoquinoline,
R3 and R4a and R4b are optionally bonded to form pyrrole, and
R4a and R4b are optionally bonded to form lower cycloalkane, or a pharmaceutically acceptable salt thereof.

As the serine protease inhibitory activity, an activity of simultaneously inhibiting trypsin and enteropeptidase is preferable.

When the compound of the present invention can form a salt, a pharmaceutically acceptable salt is preferable. Examples of such pharmaceutically acceptable salts for a compound having an acidic group such as a carboxyl group and the like include an ammonium salt, salts with alkali metals such as sodium, potassium, and the like, salts with alkaline earth metals such as calcium, magnesium, and the like, an aluminum salt, a zinc salt, salts with an organic amines such as triethylamine, ethanolamine, morpholine, pyrrolidine, piperidine, piperazine, dicyclohexylamine, and the like, and salts with a basic amino acid such as arginine, lysine, and the like. Examples of such pharmaceutically acceptable salts for a compound having a basic group include salts with an inorganic acid such as hydrochloric acid, sulfuric acid, phosphoric acid, nitric acid, hydrobromic acid, and the like, salts with an organic carboxylic acid such as acetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, malic acid, and the like, and salts with an organic sulfonic acid such as methanesulfonic acid, benzenesulfonic acid, p-toluenesulfonic acid, and the like.

The compound of the present invention also encompasses all optical isomers, stereoisomers, tautomers, rotamers, and mixtures thereof at optional ratios. These can be obtained each as a single product according to a synthesis method and separation method known per se. For example, an optical isomer can be obtained by using an optically active synthetic intermediate or by optically resolving a racemate of a synthetic intermediate or final product by a conventional method.

The compound of the present invention also includes solvates of the compound such as hydrates, alcohol adducts and the like.

The compound of the present invention may be converted to a prodrug. The prodrug of the present invention means a compound that is converted in the body to produce the compound of the present invention. For example, when an active form contains a carboxyl group or a phosphoric acid group, an ester thereof, amide thereof, and the like can be mentioned. When an active form contains a carboxyl group, a group to be converted to a carboxyl group by oxidative metabolism, such as a hydroxymethyl group and the like can be mentioned. In addition, when the active form contains an amino group, examples thereof include amide thereof, a carbamate thereof and the like. When the active form contains a hydroxyl group, examples thereof include esters thereof, carbonates thereof, carbamates thereof, and the like. When the compound of the present invention is converted to a prodrug, it may be bonded to amino acid or saccharide.

The present invention also encompasses a metabolite of the compound of the present invention. The metabolite of the compound of present invention means a compound resulting from the conversion of the compound of the present invention by a metabolic enzyme and the like in the body. For example, a compound wherein a hydroxyl group is introduced on the benzene ring of the compound of the present invention due to the metabolism, a compound wherein glucuronic acid, glucose, or an amino acid is bonded to the carboxylic acid moiety of the compound of the present invention or a hydroxyl group is added by the metabolism, and the like can be mentioned.

The compound of the present invention and a pharmaceutically acceptable salt thereof have a superior blood glucose elevation suppressing action for mammals such as humans bovines, horses, dogs, mice, rats, and the like, and can be used as a medicament, which is administered as it is or as a pharmaceutical composition containing the same mixed with a pharmaceutically acceptable carrier according to a method known per se. While oral administration is generally preferable, parenteral administration can also be employed (e.g., routes such as intravenous, subcutaneous, intramuscular, suppository, enema, ointment, patch, sublingual, eye drop, inhalation administrations, and the like). While the dose used for the above-mentioned objects is determined according to the desired treatment effect, administration method, duration of treatment, age, body weight, and the like, a daily dose of 1 µg to 10 g for oral administration and 0.01 µg to 1 g for parenteral administration is used, which is generally administered to an adult by an oral or parenteral route in one to several portions per day. In addition, the content of the compound of the present invention in the above-mentioned pharmaceutical composition is about 0.01 wt % to 100 wt % of the whole composition.

Examples of the pharmaceutically acceptable carrier for the pharmaceutical composition of the present invention include various organic or inorganic carrier substances conventionally used as preparation materials. For example, an excipient, lubricant, binder, disintegrant, water-soluble polymer, and basic inorganic salt in a solid preparation; a solvent, solubilizing agents, suspending agent, isotonicity agent, buffering agent, and soothing agent in a liquid preparation, and the like can be mentioned. Where necessary, general additives such as a preservative, antioxidant, colorant, sweetening agent, souring agent, effervescing agent, flavor, and the like can also be used.

The dosage form of such pharmaceutical composition may be a tablet, powder, pill, granule, capsule, suppository, solution, sugar-coated agent, depot, syrup, suspension, emulsion, troche, sublingual agent, adhesive preparation, oral disintegrant (tablet), inhalant, enema, ointment, patch, tape, or eye drop, and these can be produced using conventional formulation auxiliaries and according to a conventional method.

The pharmaceutical composition of the present invention can be produced according to a method conventionally used in the technical field of pharmaceutical formulation, for example, the method described in the Japanese Pharmacopoeia and the like. Specific production methods of the preparation are explained in detail in the following.

For example, when the compound of the present invention is prepared as an oral preparation, an excipient and, where necessary, a binder, disintegrant, lubricant, colorant, flavoring agent, and the like are further added, and the mixture is processed to give, for example, a tablet, powder, pill, granule, capsule, suppository, solution, sugar-coated agent, depot, syrup, and the like according to a conventional method. Examples of the excipient include lactose, cornstarch, sucrose, glucose, sorbitol, crystalline cellulose, and the like. Examples of the binder include polyvinyl alcohol, polyvinyl ether, ethylcellulose, methylcellulose, gum arabic, tragacanth, gelatin, shellac, hydroxypropylcellulose, hydroxypropylstarch, polyvinylpyrrolidone, and the like. Examples of the disintegrant include starch, agar, gelatin powder, crystalline cellulose, calcium carbonate, sodium hydrogen carbonate, calcium citrate, dextran, pectin, and the like. Examples of the lubricant include magnesium stearate, talc, polyethylene glycol, silica, hydrogenated vegetable oil, and the like. As the colorant, one acceptable to add to a pharmaceutical product is used, and as the flavoring agent, cocoa powder, menthol, aromatic acid, peppermint oil, borneol, powdered cinnamon bark, and the like are used. Where necessary, these tablets and granules are applied with a coating as appropriate such as sugar coating, gelatin coating, and the like.

When an injection is to be prepared, a pH adjuster, buffering agent, stabilizer, preservative, and the like are added where necessary, and the mixture is processed to give subcutaneous, intramuscular, or intravenous injection according to a conventional method.

While the compound of the present invention can be used as an agent for the prophylaxis or treatment of diabetes as mentioned above, it can also be used in combination with other therapeutic agents for diabetes and agents for the prophylaxis or treatment of diabetic complications, which are used generally. Examples of the therapeutic agents for diabetes and agents for the prophylaxis or treatment of diabetic complications, which are used generally, include combinations and mixtures of one or more kinds of insulin preparation, insulin derivative, insulin-like agent, insulin secretagogue, insulin sensitizer, biguanide, gluconeogenesis inhibitor, glucose absorption inhibitor, renal glucose reabsorption inhibitor, β3 adrenoceptor agonist, glucagon-like peptide-1 (7-37), glucagon-like peptide-1 (7-37) analogs, glucagon-like peptide-1 receptor agonist, dipeptidyl peptidase IV inhibitor, aldose reductase inhibitor, inhibitor of advanced glycation end product formation, glycogen synthase kinase-3 inhibitor, glycogen phosphorylase inhibitor, antihyperlipidemic drug, anorectic agent, lipase inhibitor, antihypertensive agent, peripheral circulation improving agent, antioxidant, a therapeutic drug for diabetic neuropathy, and the like.

A medicament to be used in combination with the compound of the present invention may be mixed to give a single agent or each may be formulated into separate preparations, or prepared into a combination preparation (set, kit, pack) obtained by packaging each of the separately formulated preparations in one container.

The administration form of combined use is not particularly limited and, for example, (1) administration as a single preparation, (2) simultaneous administration of separate preparations by the same administration route, (3) administration of separate preparations in a staggered manner by the same administration route, (4) simultaneous administration of separate preparations by different administration routes, (5) administration of separate preparations in a staggered manner by different administration routes, and the like can be mentioned.

In addition, the compound of the present invention is also useful even when contained in food.

A food composition containing the compound of the present invention is useful as a food for the prophylaxis or treatment of diabetes.

The "food" of the present invention means general foods, which include food for specified health uses and food with nutrient function claims defined by Food with Health Claims of Consumer Affairs Agency, Government of Japan, in addition to general foods including so-called health food, and further encompasses dietary supplements.

The form of the food composition of the present invention is not particularly limited, and the composition may take any form as long as it can be orally ingested.

Examples thereof include powder, granule, tablet, hard capsules, soft capsule, liquid (drinks, jelly drinks, and the like), candy, chocolate, and the like, all of which can be produced according to a method known per se in the technical field.

The content of the compound of the present invention in the food composition is appropriately determined to afford an appropriate dose within the indicated range.

The food composition of the present invention can use other food additives as necessary. Examples of such food additive include those generally used as components of health foods such as a fruit juice, dextrin, cyclic oligosaccharide, saccharides (monosaccharides such as fructose, glucose, and the like, and polysaccharides), acidulant, flavor, powdered green tea, and the like, which are used for controlling and improving taste, emulsifier, collagen, whole milk powder, polysaccharide thickener, agar, and the like, which are used for improving texture, and further, vitamins, eggshell calcium, calcium pantothenate, the other minerals, royal jelly, propolis, honey, dietary fiber, Agaricus, chitin, chitosan, flavonoids, carotenoids, lutein, traditional Japanese herbal medicine, chondroitin, various amino acids, and the like.

A production method of a representative compound of the heterocyclic carboxylic acid ester derivatives represented by the formula (I), which is the compound of the present invention, is shown below.

A heterocyclic carboxylic acid ester derivative (f) of the formula (I) wherein Y is —(CH$_2$)$_p$—C(R4a)(R4b)-(CH$_2$)$_q$— wherein R4a and R4b are each independently a hydrogen atom, a lower alkyl group, or an aralkyl group, p and q are each an integer of 0 to 5, and p+q is an integer of 0 to 5, R3 and R4a, or R3 and R4a and R4b are optionally bonded to form a hetero ring, and R4a and R4b are optionally bonded to form lower cycloalkane can be produced as follows.

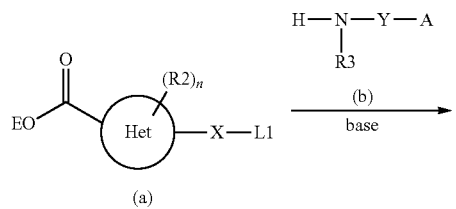

(a)

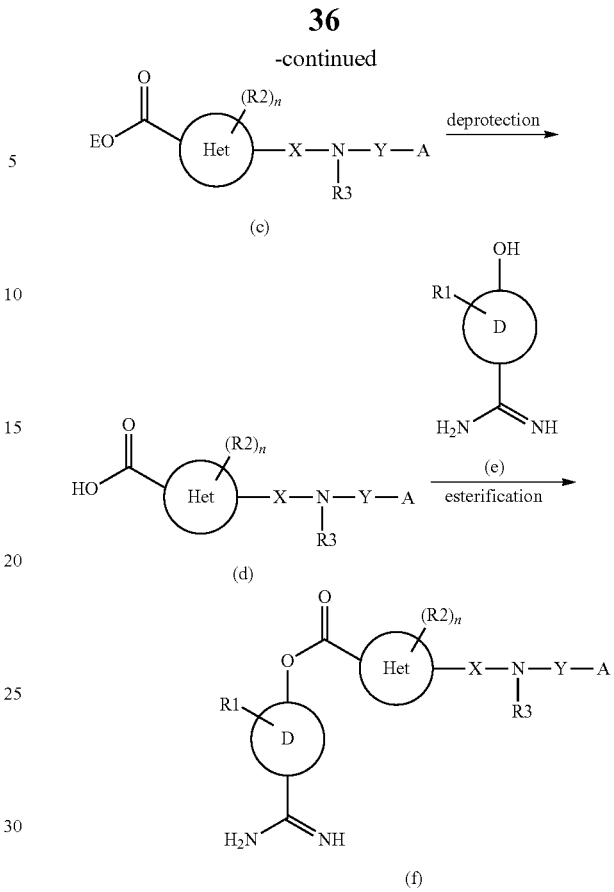

Amine derivative (c) can be synthesized by reacting compound (a) having a leaving group, wherein E is a protecting group such as a methyl group, an ethyl group, a tert-butyl group, and a benzyl group, and L1 is a halogen atom such as a chlorine atom, a bromine atom, and an iodine atom or a leaving group such as a methanesulfonyloxy group and a p-toluenesulfonyloxy group with amine (b) in a solvent that does not adversely influence the reaction, such as acetonitrile, tetrahydrofuran, and the like in the presence of a base such as N,N-diisopropylethylamine, sodium hydride, and the like and a catalyst such as sodium iodide, potassium iodide, tetra-n-butylammonium iodide, and the like. Amine derivative (c) can be induced to carboxylic acid derivative (d) by subjecting amine derivative (c) to deprotection in a solvent that does not adversely influence the reaction such as tetrahydrofuran, methanol, ethanol, and the like, such as alkali hydrolysis using sodium hydroxide and the like, or acid hydrolysis using hydrochloric acid, trifluoroacetic acid, and the like, or hydrogenation reaction in the presence of a palladium catalyst and the like, and the like. The object heterocyclic carboxylic acid ester derivative (f), wherein Y is —(CH$_2$)$_P$—C(R4a)(R4b)-(CH$_2$)$_q$— wherein R4a and R4b are each independently a hydrogen atom, a lower alkyl group or an aralkyl group, p and q are each an integer of 0 to 5, and p+q is an integer of 0 to 5, R3 and R4a, or R3 and R4a and R4b are optionally bonded to form a hetero ring, and R4a and R4b are optionally bonded to form lower cycloalkane, can be produced by esterifying carboxylic acid derivative (d) with 4-amidinophenol derivative (e).

Esterification reaction is known and, for example, (1) a method using acid halide, (2) a method using a condensing agent and the like can be mentioned.

(1) The method using acid halide is performed, for example, by reacting an acid chloride obtained by reacting carboxylic acid with thionyl chloride, oxalyl chloride, and the like in a solvent that does not adversely influence the reaction, such as dichloromethane and the like, or without solvent in the presence or absence of, for example, a catalyst such as N,N-dimethylformamide and the like, with alcohol in a solvent that does not adversely influence the reaction such as dichloromethane, tetrahydrofuran, and the like in the presence of a base such as pyridine and triethylamine.

(2) The method using a condensing agent is performed, for example, by reacting carboxylic acid with alcohol in, for example, a solvent that does not adversely influence the reaction such as tetrahydrofuran, N,N-dimethylformamide, dichloromethane, and the like in, for example, the presence or absence of a base such as pyridine, triethylamine, N,N-diisopropylethylamine, and the like or an acid such as 1-hydroxybenzotriazole, 1-hydroxy-7-azabenzotriazole, N-hydroxysuccinimide, and the like, by using a condensing agent such as 1-ethyl-3-(3'-dimethylaminopropyl)carbodiimide (WSC), 1,3-dicyclohexylcarbodiimide, and the like.

When R2 and R3 are bonded to form a hetero ring, heterocyclic carboxylic acid ester derivative (f) can be produced from compound (c), wherein R2 and R3 are bonded to form a hetero ring, by a method similar to the above.

Heterocyclic carboxylic acid ester derivative (1) of the formula (I) wherein Y is a single bond, and A is a group represented by the formula (II) can be produced as follows.

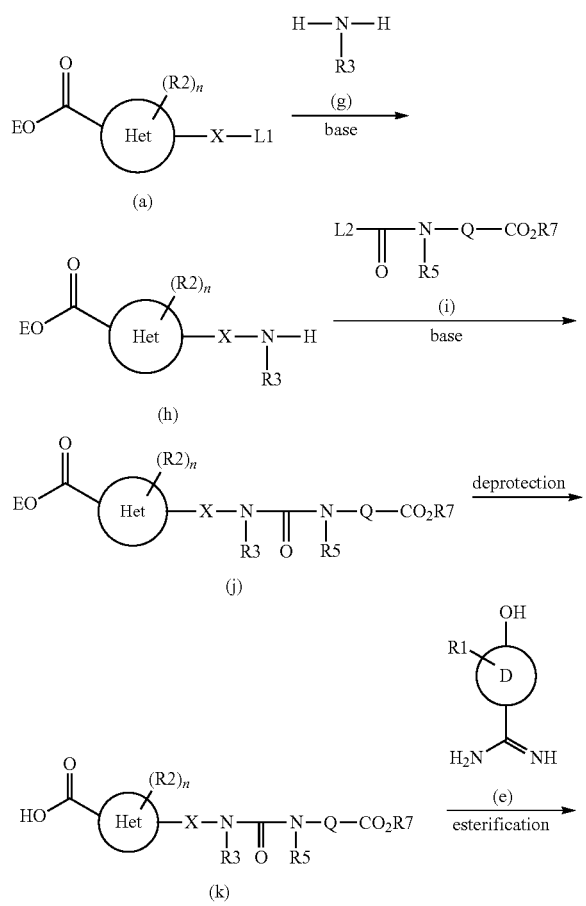

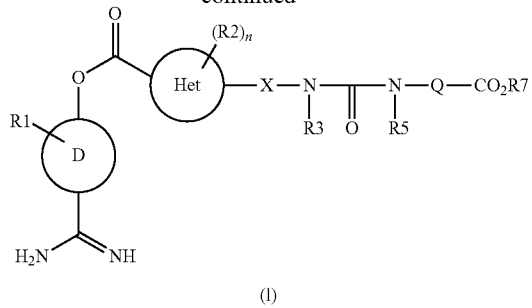

Amine derivative (h) can be synthesized by reacting compound (a) having a leaving group, wherein E is a protecting group such as a methyl group, an ethyl group, a tert-butyl group, and a benzyl group, and L1 is a halogen atom such as a chlorine atom, a bromine atom, and an iodine atom or a leaving group such as a methanesulfonyloxy group and a p-toluenesulfonyloxy group with amine (g) in a solvent that does not adversely influence the reaction, such as acetonitrile, tetrahydrofuran, methanol, and the like in the presence of a base such as N,N-diisopropylethylamine and the like. Urea derivative (j) can be obtained by reacting the obtained amine derivative (h) with a reaction agent (i) wherein L2 is an imidazol-1-yl group, a phenoxy group, and the like in a solvent that does not adversely influence the reaction such as acetonitrile, N,N-dimethylformamide, and the like. The reaction agent (i) used here can be prepared by a reaction of the corresponding amine derivative with 1,1'-carbonyldiimidazole or phenyl chloroformate and the like. The urea derivative (j) can be induced to carboxylic acid derivative (k) by subjecting the urea derivative (j) to deprotection in a solvent that does not adversely influence the reaction such as tetrahydrofuran, methanol, ethanol, and the like, such as alkali hydrolysis using sodium hydroxide and the like, or acid hydrolysis using hydrochloric acid, trifluoroacetic acid, and the like, or hydrogenation reaction in the presence of a palladium catalyst and the like, and the like. The object heterocyclic carboxylic acid ester derivative (l), wherein Y is a single bond and A is a group represented by the formula (II) can be produced by esterifying carboxylic acid derivative (k) with 4-amidinophenol derivative (e).

When R2 and R3 are bonded to form a hetero ring, heterocyclic carboxylic acid ester derivative (l) can be produced from compound (h), wherein R2 and R3 are bonded to form a hetero ring, by a method similar to the above.

EXAMPLES

The present invention is explained in detail in the following by referring to Examples. They are preferable embodiments of the present invention and the present invention is not limited by the Examples.

Example 1

Synthesis of 4-amidino-2-fluorophenol trifluoroacetate (M-1)

To 3-fluoro-4-hydroxybenzonitrile (3.0 g, 22 mmol) were added ethanol (3 mL) and 4N hydrochloric acid in 1,4-dioxane (27 mL), and the mixture was stirred at room temperature. After 18 hours, the reaction mixture was concentrated, and dried with a vacuum pump. Then, the residue was dissolved in ethanol (60 ml), ammonium carbonate (10.5 g, 0.11 mol) was added, and the mixture was stirred at room temperature. After 20 hours, ethanol (150 ml) was added, the solid was separated by filtration, and the obtained solution was concentrated. The obtained residue was purified by high performance liquid chromatography (water-acetonitrile, each containing 0.1% trifluoroacetic acid) to give the title compound (0.79 g, 2.9 mmol, 13%).

$^1$H NMR (300 MHz, DMSO-$d_6$) δ 11.28 (1H, br s), 9.19 (2H, br s), 9.02 (2H, br s), 7.75 (1H, dd, J=2.4, 12.0 Hz), 7.59 (1H, m), 7.18 (1H, dd, J=8.4, 8.7 Hz).

MS (ESI) m/z 155 (M+H)$^+$

Example 2

Synthesis of L-cysteic acid methyl ester hydrochloride (M-2)

L-Cysteic acid (300 mg, 1.77 mmol) was dissolved in methanol (12 mL), and thionyl chloride (2.5 mL, 34 mmol) was slowly added dropwise at 0° C. After stirring at room temperature overnight, the reaction mixture was concentrated under reduced pressure, and the obtained residue was suspended in diisopropyl ether. The suspension was filtered to give the title compound as white crystals (291 mg, 1.33 mmol, 75%).

$^1$H NMR (300 MHz, DMSO-$d_6$) δ 8.26 (3H, br s), 4.23 (1H, m), 3.72 (3H, s), 3.00 (1H, dd, J=14.3, 3.5 Hz), 2.92 (1H, dd, J=14.3, 8.0 Hz).

MS (ESI) m/z 184 (M+H)$^+$

Example 3

Synthesis of N-allyl-L-aspartic acid di-tert-butyl ester hydrochloride (M-3)

Step 1. Synthesis of N-allyl-L-aspartic acid di-tert-butyl ester

L-Aspartic acid di-tert-butyl ester hydrochloride (1.0 g, 3.5 mmol) was dissolved in acetonitrile (7 mL), potassium carbonate (0.98 g, 7.1 mmol) and allyl bromide (0.29 mL, 3.4 mmol) were added, and the mixture was stirred at room temperature overnight. The insoluble material was removed by filtration, the filtrate was concentrated under reduced pressure and the obtained residue was purified by silica gel column chromatography (hexane/ethyl acetate=95/5) to give the title compound (0.50 g, 1.8 mmol).

$^1$H NMR (400 MHz, CDCl$_3$) δ 5.86 (1H, dddd, J=17.2, 10.2, 6.1, 5.9 Hz), 5.16-5.21 (1H, m), 5.06-5.10 (1H, m), 3.47 (1H, dd, J=6.8, 5.9 Hz), 3.30-3.36 (1H, m), 3.15-3.20 (1H, m), 2.60 (1H, dd, J=15.7, 5.9 Hz), 2.51 (1H, dd, J=15.7, 6.8 Hz), 1.47 (9H, s), 1.45 (9H, s).

MS (ESI) m/z 286 (M+H)$^+$

Step 2. Synthesis of N-allyl-L-aspartic acid di-tert-butyl ester hydrochloride (M-3)

To the compound (0.50 g, 1.8 mmol) obtained in step 1 were added water (17 mL) and 1N hydrochloric acid (1.8 mL, 1.8 mmol). Acetonitrile (10 ml) was added to dissolve the mixture, and the solution was concentrated under reduced pressure, and lyophilized to give the title compound (0.54 g, 1.7 mmol, 95%).

$^1$H NMR (400 MHz, DMSO-$d_6$) δ 9.25 (2H, br s), 5.84-5.94 (1H, m), 5.48 (1H, d, J=17.2 Hz), 5.41 (1H, d, J=9.6 Hz), 4.11 (1H, br s), 3.65 (1H, br s), 2.83-2.98 (2H, m), 1.45 (9H, s), 1.44 (9H, s).

MS (ESI) m/z 286 (M+H)$^+$

Example 4

Synthesis of N-allyl-L-glutamic acid di-tert-butyl ester hydrochloride (M-4)

Using L-glutamic acid di-tert-butyl ester hydrochloride instead of L-aspartic acid di-tert-butyl ester hydrochloride and by an operation similar to that in Example 3, the title compound was obtained.

$^1$H NMR (400 MHz, CDCl$_3$) δ 5.84 (1H, ddt, J=17.1, 10.2, 6.0 Hz), 5.21-5.13 (1H, m), 5.11-5.04 (1H, m), 3.30-3.22 (1H, m), 3.16-3.04 (2H, m), 2.34 (2H, ddd, J=8.3, 6.9, 3.3 Hz), 1.95-1.72 (2H, m), 1.47 (9H, s), 1.44 (9H, s).

MS (ESI) m/z 300 (M+H)$^+$

Example 5

Synthesis of N-allylglycine tert-butyl ester (M-5)

Allylamine (10 mL, 0.13 mol) was cooled to 0° C., a solution of bromoacetic acid tert-butyl ester (1.0 mL, 6.7 mmol) in dichloromethane (10 ml) was slowly added. After stirring at 0° C. for 3 hours, the reaction mixture was concentrated under reduced pressure. The obtained residue was dissolved in diethyl ether, washed successively with saturated aqueous sodium hydrogen carbonate and saturated brine, and dried over anhydrous sodium sulfate. The obtained solution was concentrated under reduced pressure to give the title compound as a yellow liquid (1.15 g, 6.7 mmol, 99%).

$^1$H NMR (400 MHz, DMSO-$d_6$) δ 5.87 (1H, ddt, J=17.1, 10.2, 6.1 Hz), 5.19 (1H, ddt, J=17.1, 3.2, 1.7 Hz), 5.11 (1H, ddt, J=10.2, 3.2, 1.2 Hz), 3.29 (2H, s), 3.25 (2H, ddd, J=6.1, 1.7, 1.2 Hz), 1.47 (9H, s).

MS (ESI) m/z 172 (M+H)$^+$

Example 6

Synthesis of 5-chloromethyl-2-thiophenecarboxylic acid tert-butyl ester (M-6)

5-Formyl-2-thiophenecarboxylic acid (25 g, 160 mmol) was dissolved in tert-butyl alcohol (400 ml) and dichloromethane (100 ml), di-tert-butyl bicarbonate (42.0 g, 192 mmol), and 4-dimethylaminopyridine (2.0 g, 16 mmol) were added, and the mixture was stirred at room temperature for 3 days. The solvent was evaporated under reduced pressure, ethyl acetate was added, and the mixture was washed successively with water, 0.5N aqueous sodium hydroxide solution and saturated brine. The ethyl acetate layer was dried over anhydrous sodium sulfate. The desiccant was filtered off, and the filtrate was concentrated under reduced pressure. 5 g of the obtained residue was dissolved in tetrahydrofuran (50 ml) and methanol (5 mL), sodium borohydride (0.50 g, 13 mmol) was added at 0° C., and the mixture was stirred for 2 hours. The reaction mixture was diluted with ethyl acetate, washed successively with 0.5N hydrochloric acid and saturated brine, and dried over anhydrous sodium sulfate. The desiccant was filtered off, and the filtrate was concentrated under reduced pressure. The obtained residue was dissolved in dichloromethane (100 ml), and methanesulfonyl chloride (1.9 mL, 24 mmol) and N,N-diisopropylethylamine (5.7 mL, 33 mmol) were added at 0° C., and the mixture was stirred overnight. The solvent was concentrated under reduced pressure, ethyl acetate was added, and the mixture was washed successively with water and saturated brine. The ethyl acetate layer was dried over anhydrous sodium sulfate. The desiccant was filtered off, and the filtrate was concentrated under reduced pressure. The obtained residue was purified by silica gel column chromatography (hexane/ethyl acetate) to give the title compound (5.3 g, 23 mmol).

$^1$H NMR (400 MHz, CDCl$_3$) δ 7.56 (1H, d, J=3.8 Hz), 7.03 (1H, d, J=3.8 Hz), 4.75 (2H, s), 1.57 (9H, s).

Example 7

Synthesis of N-{[5-(4-amidinophenoxycarbonyl)furan-2-yl]methyl}-D-proline bis(trifluoroacetate) (A-1)

Step 1. Synthesis of (R)-2-{[2-(tert-butoxycarbonyl)pyrrolidin-1-yl]methyl}furan-5-carboxylic acid trifluoroacetate To a solution of D-proline tert-butyl ester hydrochloride (1.0 g, 4.8 mmol) in acetonitrile (30 ml) were added 5-chloromethylfuran-2-carboxylic acid ethyl ester (0.37 mL, 2.4 mmol) and N,N-diisopropylethylamine (1.5 mL, 8.4 mmol), and the mixture was stirred at room temperature overnight. The reaction mixture was concentrated under reduced pressure and tetrahydrofuran (10 ml) was added to the obtained residue. The precipitate was removed by filtration, and 4N aqueous sodium hydroxide solution (4.0 mL, 16 mmol), water (4 mL) and ethanol (5 mL) were added. After stirring at room temperature overnight, the reaction mixture was neutralized with 1N hydrochloric acid, and concentrated under reduced pressure. The obtained residue was purified by high performance liquid chromatography (water-acetonitrile, each containing 0.1% trifluoroacetic acid) to give the title compound (0.71 g, 1.7 mmol, 72%).

MS (ESI) m/z 296 (M+H)$^+$

Step 2. Synthesis of N-{[5-(4-amidinophenoxycarbonyl)furan-2-yl]methyl}-D-proline bis(trifluoroacetate) (A-1)

To the compound (0.71 g, 1.7 mmol) obtained in step 1, 4-amidinophenol hydrochloride (0.39 g, 2.3 mmol) and WSC hydrochloride (0.43 g, 2.3 mmol) was added pyridine (10 ml), and the mixture was stirred at room temperature overnight. The reaction mixture was concentrated under reduced pressure, trifluoroacetic acid (5 mL) was added to the obtained residue, and the mixture was stirred at room temperature for 2 hours. The reaction mixture was concentrated under reduced pressure and the obtained residue was purified by high performance liquid chromatography (water-acetonitrile, each containing 0.1% trifluoroacetic acid) to give the title compound (0.40 g, 0.68 mmol, 40%).

$^1$H NMR (400 MHz, D$_2$O) δ 7.84 (2H, d, J=8.8 Hz), 7.49 (1H, d, J=3.6 Hz), 7.44 (2H, d, J=8.8 Hz), 6.87 (1H, d, J=3.6 Hz), 4.58 (1H, d, J=14.3 Hz), 4.52 (1H, d, J=14.3 Hz), 4.12 (1H, dd, J=9.6, 6.6 Hz), 3.71-3.76 (1H, m), 3.28-3.35 (1H, m), 2.40-2.50 (1H, m), 1.90-2.14 (3H, m).

MS (ESI) m/z 358 (M+H)$^+$

Example 8

Synthesis of N—(N-{[5-(4-amidinophenoxycarbonyl)furan-2-yl]methyl}-D-prolyl)-L-aspartic acid bis(trifluoroacetate) (A-3)

Step 1. Synthesis of N—(N-{[5-(4-amidinophenoxycarbonyl)furan-2-yl]methyl}-D-prolyl)-L-aspartic acid di-tert-butyl ester bis(trifluoroacetate)

To A-1 (50 mg, 0.085 mmol), L-aspartic acid di-tert-butyl ester hydrochloride (29 mg, 0.10 mmol), and WSC hydrochloride (25 mg, 0.13 mmol) was added pyridine (1 mL), and the mixture was stirred at room temperature overnight. The reaction mixture was concentrated under reduced pressure and the obtained residue was purified by high performance liquid chromatography (water-acetonitrile, each containing 0.1% trifluoroacetic acid) to give the title compound (51 mg, 0.062 mmol, 73%).

$^1$H NMR (400 MHz, CD$_3$OD) δ 7.92 (2H, d, J=8.8 Hz), 7.54 (2H, d, J=8.8 Hz), 7.49 (1H, d, J=3.6 Hz), 6.89 (1H, d, J=3.6 Hz), 4.56 (1H, dd, J=6.8, 5.0 Hz), 4.50 (2H, br s), 4.21 (1H, br s), 4.16 (1H, dd, J=5.7, 4.4 Hz), 3.67 (1H, br s), 2.95 (1H, dd, J=18.1, 5.7 Hz), 2.85 (1H, dd, J=18.1, 4.4 Hz), 2.49 (1H, br s), 2.15 (1H, br s), 1.99-2.07 (2H, m), 1.45 (9H, s), 1.44 (9H, s).

MS (ESI) m/z 585 (M+H)$^+$

Step 2. Synthesis of N—(N-{[5-(4-amidinophenoxycarbonyl)furan-2-yl]methyl}-D-prolyl)-L-aspartic acid bis(trifluoroacetate) (A-3)

To the compound (51 mg, 0.040 mmol) obtained in step 1 was added trifluoroacetic acid (1 mL), and the mixture was stirred at room temperature for 2 hours. The reaction mixture was concentrated under reduced pressure and the obtained residue was purified by high performance liquid chromatography (water-acetonitrile, each containing 0.1% trifluoroacetic acid) to give the title compound (21 mg, 0.030 mmol, 48%).

$^1$H NMR (400 MHz, D$_2$O) δ 7.84 (2H, d, J=8.9 Hz), 7.46 (1H, d, J=3.6 Hz), 7.44 (2H, d, J=8.9 Hz), 6.88 (1H, d, J=3.6 Hz), 4.73 (1H, d, J=14.3 Hz), 4.53 (1H, d, J=14.3 Hz), 4.52 (1H, dd, J=7.5, 4.9 Hz), 4.42 (1H, dd, J=9.5, 6.8 Hz), 3.79-3.85 (1H, m), 3.36-3.43 (1H, m), 2.86 (1H, dd, J=16.9, 4.9 Hz), 2.74 (1H, dd, J=16.9, 7.5 Hz), 2.49-2.56 (1H, m), 2.14-2.22 (1H, m), 1.95-2.06 (2H, m).

MS (ESI) m/z 473 (M+H)$^+$

Example 9

Synthesis of N—(N-{[5-(4-amidinophenoxycarbonyl)furan-2-yl]methyl}-D-prolyl)-D-aspartic acid bis(trifluoroacetate) (A-4)

Step 1. Synthesis of N—(N-{[5-(4-amidinophenoxycarbonyl)furan-2-yl]methyl}-D-prolyl)-D-aspartic acid dimethyl ester bis(trifluoroacetate)

Using D-aspartic acid dimethyl ester hydrochloride instead of L-aspartic acid di-tert-butyl ester hydrochloride and by an operation similar to that in, Example 8, step 1, the title compound was obtained.

MS (ESI) m/z 501 (M+H)$^+$

Step 2. Synthesis of N—(N-{[5-(4-amidinophenoxycarbonyl)furan-2-yl]methyl}-D-prolyl)-D-aspartic acid bis(trifluoroacetate) (A-4)

To the compound obtained in step 1 were added 4N hydrochloric acid in 1,4-dioxane and water (1/1), and the mixture was stirred at 60° C. for 3 hours. The reaction mixture was concentrated under reduced pressure and the obtained residue was purified by high performance liquid chromatography (water-acetonitrile, each containing 0.1% trifluoroacetic acid) to give the title compound (2 steps yield 5%).

$^1$H NMR (400 MHz, D$_2$O) δ 7.85 (2H, d, J=8.8 Hz), 7.49 (1H, J=3.6 Hz), 7.45 (2H, d, J=8.8 Hz), 6.87 (1H, d, J=3.6 Hz), 4.68 (1H, d, J=14.6 Hz), 4.51 (1H, d, J=14.6 Hz), 4.49 (1H, dd, J=6.4, 5.0 Hz), 4.42 (1H, dd, J=9.5, 6.9 Hz), 3.81-3.86 (1H, m), 3.36-3.43 (1H, m), 2.79 (1H, dd, J=17.2, 6.5 Hz), 2.69 (1H, dd, J=17.2, 5.0 Hz), 2.52-2.62 (1H, m), 1.97-2.22 (3H, m).

MS (ESI) m/z 473 (M+H)$^+$

Example 10

Synthesis of N-{[5-(4-amidinophenoxycarbonyl)furan-2-yl]methyl}-N-methylglycine bis(trifluoroacetate) (A-12)

Step 1. Synthesis of N-[(5-ethoxycarbonylfuran-2-yl)methyl]-N-methylglycine tert-butyl ester trifluoroacetate Sarcosine tert-butyl ester hydrochloride (3.5 g, 19 mmol) was dissolved in tetrahydrofuran (30 ml) and acetonitrile (10 ml). 5-Chloromethylfuran-2-carboxylic acid ethyl ester (1.0 mL, 6.5 mmol) and N,N-diisopropylethylamine (5.7 mL, 32 mmol) were added, and the mixture was stirred at room temperature overnight. The reaction mixture was concentrated under reduced pressure, ethyl acetate was added to the obtained residue, and the mixture was washed successively with saturated aqueous sodium hydrogen carbonate and saturated brine. The organic layer was dried over anhydrous sodium sulfate, and concentrated under reduced pressure and the obtained residue was purified by high performance liquid chromatography (water-acetonitrile, each containing 0.1% trifluoroacetic acid) to give the title compound (2.1 g, 5.2 mmol, 79%).

MS (ESI) m/z 298 (M+H)$^+$

Step 2. Synthesis of 5-[N-(tert-butoxycarbonylmethyl)-N-methylamino]methylfuran-2-carboxylic acid The compound (2.1 g, 5.2 mmol) obtained in step 1 was dissolved in tetrahydrofuran (60 ml) and water (20 ml). 1N Aqueous sodium hydroxide solution (13 mL, 13 mmol) and ethanol (5 mL) were added, and the mixture was stirred at room temperature overnight. 1N Hydrochloric acid (2.6 mL) was added to the reaction mixture, and the mixture was extracted 3 times with dichloromethane. Furthermore, to the aqueous layer was added 1N hydrochloric acid (5.2 mL), and the mixture was extracted 5 times with ethyl acetate. The dichloromethane layer and ethyl acetate layer were combined, dried over anhydrous sodium sulfate, and concentrated under reduced pressure. Ethyl acetate and diethyl ether were added to the obtained residue, and the precipitated solid was collected by filtration to give the title compound (1.3 g, 4.8 mmol, 94%).

MS (ESI) m/z 270 (M+H)$^+$

Step 3. Synthesis of N-{[5-(4-amidinophenoxycarbonyl)furan-2-yl]methyl}-N-methylglycine bis(trifluoroacetate) (A-12)

Using the compound (0.50 g, 1.9 mmol) obtained in step 2 and by an operation similar to that in Example 7, step 2, the title compound (1.0 g, 1.8 mmol, 96%) was obtained.

$^1$H NMR (400 MHz, D$_2$O) δ 7.85 (2H, d, J=8.9 Hz), 7.53 (1H, d, J=3.6 Hz), 7.44 (2H, d, J=8.9 Hz), 6.93 (1H, d, J=3.6 Hz), 4.54 (2H, s), 3.79 (2H, s), 2.93 (3H, s).

MS (ESI) m/z 332 (M+H)$^+$

Example 11

Synthesis of N—(N-{[5-(4-amidinophenoxycarbonyl)furan-2-yl]methyl}-N-methyl-L-valyl)-L-aspartic acid bis(trifluoroacetate) (A-14)

Step 1. Synthesis of N—[N-(benzyloxycarbonyl)-N-methylvalyl]-L-aspartic acid di-tert-butyl ester To N-benzyloxycarbonyl-N-methyl-L-valine (0.50 g, 1.9 mmol), L-aspartic acid di-tert-butyl ester hydrochloride (0.53 g, 1.9 mmol), WSC hydrochloride (0.43 g, 2.3 mmol), and 1-hydroxybenzotriazole monohydrate (0.35 g, 2.3 mmol) were added tetrahydrofuran (10 ml) and triethylamine (0.39 mL, 2.8 mmol), and the mixture was stirred at room temperature for 5 hours. The reaction mixture was concentrated under reduced pressure and the obtained residue was purified by silica gel column chromatography (hexane/ethyl acetate=80/20) to give the title compound (0.91 g, 1.8 mmol, 98%).

$^1$H NMR (400 MHz, CDCl$_3$) δ 7.29-7.39 (5H, m), 6.63-6.84 (1H, br), 5.10-5.18 (2H, m), 4.62-4.67 (1H, m), 4.18 (1H, d, J=9.0 Hz), 2.89 (3H, s), 2.83 (1H, dd, J=16.9, 4.8 Hz), 2.62-2.68 (1H, m), 2.25-2.29 (1H, m), 1.45 (9H, s), 1.42 (9H, s), 0.99 (3H, d, J=6.0 Hz), 0.87 (3H, d, J=7.0 Hz).

MS (ESI) m/z 493 (M+H)$^+$

Step 2. Synthesis of N—(N-methyl-L-valyl)-L-aspartic acid di-tert-butyl ester

To a solution of the compound (0.91 g, 1.8 mmol) obtained in step 1 in ethanol (40 ml) was added a catalytic amount of 10% palladium/carbon, and the mixture was stirred for 3 hours under a hydrogen atmosphere. The catalyst was filtered off, and the filtrate was concentrated under reduced pressure to give the title compound (0.66 g, 1.8 mmol, 99%).

MS (ESI) m/z 359 (M+H)$^+$

Step 3. Synthesis of N—{N-[(5-carboxyfuran-2-yl)methyl]-N-methyl-L-valyl}-L-aspartic acid di-tert-butyl ester trifluoroacetate The compound (0.23 g, 0.65 mmol) obtained in step 2 was dissolved in acetonitrile (3 mL). 5-Chloromethylfuran-2-carboxylic acid ethyl ester (0.10 mL, 0.65 mmol) and N,N-diisopropylethylamine (0.11 mL, 0.65 mmol) were added, and the mixture was stirred at room temperature overnight. A catalytic amount of lithium iodide was added to the reaction mixture, and the mixture was further stirred overnight. The reaction mixture was concentrated under reduced pressure, and the obtained residue was dissolved in tetrahydrofuran (3 mL). 1N Aqueous sodium hydroxide solution (1.6 mL, 1.6 mmol), water (0.5 mL) and methanol (1.5 mL) were added, and the mixture was stirred at room temperature overnight. 1N Hydrochloric acid (1.6 mL, 1.6 mmol) was added to the reaction mixture, the mixture was concentrated under reduced pressure and the obtained residue was purified by high performance liquid chromatography (water-acetonitrile, each containing 0.1% trifluoroacetic acid) to give the title compound (0.17 g, 0.29 mmol, 45%).
MS (ESI) m/z 483 (M+H)$^+$ Step 4. Synthesis of N—(N-{[5-(4-amidinophenoxycarbonyl)furan-2-yl]methyl}-N-methyl-L-valyl)-L-aspartic acid bis(trifluoroacetate) (A-14)

Using the compound (30 mg, 0.050 mmol) obtained in step 3 and by an operation similar to that in Example 7, step 2, the title compound (23 mg, 0.032 mmol, 63%) was obtained.
$^1$H NMR (400 MHz, D$_2$O) δ 7.84 (2H, d, J=8.8 Hz), 7.55 (1H, d, J=3.6 Hz), 7.44 (2H, d, J=8.8 Hz), 6.95 (1H, d, J=3.6 Hz), 4.75 (1H, dd, J=10.3, 4.6 Hz), 4.57 (1H, d, J=15.0 Hz), 4.47 (1H, d, J=15.0 Hz), 3.77 (1H, d, J=5.3 Hz), 2.99 (1H, dd, J=17.0, 4.6 Hz), 2.90 (3H, s), 2.86 (1H, dd, J=17.0, 10.3 Hz), 2.46-2.51 (1H, m), 1.08 (3H, d, J=6.9 Hz), 0.96 (3H, d, J=6.7 Hz).
MS (ESI) m/z 489 (M+H)$^+$ Example 12

Synthesis of N—[(N-{[5-(4-amidinophenoxycarbonyl)furan-2-yl]methyl}-1,2,3,4-tetrahydroisoquinolin-3-yl)carbonyl]-L-aspartic acid bis(trifluoroacetate) (A-18)

Step 1. Synthesis of N-[(5-ethoxycarbonylfuran-2-yl)methyl]-1,2,3,4-tetrahydroisoquinoline-3-carboxylic acid benzyl ester To a solution of 1,2,3,4-tetrahydroisoquinolinecarboxylic acid benzyl ester p-toluenesulfonate (2.1 g, 4.9 mmol) in acetonitrile (15 mL) were added 5-chloromethylfuran-2-carboxylic acid ethyl ester (0.50 mL, 3.3 mmol) and N,N-diisopropylethylamine (1.4 mL, 8.1 mmol), and the mixture was stirred at room temperature for 20 hours. The reaction mixture was concentrated under reduced pressure, and the obtained residue was dissolved in ethyl acetate, and washed successively with saturated aqueous sodium hydrogen carbonate and saturated brine. The organic layer was dried over anhydrous sodium sulfate, and concentrated under reduced pressure and the obtained residue was purified by silica gel column chromatography (hexane/ethyl acetate=92/8) to give the title compound (1.1 g, 2.6 mmol, 81%).
$^1$H NMR (400 MHz, CDCl$_3$) δ 7.28-7.32 (3H, m), 7.19-7.21 (2H, m), 7.07-7.14 (4H, m), 6.98-7.00 (1H, m), 6.33 (1H, d, J=3.4 Hz), 5.11 (2H, s), 4.34 (2H, q, J=7.1 Hz), 4.10 (1H, d, J=15.2 Hz), 4.07 (1H, d, J=15.0 Hz), 4.01 (1H, d, J=15.0 Hz), 3.90 (1H, d, J=15.2 Hz), 3.84 (1H, dd, J=5.9, 4.0 Hz), 3.24 (1H, dd, J=16.2, 5.9 Hz), 3.14 (1H, dd, J=16.2, 4.0 Hz), 1.36 (3H, t, J=7.1 Hz).
MS (ESI) m/z 420 (M+H)$^+$ Step 2. Synthesis of N-[(5-ethoxycarbonylfuran-2-yl)methyl]-1,2,3,4-tetrahydroisoquinoline-3-carboxylic acid trifluoroacetate To a solution of the compound (1.1 g, 2.6 mmol) obtained in step 1 in tetrahydrofuran (10 ml) was added a catalytic amount of 10% palladium/carbon, and the mixture was stirred under a hydrogen atmosphere at room temperature for 4 hours. The catalyst was removed by filtration, and the obtained filtrate was concentrated under reduced pressure. The obtained residue was purified by high performance liquid chromatography (water-acetonitrile, each containing 0.1% trifluoroacetic acid) to give the title compound (0.74 g, 1.7 mmol, 64%).
MS (ESI) m/z 330 (M+H)$^+$ Step 3. Synthesis of N-[(5-carboxyfuran-2-yl)methyl]-1,2,3,4-tetrahydroisoquinoline-3-carbonyl-L-aspartic acid di-tert-butyl ester trifluoroacetate To a solution of the compound (0.20 g, 0.45 mmol) obtained in step 2 in tetrahydrofuran (2.5 mL) were added L-aspartic acid di-tert-butyl ester hydrochloride (0.13 g, 0.45 mmol), WSC hydrochloride (0.10 g, 0.54 mmol), 1-hydroxybenzotriazole monohydrate (69 mg, 0.45 mmol), and N,N-diisopropylethylamine (0.086 mL, 0.50 mmol), and the mixture was stirred at room temperature for 16 hours. The reaction mixture was concentrated under reduced pressure and the obtained residue was dissolved in ethyl acetate, and washed successively with saturated aqueous sodium hydrogen carbonate and saturated brine. The organic layer was dried over anhydrous sodium sulfate, and concentrated under reduced pressure. Tetrahydrofuran (2.5 mL) and 1N aqueous sodium hydroxide solution (0.50 mL, 0.50 mmol) were added to the obtained residue, and the mixture was stirred at room temperature for 5 hours. 1N Hydrochloric acid (0.50 mL, 0.50 mmol) was added to the reaction mixture, the mixture was concentrated under reduced pressure, and the obtained residue was purified by high performance liquid chromatography (water-acetonitrile, each containing 0.1% trifluoroacetic acid) to give the title compound (35 mg, 0.054 mmol, 12%).
MS (ESI) m/z 529 (M+H)$^+$ Step 4. Synthesis of N—[(N-{[5-(4-amidinophenoxycarbonyl)furan-2-yl]methyl}-1,2,3,4-tetrahydroisoquinolin-3-yl)carbonyl]-L-aspartic acid bis(trifluoroacetate) (A-18)

Using the compound (35 mg, 0.054 mmol) obtained in step 3 and by an operation similar to that in Example 7, step 2, the title compound (31 mg, 0.041 mmol, 76%) was obtained.
MS (ESI) m/z 535 (M+H)$^+$ Example 13

Synthesis of N-{[5-(4-amidinophenoxycarbonyl)furan-2-yl]methyl}-1H-pyrrole-2-carboxylic acid trifluoroacetate (A-19)

Step 1. Synthesis of 1-{[5-(ethoxycarbonyl)furan-2-yl]methyl}-pyrrole-2-carboxylic acid benzyl ester Using 5-chloromethyl-2-furancarboxylic acid ethyl ester (0.300 mL, 1.97 mmol) instead of M-6 and by an operation similar to that in Example 20, step 1, the title compound (416 mg, 1.18 mmol, 60%) was obtained.
$^1$H NMR (400 MHz, CDCl$_3$) δ 7.45-7.29 (5H, m), 7.07-7.01 (2H, m), 6.99-6.94 (1H, m), 6.26 (1H, d, J=3.7 Hz), 6.17 (1H, dd, J=3.7, 2.6 Hz), 5.59 (2H, s), 5.27 (2H, s), 4.34 (2H, q, J=7.1 Hz), 1.36 (3H, t, J=7.1 Hz).
MS (ESI) m/z 354 (M+H)$^+$

Step 2. Synthesis of 1-[(5-carboxyfuran-2-yl)methyl]-pyrrole-2-carboxylic acid benzyl ester To a solution of the compound (416 mg, 1.18 mmol) obtained in step 1 in ethanol (3.0 ml) was added 1N aqueous sodium hydroxide solution (1.24 mL, 1.24 mmol), and the mixture was stirred at room temperature overnight. 1N Hydrochloric acid (1.24 mL) was added to the reaction mixture, the mixture was concentrated under reduced pressure and the obtained residue was purified by high performance liquid chromatography (water-acetonitrile, each containing 0.1% trifluoroacetic acid) to give the title compound (76 mg, 0.23 mmol, 20%).

$^1$H NMR (400 MHz, DMSO-$d_6$) δ 7.44-7.30 (5H, m), 7.28 (1H, dd, J=2.6, 1.8 Hz), 7.11 (1H, d, J=3.4 Hz), 6.95 (1H, dd, J=3.9, 1.8 Hz), 6.28 (1H, d, J=3.4 Hz), 6.20 (1H, dd, J=3.9, 2.6 Hz), 5.61 (2H, s), 5.25 (2H, s).

MS (ESI) m/z 326 (M+H)$^+$

Step 3. Synthesis of N-{[5-(4-amidinophenoxycarbonyl)furan-2-yl]methyl}-1H-pyrrole-2-carboxylic acid trifluoroacetate (A-19)

The compound (31 mg, 0.094 mmol) obtained in step 2, 4-amidinophenol hydrochloride (19 mg, 0.11 mmol), and WSC hydrochloride (22 mg, 0.11 mmol) were dissolved in pyridine (0.5 mL), and the mixture was stirred at room temperature for 3 hours. The reaction mixture was concentrated under reduced pressure. To a solution of the obtained residue in ethanol (0.5 mL)/chloroform (0.1 mL) was added a catalytic amount of 10% palladium/carbon, and the mixture was stirred at room temperature for 9 hours under a hydrogen atmosphere. The catalyst was filtered off, the filtrate was concentrated under reduced pressure, and the obtained residue was purified by high performance liquid chromatography (water-acetonitrile, each containing 0.1% trifluoroacetic acid) to give the title compound (7.4 mg, 0.016 mmol, 17%).

$^1$H NMR (400 MHz, DMSO-$d_6$) δ 9.45-9.24 (2H, br), 9.12-8.93 (2H, br), 7.89 (2H, d, J=8.8 Hz), 7.55 (2H, d, J=8.8 Hz), 7.54 (1H, d, J=3.5 Hz), 7.24 (1H, dd, J=2.6, 1.8 Hz), 6.87 (1H, dd, J=3.9, 1.8 Hz), 6.45 (1H, d, J=3.5 Hz), 6.18 (1H, dd, J=3.9, 2.6 Hz), 5.70 (2H, s).

MS (ESI) m/z 354 (M+H)$^+$

Example 14

Synthesis of N-{[5-(4-amidinophenoxycarbonyl)thiophen-2-yl]methyl}-L-proline bis(trifluoroacetate) (B-1)

Step 1. Synthesis of N-[(5-tert-butoxycarbonylthiophen-2-yl)methyl]-L-proline methyl ester To a solution of M-6 (0.51 g, 2.2 mmol) in acetonitrile (9 mL) were added L-proline methyl ester hydrochloride (0.36 g, 2.2 mmol), lithium iodide (59 mg, 0.44 mmol), and N,N-diisopropylethylamine (0.76 mL, 4.4 mmol), and the mixture was stirred at room temperature overnight. The reaction mixture was filtered, and concentrated under reduced pressure and the obtained residue was purified by silica gel column chromatography (hexane/ethyl acetate=85/15) to give the title compound (0.55 g, 1.7 mmol, 77%).

$^1$H NMR (400 MHz, CDCl$_3$) δ 7.57 (1H, d, J=3.7 Hz), 6.87 (1H, d, J=3.7 Hz), 4.09 (1H, d, J=14.3 Hz), 3.87 (1H, d, J=14.3 Hz), 3.71 (3H, s), 3.35 (1H, dd, J=8.8, 5.8 Hz), 3.10 (1H, ddd, J=8.7, 7.8, 3.5 Hz), 2.54 (1H, ddd, J=8.7, 8.0, 7.7 Hz), 1.75-2.18 (4H, m), 1.56 (9H, s).

MS (ESI) m/z 326 (M+H)$^+$

Step 2. Synthesis of N-{[5-(4-amidinophenoxycarbonyl)thiophen-2-yl]methyl}-L-proline methyl ester bis(trifluoroacetate)

To the compound (0.55 g, 1.7 mmol) obtained in step 1 was added trifluoroacetic acid (10 ml), and the mixture was stirred at room temperature for 1 hour. The reaction mixture was concentrated under reduced pressure, pyridine (10 ml), 4-hydroxybenzamidine hydrochloride (0.35 g, 2.0 mmol), and WSC hydrochloride (0.48 g, 2.5 mmol) were added to the obtained residue, and the mixture was stirred at room temperature overnight. The reaction mixture was concentrated under reduced pressure and the obtained residue was purified by high performance liquid chromatography (water-acetonitrile, each containing 0.1% trifluoroacetic acid) to give the title compound (0.30 g, 0.49 mmol, 29%).

MS (ESI) m/z 388 (M+H)$^+$

Step 3. Synthesis of N-{[5-(4-amidinophenoxycarbonyl)thiophen-2-yl]methyl}-L-proline bis(trifluoroacetate) (B-1)

To the compound (0.30 g, 0.49 mmol) obtained in step 2 was added 4N hydrochloric acid (5 mL), and the mixture was stirred at 60° C. for 5 hours. Then, 1,4-dioxane (5 mL) was added to the reaction mixture, and the mixture was stirred at 55° C. for 15 hours. The reaction mixture was concentrated under reduced pressure and the obtained residue was purified by high performance liquid chromatography (water-acetonitrile, each containing 0.1% trifluoroacetic acid) to give the title compound (0.12 g, 0.20 mmol, 41%).

$^1$H NMR (400 MHz, D$_2$O) δ 7.95 (1H, d, J=3.9 Hz), 7.84 (2H, d, J=8.9 Hz), 7.44 (2H, d, J=8.9 Hz), 7.38 (1H, d, J=3.9 Hz), 4.67 (2H, s), 4.07 (1H, dd, J=9.6, 6.4 Hz), 3.71-3.77 (1H, m), 3.28-3.35 (1H, m), 2.41-2.50 (1H, m), 1.90-2.16 (3H, m).

MS (ESI) m/z 374 (M+H)$^+$

Example 15

Synthesis of N—(N-{[5-(4-amidinophenoxycarbonyl)thiophen-2-yl]methyl}-L-pipecolinyl)-L-aspartic acid bis(trifluoroacetate) (B-17)

Step 1. Synthesis of N—(N-{[5-(tert-butoxycarbonyl)thiophen-2-yl]methyl}-L-pipecolinyl)-L-aspartic acid dimethyl ester trifluoroacetate L-Pipecolinic acid (0.28 g, 2.1 mmol) was dissolved in acetonitrile (8 mL). M-6 (0.50 g, 2.1 mmol), N,N-diisopropylethylamine (0.37 mL, 2.1 mmol), and lithium iodide (0.058 g, 0.43 mmol) were added, and the mixture was stirred at room temperature for 14 hours. The reaction mixture was concentrated under reduced pressure, L-aspartic acid dimethyl ester hydrochloride (0.85 g, 4.3 mmol), WSC hydrochloride (0.82 g, 4.3 mmol), and pyridine (5 mL) were added to the obtained residue, and the mixture was stirred at room temperature overnight. The reaction mixture was concentrated under reduced pressure and the obtained residue was purified by high performance liquid chromatography (water-acetonitrile, each containing 0.1% trifluoroacetic acid) to give the title compound (0.17 g, 0.29 mmol, 14%).

MS (ESI) m/z 469 (M+H)+

Step 2. Synthesis of N—{N-[(5-carboxythiophen-2-yl)methyl]-L-pipecolinyl}-L-aspartic acid dimethyl ester trifluoroacetate To the compound (0.17 g, 0.29 mmol) obtained in step 1 was added trifluoroacetic acid (3 mL), and the mixture was stirred at room temperature for 3 hours. The reaction mixture was concentrated under reduced pressure, water was added to the obtained residue, and the mixture was lyophilized to give the title compound (0.15 g, 0.28 mmol, 95%).

MS (ESI) m/z 413 (M+H)+

Step 3. Synthesis of N—(N-{[5-(4-amidinophenoxycarbonyl)thiophen-2-yl]methyl}-L-pipecolinyl)-L-aspartic acid dimethyl ester bis(trifluoroacetate)

To the compound (73 mg, 0.14 mmol) obtained in step 2 were added 4-amidinophenol hydrochloride (33 mg, 0.19 mmol), WSC hydrochloride (42 mg, 0.22 mmol), and pyridine (3 mL), and the mixture was stirred at room temperature for 15 hours. The reaction mixture was concentrated under reduced pressure and the obtained residue was purified by high performance liquid chromatography (water-acetonitrile, each containing 0.1% trifluoroacetic acid) to give the title compound (53 mg, 0.070 mmol, 50%).

MS (ESI) m/z 531 (M+H)+

Step 4. Synthesis of N—(N-{[5-(4-amidinophenoxycarbonyl)thiophen-2-yl]methyl}-L-pipecolinyl)-L-aspartic acid bis(trifluoroacetate) (B-17)

To the compound (53 mg, 0.070 mmol) obtained in step 3 were added 4N hydrochloric acid (2 mL) and 1,4-dioxane (2 mL), and the mixture was stirred at 50° C. for 5 hours. The reaction mixture was concentrated under reduced pressure and the obtained residue was purified by high performance liquid chromatography (water-acetonitrile, each containing 0.1% trifluoroacetic acid) to give the title compound (26 mg, 0.036 mmol, 51%).

$^1$H NMR (400 MHz, D$_2$O) δ 7.99 (1H, d, J=3.9 Hz), 7.85 (2H, d, J=8.8 Hz), 7.45 (2H, d, J=8.8 Hz), 7.36 (1H, d, J=3.9 Hz), 4.67 (1H, dd, J=8.1, 4.5 Hz), 4.59 (1H, d, J=14.3 Hz), 4.51 (1H, d, J=14.3 Hz), 3.90 (1H, dd, J=11.9, 3.4 Hz), 3.62 (1H, br d, J=11.3 Hz), 3.14 (1H, br dd, J=12.8, 9.8 Hz), 2.95 (1H, dd, J=16.8, 4.5 Hz), 2.83 (1H, dd, J=16.8, 8.1 Hz), 2.22 (1H, br d, J=13.4 Hz), 1.68-1.92 (4H, m), 1.46-1.51 (1H, m).

MS (ESI) m/z 503 (M+H)+

Example 16

Synthesis of N—(N-{[5-(4-amidinophenoxycarbonyl)thiophen-2-yl]methyl}-N-methyl-L-valyl)-L-aspartic acid bis(trifluoroacetate) (B-22)

Step 1. Synthesis of N—(N-methyl-L-valyl)-L-aspartic acid dimethyl ester

Using L-aspartic acid dimethyl ester hydrochloride instead of L-aspartic acid di-tert-butyl ester hydrochloride and by an operation similar to that in Example 11, steps 1 and 2, the title compound was obtained (yield 41%).

MS (ESI) m/z 275 (M+H)+

Step 2. Synthesis of N—[N-{(5-tert-butoxycarbonylthiophen-2-yl)methyl}-N-methyl-L-valyl]-L-aspartic acid dimethyl ester The compound (0.90 g, 3.9 mmol) obtained in step 1 was dissolved in acetonitrile (15 mL). M-6 (1.1 g, 3.9 mmol), N,N-diisopropylethylamine (0.67 mL, 3.9 mmol), and lithium iodide (0.10 g, 0.77 mmol) were added, and the mixture was stirred at 35° C. for 3 hours. The reaction mixture was concentrated under reduced pressure, and the obtained residue was dissolved in ethyl acetate and washed successively with saturated aqueous sodium hydrogen carbonate and saturated brine. The organic layer was dried over anhydrous sodium sulfate and concentrated under reduced pressure. Acetonitrile (15 mL), lithium iodide (0.10 g, 0.77 mmol), and N,N-diisopropylethylamine (0.67 mL, 3.9 mmol) were added to the obtained residue, and the mixture was stirred at 35° C. for 2 hours. N,N-Diisopropylethylamine (0.67 mL, 3.9 mmol) was further added to the reaction mixture, and the mixture was stirred at 35° C. for 13 hours. The reaction mixture was concentrated under reduced pressure and the obtained residue was purified by silica gel column chromatography (hexane/ethyl acetate=75/25) to give the title compound (1.6 g, 3.4 mmol, 87%).

$^1$H NMR (400 MHz, CDCl$_3$) δ 7.57 (1H, d, J=3.7 Hz), 6.89 (1H, d, J=3.7 Hz), 6.89 (1H, d, J=3.6 Hz), 4.92 (1H, ddd, J=4.8, 4.5, 3.6 Hz), 3.95 (1H, d, J=14.7 Hz), 3.73 (3H, s), 3.71 (3H, s), 3.66 (1H, d, J=14.7 Hz), 3.08 (1H, dd, J=17.1, 4.8 Hz), 2.89 (1H, dd, J=17.1, 4.5 Hz), 2.71 (1H, d, J=8.2 Hz), 2.29 (3H, s), 2.14-2.19 (1H, m), 1.57 (9H, s), 1.06 (3H, d, J=6.7 Hz), 0.91 (3H, d, J=6.6 Hz).

MS (ESI) m/z 471 (M+H)+

Step 3. Synthesis of N—{N-[(5-carboxythiophen-2-yl)methyl]-N-methyl-L-valyl}-L-aspartic acid dimethyl ester To the compound (1.6 g, 3.4 mmol) obtained in step 2 was added trifluoroacetic acid (10 ml), and the mixture was stirred at room temperature for 30 minutes, and concentrated under reduced pressure to give a crude product (2.45 g) containing the title compound.

MS (ESI) m/z 415 (M+H)+

Step 4. Synthesis of N—(N-{[5-(4-amidinophenoxycarbonyl)thiophen-2-yl]methyl}-N-methyl-L-valyl)-L-aspartic acid bis(trifluoroacetate) (B-22)

To the crude product (1.2 g) obtained in step 3, 4-amidinophenol hydrochloride (0.30 g, 1.7 mmol), and WSC hydrochloride (0.33 g, 1.7 mmol) was added pyridine (17 mL), and the mixture was stirred at 30° C. for 1 hour. 4-Amidinophenol hydrochloride (0.30 g, 1.7 mmol) and WSC hydrochloride (0.33 g, 1.7 mmol) were added to the reaction mixture, and the mixture was further stirred at 30° C. for 15 hours. The reaction mixture was concentrated under reduced pressure, 4N hydrochloric acid (8 mL) and 1,4-dioxane (8 mL) were added to the obtained residue, and the mixture was stirred at 55° C. overnight. The reaction mixture was concentrated under reduced pressure and the obtained residue was purified by high performance liquid chromatography (water-acetonitrile, each containing 0.1% trifluoroacetic acid) to give the title compound (0.60 g, 0.82 mmol, 2 steps yield 48%).

¹H NMR (400 MHz, D₂O) δ 8.00 (1H, d, J=3.9 Hz), 7.85 (2H, d, J=8.8 Hz), 7.45 (2H, d, J=8.8 Hz), 7.41 (1H, d, J=3.9 Hz), 4.72-4.79 (1H, m), 4.69 (1H, d, J=14.6 Hz), 4.60 (1H, d, J=14.6 Hz), 3.79 (1H, d, J=5.3 Hz), 3.02 (1H, dd, J=17.3, 4.4 Hz), 2.90 (3H, s), 2.89 (1H, dd, J=17.3, 8.3 Hz), 2.45-2.50 (1H, m), 1.10 (3H, d, J=6.8 Hz), 0.96 (3H, d, J=6.7 Hz).

MS (ESI) m/z 505 (M+H)⁺

Example 17

Synthesis of N—(N-{[5-(4-amidino-2-fluorophenoxycarbonyl)thiophen-2-yl]methyl}-N-methyl-D-valyl)-L-aspartic acid bis(trifluoroacetate) (B-27)

Step 1. Synthesis of N—{N-[(5-tert-butoxycarbonylthiophen-2-yl)methyl]-N-methyl-D-valyl}-L-aspartic acid dimethyl ester N-(D-Valyl)-L-aspartic acid dimethyl ester (1.2 g, 4.6 mmol), M-6 (1.1 g, 4.6 mmol), and N,N-diisopropylethylamine (2.0 mL, 12 mmol) were dissolved in acetonitrile (80 ml), sodium iodide (0.76 g, 5.1 mmol) was added, and the mixture was stirred at 60° C. for 2 hours. The reaction mixture was concentrated under reduced pressure, ethyl acetate was added to the obtained residue, and the mixture was washed successively with saturated aqueous sodium hydrogen carbonate and saturated brine. The organic layer was dried over anhydrous sodium sulfate, and concentrated under reduced pressure. N,N-Dimethylformamide (50 ml), potassium carbonate (0.70 g, 5.1 mmol), and methyl iodide (0.37 mL, 6.0 mmol) were added to the obtained residue, and the mixture was stirred at 60° C. for 3 hours. The reaction mixture was concentrated under reduced pressure, ethyl acetate was added to the obtained residue, and the mixture was washed successively with saturated aqueous sodium hydrogen carbonate and saturated brine. The organic layer was dried over anhydrous sodium sulfate, and concentrated under reduced pressure. The obtained residue was purified by silica gel column chromatography (hexane/ethyl acetate) to give the title compound (0.68 g, 1.4 mmol, 31%).

¹H NMR (CDCl₃, 400 MHz) δ 7.57 (1H, d, J=3.7 Hz), 6.93 (1H, d, J=3.7 Hz), 6.76 (1H, d, J=8.3 Hz), 5.05-4.81 (1H, m), 3.94 (1H, d, J=14.8 Hz), 3.79 (3H, s), 3.75 (1H, d, J=14.8 Hz), 3.68 (3H, s), 3.06 (1H, dd, J=17.2, 4.8 Hz), 2.83 (1H, dd, J=17.2, 4.5 Hz), 2.67 (1H, d, J=8.8 Hz), 2.34 (3H, s), 2.22-2.10 (1H, m), 1.57 (9H, s), 1.06 (3H, d, J=6.7 Hz), 0.91 (3H, d, J=6.6 Hz).

MS (ESI) m/z 471 (M+H)⁺

Step 2. Synthesis of N—(N-{[5-(4-amidino-2-fluorophenoxycarbonyl)thiophen-2-yl]methyl}-N-methyl-D-valyl)-L-aspartic acid bis(trifluoroacetate) (B-27)

Using the compound obtained in step 1 and M-1 and by an operation similar to that in Example 16, steps 3 and 4, the title compound was obtained.

¹H NMR (400 MHz, D₂O) δ 8.04 (1H, d, J=4.0 Hz), 7.73 (1H, dd, J=10.2, 2.1 Hz), 7.69-7.62 (1H, m), 7.60-7.50 (1H, m), 7.49 (1H, d, J=4.0 Hz), 4.81-4.74 (1H, m), 4.70 (2H, s), 3.80 (1H, d, J=5.5 Hz), 3.06-2.95 (1H, m), 2.94 (3H, s), 2.87 (1H, dd, J=17.1, 8.4 Hz), 2.51-2.40 (1H, m), 1.02 (3H, d, J=6.8 Hz), 0.94 (3H, d, J=6.7 Hz).

MS (ESI) m/z 523 (M+H)⁺

Example 18

Synthesis of N—(N-{[5-(4-amidinophenoxycarbonyl)thiophen-2-yl]methyl}-N-methyl-L-leucyl)-L-aspartic acid bis(trifluoroacetate) (B-34)

Step 1. Synthesis of N-[(5-tert-butoxycarbonylthiophen-2-yl)methyl]-N-methyl-L-leucine methyl ester L-leucine methyl ester hydrochloride (0.84 g, 4.6 mmol) was dissolved in acetonitrile (80 ml). M-6 (1.1 g, 4.6 mmol), N,N-diisopropylethylamine (2.0 mL, 12 mmol), and sodium iodide (0.76 g, 5.1 mmol) were added, and the mixture was stirred at 60° C. for 2 hours. The reaction mixture was concentrated under reduced pressure, ethyl acetate was added to the obtained residue, and the mixture was washed successively with saturated aqueous sodium hydrogen carbonate and saturated brine. The organic layer was dried over anhydrous sodium sulfate, and concentrated under reduced pressure. N,N-Dimethylformamide (50 ml), potassium carbonate (0.67 g, 4.8 mmol), and methyl iodide (0.36 mL, 5.7 mmol) were added to the obtained residue, and the mixture was stirred at 60° C. for 3 hours. The reaction mixture was concentrated under reduced pressure, ethyl acetate was added to the obtained residue, and the mixture was washed successively with saturated aqueous sodium hydrogen carbonate and saturated brine. The organic layer was dried over anhydrous sodium sulfate, and concentrated under reduced pressure. The obtained residue was purified by silica gel column chromatography (hexane/ethyl acetate) to give the title compound (0.87 g, 2.4 mmol, 53%).

¹H NMR (CDCl₃, 400 MHz) δ 7.55 (1H, d, J=3.7 Hz), 6.86 (1H, d, J=3.7 Hz), 3.98 (1H, d, J=14.9 Hz), 3.79 (1H, d, J=14.9 Hz), 3.72 (3H, s), 3.44 (1H, dd, J=8.6, 6.8 Hz), 2.31 (3H, s), 1.87-1.72 (1H, m), 1.73-1.60 (1H, m), 1.56 (9H, s), 1.60-1.48 (1H, m), 0.94 (3H, d, J=6.7 Hz), 0.91 (3H, d, J=6.5 Hz).

MS (ESI) m/z 356 (M+H)⁺

Step 2. Synthesis of N-[(5-tert-butoxycarbonylthiophen-2-yl)methyl]-N-methyl-L-leucine lithium salt The compound (0.87 g, 2.4 mmol) obtained in step 1 was dissolved in methanol (2.7 mL) and tetrahydrofuran (5.4 mL), 1N aqueous lithium hydroxide solution (2.7 mL) was added, and the mixture was stirred overnight. The reaction mixture was concentrated under reduced pressure, water was added, and the mixture was lyophilized to give the title compound (0.83 g).

MS (ESI) m/z 342 (M+H)⁺

Step 3. Synthesis of N—{N-[(5-tert-butoxycarbonylthiophen-2-yl)methyl]-N-methyl-L-leucyl}-L-aspartic acid dimethyl ester The compound (0.20 g, 0.58 mmol) obtained in step 2, aspartic acid dimethyl ester hydrochloride (0.12 g, 0.58 mmol), WSC hydrochloride (0.17 g, 0.87 mmol), 1-hydroxybenzotriazole monohydrate (0.090 g, 0.58 mmol), and N,N-diisopropylethylamine (0.39 mL, 2.8 mmol) were dissolved in dichloromethane (5 mL), and the mixture was stirred at room temperature for 2 hours. The reaction mixture was concentrated under reduced pressure, and ethyl acetate was added. The mixture was washed with saturated aqueous sodium hydrogen carbonate and saturated brine, and dried over anhydrous sodium sulfate. The solvent was evaporated under reduced pressure and the obtained residue was purified by silica gel column chromatography (hexane/ethyl acetate) to give the title compound (0.15 g, 0.31 mmol, 53%).
$^1$H NMR (CDCl$_3$, 400 MHz) δ 7.65 (1H, d, J=8.1 Hz), 7.57 (1H, d, J=3.7 Hz), 6.91 (1H, d, J=3.7 Hz), 4.95-4.77 (1H, m), 3.87 (1H, d, J=14.5 Hz), 3.77 (3H, s), 3.75 (1H, d, J=14.5 Hz), 3.69 (3H, s), 3.28-3.15 (1H, m), 3.04 (1H, dd, J=16.9, 4.9 Hz), 2.88 (1H, dd, J=16.9, 4.7 Hz), 2.26 (3H, s), 1.81-1.62 (2H, m), 1.57 (9H, s), 1.49-1.38 (1H, m), 0.95 (3H, d, J=6.5 Hz), 0.91 (3H, d, J=6.5 Hz).
MS (ESI) m/z 485 (M+H)$^+$ Step 4. Synthesis of N—(N-{[5-(4-amidinophenoxy-carbonyl)thiophen-2-yl]methyl}-N-methyl-L-leucyl)-L-aspartic acid bis(trifluoroacetate) (B-34)

Using the compound obtained in step 3 and by an operation similar to that in Example 16, steps 3 and 4, the title compound was obtained.
$^1$H NMR (400 MHz, D$_2$O) δ 8.00 (1H, d, J=3.9 Hz), 7.84 (2H, d, J=8.9 Hz), 7.45 (2H, d, J=8.9 Hz), 7.41 (1H, d, J=3.9 Hz), 4.71 (2H, s), 4.65-4.59 (1H, m), 3.92 (1H, dd, J=10.9, 4.4 Hz), 2.97 (1H, dd, J=16.9, 4.5 Hz), 2.88 (3H, s), 2.83 (1H, dd, J=16.9, 8.8 Hz), 2.03-1.74 (2H, m), 1.62 (1H, s), 0.90 (6H, d, J=6.5 Hz).
MS (ESI) m/z 519 (M+H)$^+$ Example 19

Synthesis of N-(1-{[5-(4-amidino-2-fluorophenoxy-carbonyl)thiophen-2-yl]
methylamino}cyclopropanecarbonyl)-L-aspartic acid bis(trifluoroacetate) (B-37)

Step 1. Synthesis of 1-[(tert-butoxycarbonyl)amino] cyclopropanecarbonyl-L-aspartic acid dibenzyl ester To a solution of 1-(tert-butoxycarbonyl)aminocyclopropanecarboxylic acid (257 mg, 1.28 mmol), L-aspartic acid dibenzyl ester tosylate (806 mg, 1.66 mmol), WSC hydrochloride (367 mg, 1.92 mmol), and 1-hydroxybenzotriazole (291 mg, 1.92 mmol) in dichloromethane (4.0 ml) was added N,N-diisopropylethylamine (1.30 mL, 7.66 mmol), and the mixture was stirred at room temperature for 7 hours. 1N Hydrochloric acid was added to the reaction mixture, the mixture was extracted 3 times with dichloromethane, and the obtained dichloromethane layer was washed with saturated brine. After drying over anhydrous magnesium sulfate, the desiccant was filtered off, and the filtrate was concentrated under reduced pressure. The obtained residue was purified by silica gel column chromatography (hexane/ethyl acetate) to give the title compound (598 mg, 1.20 mmol, 94%).
$^1$H NMR (400 MHz, CDCl$_3$) δ 7.41-7.23 (10H, m), 5.14 (2H, s), 5.11-4.96 (2H, m), 4.93-4.82 (1H, m), 3.08 (1H, dd, J=17.1, 4.3 Hz), 2.92 (1H, dd, J=17.1, 3.8 Hz), 1.60-1.49 (2H, m), 1.44 (9H, s), 1.09-0.96 (2H, m).
MS (ESI) m/z 497 (M+H)$^+$ Step 2. Synthesis of N-(1-{[5-(tert-butoxycarbonyl) thiophen-2-yl]methylamino}cyclopropanecarbonyl)-L-aspartic acid dibenzyl ester The compound (598 mg, 1.20 mmol) obtained in step 1 was dissolved in trifluoroacetic acid (4.0 ml), and the mixture was stirred at room temperature for 1 hour. The reaction mixture was concentrated under reduced pressure, M-6 (302 mg, 1.19 mmol), cesium carbonate (1.07 g, 3.27 mmol), and N,N-dimethylformamide (3.5 mL) were added to the obtained residue, and the mixture was stirred at room temperature overnight. Ethyl acetate and saturated aqueous ammonium chloride solution were added to the reaction mixture, the mixture was extracted 3 times with ethyl acetate, and the obtained ethyl acetate layer was washed with saturated brine. After drying over magnesium sulfate, the desiccant was filtered off, and the filtrate was concentrated under reduced pressure. The obtained residue was purified by silica gel column chromatography (hexane/ethyl acetate) to give the title compound (100 mg, 0.168 mmol, 14%).
MS (ESI) m/z 593 (M+H)$^+$ Step 3. Synthesis of N-(1-{[5-(4-amidino-2-fluorophenoxycarbonyl)thiophen-2-yl]
methylamino}cyclopropanecarbonyl)-L-aspartic acid bis(trifluoroacetate) (B-37)

The compound (100 mg, 0.168 mmol) obtained in step 2 was dissolved in trifluoroacetic acid (0.5 mL), and the mixture was stirred at room temperature for 15 minutes. The reaction mixture was concentrated under reduced pressure and the obtained residue, M-1 (32.4 mg, 0.168 mmol) and WSC hydrochloride (32.6 mg, 0.168 mmol) were dissolved in pyridine (0.5 mL), and the mixture was stirred at room temperature overnight. The reaction mixture was concentrated under reduced pressure. To a solution of the obtained residue in ethanol (0.5 mL) was added a catalytic amount of 10% palladium hydroxide/carbon, and the mixture was stirred at room temperature for 9 hours under a hydrogen atmosphere. The catalyst was filtered off, the filtrate was concentrated under reduced pressure and the obtained residue was purified by high performance liquid chromatography (water-acetonitrile, each containing 0.1% trifluoroacetic acid) to give the title compound (11 mg, 0.022 mmol, 8%).
MS (ESI) m/z 493 (M+H)$^+$ Example 20

Synthesis of N-{[5-(4-amidino-2-fluorophenoxycarbonyl)thiophen-2-yl]methyl}-1H-pyrrole-2-carboxylic acid trifluoroacetate (B-42)

Step 1. Synthesis of 1-{[5-(tert-butoxycarbonyl) thiophen-2-yl]methyl}-pyrrole-2-carboxylic acid benzyl ester A solution of 1H-pyrrole-2-carboxylic acid benzyl ester (283 mg, 1.41 mmol) in tetrahydrofuran (4.0 ml) was cooled to at 0° C. in an ice bath, and sodium hydride (52 mg, 1.3 mmol, 60% in oil) was added. After stirring at 0° C. for 10 minutes, a solution of M-6 (300 mg, 1.08 mmol) in tetrahydrofuran (1.0 ml) was added, and the mixture was stirred at room temperature for 2 hours. 1N Hydrochloric acid (2.6 mL) was added to the reaction mixture, the mixture was extracted 3 times with ethyl acetate, and the obtained ethyl acetate layer was washed with saturated brine. After drying over anhydrous magnesium sulfate, the desiccant was filtered off, and the filtrate was concentrated under reduced pressure. The obtained residue was purified by silica gel column chromatography (hexane/ethyl acetate) to give the title compound (146 mg, 0.367 mmol, 34%).
MS (ESI) m/z 398 (M+H)$^+$ Step 2. Synthesis of N-{[5-(4-amidino-2-fluorophenoxycarbonyl)thiophen-2-yl]methyl}-1H-pyrrole-2-carboxylic acid trifluoroacetate (B-42)

The compound (146 mg, 0.367 mmol) obtained in step 1 was dissolved in trifluoroacetic acid (1.5 mL), and the mixture was stirred at room temperature for 30 minutes. The reaction mixture was concentrated under reduced pressure, the obtained residue, M-1 (90.9 mg, 0.477 mmol) and WSC hydrochloride (106 mg, 0.551 mmol) were dissolved in pyridine (1.5 ml), and the mixture was stirred at room temperature for 5 hours. The reaction mixture was concentrated under reduced pressure. To a solution of the obtained residue in ethanol (1.2 mL)/chloroform (0.3 mL) was added a catalytic amount of 10% palladium hydroxide/carbon, and the mixture was stirred at room temperature for 9 hours under a hydrogen atmosphere. The catalyst was filtered off, the filtrate was concentrated under reduced pressure and the obtained residue was purified by high performance liquid chromatography (water-acetonitrile, each containing 0.1% trifluoroacetic acid) to give the title compound (78 mg, 0.16 mmol, 42%).
$^1$H NMR (400 MHz, DMSO-d$_6$) δ 9.63-9.07 (4H, br), 7.93 (1H, d, J=3.6 Hz), 7.87 (1H, dd, J=13.2, 1.2 Hz), 7.73-7.63 (2H, m), 7.28-7.20 (2H, m), 6.88-6.78 (1H, m), 6.17-6.11 (1H, m), 5.81 (2H, s).
MS (ESI) m/z 388 (M+H)$^+$ Example 21

Synthesis of {2-[(4-amidino-2-fluorophenoxy)carbonyl]-4,5-dihydrothieno[2,3-c]pyridin-6(7H)-yl}acetic acid bis(trifluoroacetate) (B-43)

Step 1. Synthesis of 2-[(4-amidino-2-fluorophenoxy)carbonyl]-4,5,6,7-tetrahydrothieno[2,3-c]pyridine bis(trifluoroacetate)

6-(tert-Butoxycarbonyl)-4,5,6,7-tetrahydrothieno[2,3-c]pyridine-2-carboxylic acid (202 mg, 0.713 mmol), M-1 (163 mg, 0.856 mmol), and WSC hydrochloride (178 mg, 0.927 mmol) were dissolved in pyridine (2.0 ml), and the mixture was stirred at room temperature for 1 hour. The reaction mixture was concentrated under reduced pressure, the obtained residue was dissolved in trifluoroacetic acid (2.0 ml), and the mixture was stirred at room temperature for 2 hours. The reaction mixture was concentrated under reduced pressure and the obtained residue was purified by high performance liquid chromatography (water-acetonitrile, each containing 0.1% trifluoroacetic acid) to give the title compound (197 mg, 0.360 mmol, 51%).
$^1$H NMR (400 MHz, DMSO-d$_6$) δ 9.51-9.40 (2H, br), 9.38-9.26 (2H, br), 9.26-9.14 (2H, br), 8.01-7.90 (2H, m), 7.80-7.73 (2H, m), 4.50 (2H, s), 3.59-3.49 (2H, m), 2.96 (2H, dd, J=6.4, 5.6 Hz).
MS (ESI) m/z 320 (M+H)$^+$ Step 2. Synthesis of {2-[(4-amidino-2-fluorophenoxy)carbonyl]-4,5-dihydrothieno[2,3-c]pyridin-6(7H)-yl}acetic acid bis(trifluoroacetate) (B-43)

To a solution of the compound (138 mg, 0.251 mmol) obtained in step 1 in N,N-dimethylformamide (1.0 ml) was added N,N-diisopropylethylamine (0.131 mL, 0.754 mmol), and bromoacetic acid tert-butyl ester (0.0387 mL, 0.264 mmol) was added, and the mixture was stirred at room temperature for 30 minutes. The reaction mixture was concentrated under reduced pressure, trifluoroacetic acid (1.0 ml) was added to the obtained residue, and the mixture was stirred at room temperature for 2 hours. The reaction mixture was concentrated under reduced pressure and the obtained residue was purified by high performance liquid chromatography (water-acetonitrile, each containing 0.1% trifluoroacetic acid) to give the title compound (71.9 mg, 0.119 mmol, 47%).
$^1$H NMR (400 MHz, DMSO-d$_6$) δ 9.53-9.33 (2H, br), 9.33-9.12 (2H, br), 8.00-7.88 (2H, m), 7.82-7.70 (2H, m), 4.40 (2H, s), 4.07-3.84 (2H, m), 3.47-3.24 (2H, m), 3.05-2.81 (2H, m).
MS (ESI) m/z 378 (M+H)$^+$ Example 22

Synthesis of N-({2-[(4-amidino-2-fluorophenoxy)carbonyl]-4,5-dihydrothieno[2,3-c]pyridin-6(7H)-yl}acetyl)-L-glutamic acid bis(trifluoroacetate) (B-44)

B-43 (32.8 mg, 0.0542 mmol), L-glutamic acid di-tert-butyl ester hydrochloride (17.6 mg, 0.0596 mmol), and WSC hydrochloride (13.5 mg, 0.0704 mmol) were dissolved in pyridine (0.5 mL), and the mixture was stirred at 50° C. for 2 hours. The reaction mixture was concentrated under reduced pressure, the obtained residue was dissolved in trifluoroacetic acid (0.5 mL), and the mixture was stirred at room temperature for 1 hour. The reaction mixture was concentrated under reduced pressure and the obtained residue was purified by high performance liquid chromatography (water-acetonitrile, each containing 0.1% trifluoroacetic acid) to give the title compound (33.2 mg, 0.0452 mmol, 83%).
MS (ESI) m/z 507 (M+H)$^+$ Example 23

Synthesis of N-allyl-N-({2-[(4-amidino-2-fluorophenoxy)carbonyl]-4,5-dihydrothieno[2,3-c]pyridin-6(7H)-yl}acetyl)-L-glutamic acid bis(trifluoroacetate) (B-45)

Step 1. Synthesis of 4,5,6,7-tetrahydrothieno[2,3-c]pyridine-2-carboxylic acid 2,2,2-trichloroethyl ester trifluoroacetate 6-(tert-Butoxycarbonyl)-4,5,6,7-tetrahydrothieno[2,3-c]pyridine-2-carboxylic acid (315 mg, 1.11 mmol) and WSC hydrochloride (426 mg, 2.22 mmol) were dissolved in pyridine (3.5 mL), 2,2,2-trichloroethanol (0.160 mL, 1.67 mmol) was added, and the mixture was stirred at room temperature for 2 hours. The reaction mixture was concentrated under reduced pressure, the obtained residue was dissolved in trifluoroacetic acid (3.5 mL), and the mixture was stirred at room temperature for 1 hour. The reaction mixture was concentrated under reduced pressure and the obtained residue was purified by high performance liquid chromatography (water-acetonitrile, each containing 0.1% trifluoroacetic acid) to give the title compound (204 mg, 0.475 mmol, 43%).

¹H NMR (400 MHz, DMSO-d₆) δ 9.30-9.14 (2H, br), 7.80 (1H, s), 5.12 (2H, s), 4.46 (2H, s), 3.41 (2H, t, J=6.0 Hz), 2.93 (2H, t, J=6.0 Hz).
MS (ESI) m/z 315 (M+H)⁺

Step 2. Synthesis of {2-[(2,2,2-trichloroethoxy)carbonyl]-4,5-dihydrothieno[2,3-c]pyridin-6(7H)-yl}acetic acid trifluoroacetate The compound (63.5 mg, 0.148 mmol) obtained in step 1 was dissolved in N,N-dimethylformamide (0.5 mL), N,N-diisopropylethylamine (0.0568 mL, 0.326 mmol) and bromoacetic acid tert-butyl ester (0.0239 mL, 0.163 mmol) were added, and the mixture was stirred at room temperature for 30 minutes. The reaction mixture was concentrated under reduced pressure, the obtained residue was dissolved in trifluoroacetic acid (0.5 mL), and the mixture was stirred at 60° C. for 4 hours. The reaction mixture was concentrated under reduced pressure and the obtained residue was purified by high performance liquid chromatography (water-acetonitrile, each containing 0.1% trifluoroacetic acid) to give the title compound (63.6 mg, 0.131 mmol, 88%).
¹H NMR (400 MHz, CDCl₃) δ 7.73-7.64 (1H, br), 4.94 (2H, s), 4.58 (2H, s), 3.93 (2H, s), 3.69-3.55 (2H, m), 3.16-3.01 (2H, m).
MS (ESI) m/z 373 (M+H)⁺

Step 3. Synthesis of N-allyl-N-({2-[(2,2,2-trichloroethoxy)carbonyl]-4,5-dihydrothieno[2,3-c]pyridin-6(7H)-yl}acetyl)-L-glutamic acid di-tert-butyl ester The compound (62.3 mg, 0.128 mmol) obtained in step 2, M-4 (55.9 mg, 0.166 mmol), and WSC hydrochloride (36.8 mg, 0.192 mmol) were dissolved in pyridine (0.5 mL), and the mixture was stirred at 60° C. for 5 hours. The reaction mixture was concentrated under reduced pressure and the obtained residue was purified by high performance liquid chromatography (water-acetonitrile, each containing 0.1% trifluoroacetic acid) to give the title compound (72.6 mg, 0.0945 mmol, 74%).
¹H NMR (400 MHz, CDCl₃) δ 7.66 (1H, s), 5.95-5.74 (1H, m), 5.39-5.24 (1H, m), 5.24-5.10 (1H, m), 4.93 (2H, s), 4.71-4.60 (1H, m), 4.57-4.48 (1H, m), 4.40-4.05 (3H, m), 4.04-3.79 (2H, m), 3.77-3.60 (2H, m), 3.06 (2H, t, J=5.7 Hz), 2.33-2.26 (3H, m), 2.11-1.88 (1H, m), 1.49-1.39 (9H, m).
MS (ESI) m/z 655 (M+H)⁺

Step 4. Synthesis of N-allyl-({2-[(4-amidino-2-fluorophenoxy)carbonyl]-4,5-dihydrothieno[2,3-c]pyridin-6(7H)-yl}acetyl)-L-glutamic acid bis(trifluoroacetate) (B-45)

In a solution of the compound (67 mg, 0.087 mmol) obtained in step 3 in acetic acid (0.5 mL) was suspended activated zinc powder (15 mg), and the mixture was stirred at room temperature for 3 hours. The reaction mixture was filtered through a celite, and the filtrate was concentrated under reduced pressure. The obtained residue, M-1 (21.6 mg, is 0.113 mmol) and WSC hydrochloride (25.0 mg, 0.131 mmol) were dissolved in pyridine (0.5 mL), and the mixture was stirred at room temperature overnight. The reaction mixture was concentrated under reduced pressure, the obtained residue was dissolved in trifluoroacetic acid (1.0 ml), and the mixture was stirred at room temperature for 1 hour. The reaction mixture was concentrated under reduced pressure and the obtained residue was purified by high performance liquid chromatography (water-acetonitrile, each containing 0.1% trifluoroacetic acid) to give the title compound (18.5 mg, 0.0239 mmol, 27%).
¹H NMR (400 MHz, DMSO-d₆) δ 9.48-9.35 (2H, br), 9.25-9.08 (2H, br), 8.02-7.84 (1H, m), 7.82-7.69 (1H, m), 7.62 (1H, s), 7.12-7.01 (1H, m), 5.99-5.74 (1H, m), 5.45-5.02 (2H, m), 4.59-4.20 (3H, m), 4.17-3.97 (2H, m), 3.96-3.83 (2H, m), 3.14-2.83 (2H, m), 2.40-2.25 (2H, m), 2.25-2.12 (2H, m), 2.12-1.89 (2H, m).
MS (ESI) m/z 547 (M+H)⁺

Example 24

Synthesis of N—[N-{[5-(4-amidino-2-fluorophenoxycarbonyl)thiophen-2-yl]methyl}-N-(2-methylpropyl)aminocarbonyl]-L-aspartic acid trifluoroacetate (B-49)

Step 1. Synthesis of 5-{[(2-methylpropyl)amino]methyl}thiophene-2-carboxylic acid tert-butyl ester M-6 (1.0 g, 4.3 mmol), isobutylamine (2.1 mL, 22 mmol), and N,N-diisopropylethylamine (0.90 mL, 5.2 mmol) were dissolved in acetonitrile (80 ml), sodium iodide (0.70 g, 4.7 mmol) was added, and the mixture was stirred at 60° C. for 2 hours. The reaction mixture was diluted with ethyl acetate, and washed with aqueous sodium hydrogen carbonate solution and saturated brine. After drying over anhydrous magnesium sulfate, the solvent was evaporated under reduced pressure to give the title compound.
¹H NMR (400 MHz, CDCl₃) δ 7.87 (1H, d, J=3.7 Hz), 7.57 (1H, d, J=3.7 Hz), 3.96 (2H, s), 2.46 (2H, d, J=6.8 Hz), 1.87-1.67 (1H, m), 1.56 (9H, s), 0.92 (6H, d, J=6.7 Hz).

Step 2. Synthesis of N-phenoxycarbonyl-L-aspartic acid dimethyl ester

L-aspartic acid dimethyl ester hydrochloride (2.0 g, 10 mmol) was dissolved in dichloromethane (30 ml), phenyl chloroformate (1.3 mL, 11 mmol) and N,N-diisopropylethylamine (4.4 mL, 25 mmol) were added at 0° C., and the mixture was stirred at room temperature for 2 hours. The solvent was evaporated under reduced pressure, ethyl acetate was added, and the mixture was washed with water and saturated brine. After drying over anhydrous magnesium sulfate, the solvent was evaporated under reduced pressure to give the title compound.
¹H NMR (400 MHz, CDCl₃) δ 7.61-6.98 (5H, m), 6.06 (1H, d, J=7.7 Hz), 4.68 (1H, dt, J=8.7, 4.5 Hz), 3.81 (3H, s), 3.73 (3H, s), 3.10 (1H, dd, J=17.3, 4.4 Hz), 2.94 (1H, dd, J=17.3, 4.5 Hz).

Step 3. Synthesis of N—{N-[(5-tert-butoxycarbonylthiophen-2-yl)methyl]-N-(2-methylpropyl)aminocarbonyl}-L-aspartic acid dimethyl ester The compound (1.1 g, 4.1 mmol) obtained in step 1 and the compound (1.2 g, 4.1 mmol) obtained in step 2 were dissolved in acetonitrile (40 ml), N,N-diisopropylethylamine (0.71 mL, 4.1 mmol) was added, and the mixture was stirred at 60° C. for 2 hours. The solvent was evaporated under reduced pressure, ethyl acetate was added, and the mixture was washed with water and saturated brine. After drying over anhydrous magnesium sulfate, the solvent was evaporated under reduced pressure, and the obtained residue was purified by silica gel column chromatography (hexane/ethyl acetate) to give the title compound.

¹H NMR (400 MHz, CDCl₃) δ 7.56 (1H, d, J=3.7 Hz), 6.91 (1H, d, J=3.7 Hz), 5.64 (1H, d, J=7.9 Hz), 4.85-4.75 (1H, m), 4.68 (1H, d, J=16.3 Hz), 4.58 (1H, d, J=16.3 Hz), 3.75 (3H, s), 3.67 (3H, s), 3.10-2.99 (3H, m), 2.87 (1H, dd, J=17.1, 4.6 Hz), 2.03-1.92 (1H, m), 1.55 (9H, s), 0.96 (3H, d, J=6.7 Hz), 0.94 (3H, d, J=6.6 Hz).
MS (ESI) m/z 457 (M+H)⁺

Step 4. Synthesis of N—[N-{[5-(4-amidino-2-fluorophenoxycarbonyl)thiophen-2-yl]methyl}-N-(2-methylpropyl)aminocarbonyl]-L-aspartic acid trifluoroacetate (B-49)

The compound obtained in step 3 was subjected to an operation similar to that in Example 14, steps 2 and 3, using M-1 instead of 4-hydroxybenzamidine hydrochloride to give the title compound.
¹H NMR (400 MHz, DMSO-d₆) δ 9.41 (2H, s), 9.13 (2H, s), 7.96-7.89 (2H, m), 7.80-7.71 (2H, m), 7.22 (1H, d, J=3.9 Hz), 6.61 (1H, br s), 4.67 (2H, s), 4.53-4.36 (1H, m), 3.11-2.93 (2H, m), 2.78-2.64 (1H, m), 2.58 (1H, dd, J=16.2, 7.0 Hz), 2.01-1.85 (1H, m), 0.91-0.76 (6H, m).
MS (ESI) m/z 509 (M+H)⁺

Example 25

Synthesis of N—[N-{[5-(4-amidinophenoxycarbonyl)thiophen-2-yl]methyl}-N-(carboxymethyl)aminocarbonyl]-L-aspartic acid trifluoroacetate (B-52)

Step 1. Synthesis of 5-{[N-(tert-butoxycarbonylmethyl)amino]methyl}thiophene-2-carboxylic acid benzyl ester trifluoroacetate Glycine tert-butyl ester hydrochloride (0.45 g, 2.7 mmol) was dissolved in methanol (1 mL), 28% sodium methoxide/methanol solution (0.518 mL) was added, and the mixture was stirred for 10 minutes. The solvent was evaporated under reduced pressure, dichloromethane was added, and the mixture was filtered through celite. 5-Formyl-2-thiophenecarboxylic acid benzyl ester (0.49 g, 2.0 mmol), acetic acid (20 mg, 0.33 mmol) and sodium cyanoborohydride (0.19 g, 3.0 mmol) were added to the obtained filtrate, and the mixture was stirred at room temperature overnight. The reaction mixture was diluted with ethyl acetate, and washed with aqueous sodium hydrogen carbonate solution and saturated brine. After drying over anhydrous magnesium sulfate, the solvent was evaporated under reduced pressure, and the residue was purified by high performance liquid chromatography (water-acetonitrile, each containing 0.1% trifluoroacetic acid) to give the title compound (0.38 g, 0.8 mmol).
¹H NMR (400 MHz, CDCl₃) δ 7.74 (1H, d, J=3.8 Hz), 7.52-7.27 (6H, m), 5.32 (2H, s), 4.45 (2H, s), 3.63 (2H, s), 1.43 (9H, s).
MS (ESI) m/z 362 (M+H)⁺

Step 2. Synthesis of N-(1H-imidazol-1-ylcarbonyl)-L-aspartic acid di-tert-butyl ester L-aspartic acid di-tert-butyl ester (0.84 g, 3.0 mmol) and 1,1'-carbonyldiimidazole (2.4 g, 15 mmol) were dissolved in N,N-dimethylformamide (10 ml), and the mixture was stirred at room temperature overnight. The reaction mixture was concentrated under reduced pressure, ethyl acetate was added, and the mixture was washed with 1N hydrochloric acid (15 mL) and saturated brine. After drying over anhydrous magnesium sulfate, the solvent was evaporated under reduced pressure, and the residue was purified by silica gel column chromatography (hexane/ethyl acetate) to give the title compound (0.72 g, 2.1 mmol).
¹H NMR (400 MHz, CDCl₃) δ 8.14 (1H, s), 7.35 (1H, d, J=1.4 Hz), 7.12 (1H, d, J=1.4 Hz), 6.85 (1H, d, J=7.7 Hz), 4.69 (1H, m), 3.00 (1H, dd, J=17.3, 4.1 Hz), 2.84 (1H, dd, J=17.3, 4.3 Hz), 1.49 (9H, s), 1.46 (9H, s).
MS (ESI) m/z 340 (M+H)⁺

Step 3. Synthesis of N—{N-[(5-benzyloxycarbonylthiophen-2-yl)methyl]-N-(tert-butoxycarbonylmethyl)aminocarbonyl}-L-aspartic acid di-tert-butyl ester The compound (0.10 g, 0.21 mmol) obtained in step 1 and the compound (94 mg, 0.28 mmol) obtained in step 2 were dissolved in N,N-dimethylformamide (5 mL), and the mixture was stirred at 80° C. overnight. The reaction mixture was concentrated under reduced pressure, ethyl acetate was added, and the mixture was washed with 1N hydrochloric acid and saturated brine. After drying over anhydrous magnesium sulfate, the solvent was evaporated under reduced pressure, and the residue was purified by silica gel column chromatography (hexane/ethyl acetate) to give the title compound (0.10 g, 0.16 mmol).
¹H NMR (400 MHz CDCl₃) δ 7.69 (1H, d, J=3.8 Hz), 7.46-7.29 (5H, m), 7.01 (1H, d, J=3.8 Hz), 5.79 (1H, d, J=7.7 Hz), 5.31 (2H, s), 4.72 (1H, d, J=16.8 Hz), 4.64 (1H, d, J=16.9 Hz), 4.61-4.56 (1H, m), 3.90 (2H, s), 2.87 (1H, dd, J=17.0, 4.3 Hz), 2.70 (1H, dd, J=17.0, 4.5 Hz), 1.44 (9H, s), 1.43 (9H, s), 1.39 (9H, s).
MS (ESI) m/z 633 (M+H)⁺

Step 4. Synthesis of N—[N-{[5-(4-amidinophenoxycarbonyl)thiophen-2-yl]methyl}-N-(carboxymethyl)aminocarbonyl]-L-aspartic acid trifluoroacetate (B-52)

The compound (0.1 g, 0.16 mmol) obtained in step 3 was dissolved in methanol (9 mL) and chloroform (1 mL), palladium hydroxide (20 mg) was added, and the mixture was stirred under a hydrogen atmosphere at room temperature overnight. The reaction mixture was filtered through celite, and the filtrate was concentrated under reduced pressure. The obtained residue was subjected to an operation similar to that in Example 7, step 2 to give the title compound.
¹H NMR (400 MHz, DMSO-d₆) δ 9.34 (2H, s), 8.96 (2H, s), 8.01-7.74 (3H, m), 7.57 (2H, d, J=8.8 Hz), 7.22 (1H, d, J=3.8 Hz), 6.96 (1H, d, J=7.5 Hz), 4.69 (2H, s), 4.58-4.28 (1H, m), 3.96 (2H, s), 2.87-2.60 (1H, m), 2.62-2.51 (1H, m).
MS (ESI) m/z 493 (M+H)⁺

Example 26

Synthesis of N-{[2-(4-amidino-2-fluorophenoxycarbonyl)-4,5,6,7-tetrahydrothieno[2,3-c]pyridin-6-yl]carbonyl}-L-aspartic acid trifluoroacetate (B-55)

6-(tert-Butoxycarbonyl)-4,5,6,7-tetrahydrothieno[2,3-c]pyridine-2-carboxylic acid (61.5 mg, 0.217 mmol) was dissolved in trifluoroacetic acid (0.5 mL), and the mixture was stirred at room temperature for 1 hour. The reaction mixture was concentrated under reduced pressure, and the obtained residue and the compound (88.4 mg, 0.260 mmol) obtained in Example 25, step 2 were dissolved in acetonitrile (0.5 mL). N,N-diisopropylethylamine (0.11 mL, 0.65 mmol) was added, and the mixture was stirred at 60° C. for 3 hours. The reaction mixture was concentrated under reduced pressure, dichloromethane and 1N hydrochloric acid were added to the obtained residue, and the mixture was extracted with dichloromethane. The obtained dichloromethane layer was washed with saturated brine, and dried over magnesium sulfate. The desiccant was filtered off, and the filtrate was concentrated under reduced pressure. M-1 (53.8 mg, 0.282 mmol), WSC hydrochloride (62.4 mg, 0.326 mmol), and pyridine (0.5 mL) were added to the obtained residue, and the mixture was stirred at room temperature for 1 hour. The reaction mixture was concentrated under reduced pressure, trifluoroacetic acid (0.5 mL) was added to the obtained residue, and the mixture was stirred at room temperature for 1 hour. The reaction mixture was concentrated under reduced pressure and the obtained residue was purified by high performance liquid chromatography (water-acetonitrile, each containing 0.1% trifluoroacetic acid) to give the title compound (54.2 mg, 0.0915 mmol, 42%).

$^1$H NMR (400 MHz, DMSO-$d_6$) δ 9.50-9.24 (2H, br), 9.24-8.99 (2H, br), 7.93-7.78 (2H, m), 7.74-7.62 (2H, m), 6.96 (1H, d, J=7.5 Hz), 4.62 (2H, s), 4.42-4.31 (1H, m), 3.64-3.54 (2H, m), 2.74-2.62 (2H, m), 2.58-2.45 (2H, m).

MS (ESI) m/z 479 (M+H)$^+$

Example 27

Synthesis of N—[N-allyl-N-(3-{5-[(4-amidino-2-fluorophenoxy)carbonyl]thiophen-2-yl}propanoyl) glycyl]-L-aspartic acid trifluoroacetate (B-56)

Step 1. Synthesis of (E)-3-[5-(benzyloxycarbonyl) thiophen-2-yl]propenoic acid tert-butyl ester Diethylphosphonoacetic acid tert-butyl ester (12 g, 48 mmol) was dissolved in tetrahydrofuran (50 ml), 60% sodium hydride (1.6 g, 41 mmol) was added at 0° C., and the mixture was stirred for 30 minutes. A solution of 5-formyl-2-thiophenecarboxylic acid benzyl ester (8.8 g, 36 mmol) in tetrahydrofuran (1 mL) was added to the reaction mixture, and the mixture was stirred at room temperature overnight. The solvent was evaporated, and the residue was partitioned between ethyl acetate and 1N hydrochloric acid, and the organic layer was washed successively with water and saturated brine. After drying over anhydrous magnesium sulfate, the residue was purified by silica gel column chromatography (hexane/ethyl acetate) to give the title compound.

$^1$H NMR (400 MHz, CDCl$_3$) δ 7.51-7.32 (5H, m), 7.28 (1H, d, J=17.2 Hz), 7.20 (1H, d, J=3.6 Hz), 6.62 (1H, d, J=3.6 Hz), 6.49 (1H, d, J=17.2 Hz), 5.35 (2H, s), 1.52 (9H, d, J=1.3 Hz).

Step 2. Synthesis of 3-[5-(4-amidino-2-fluorophenoxycarbonyl)thiophen-2-yl]propionic acid trifluoroacetate The compound (0.50 g, 1.5 mmol) obtained in step 1 was dissolved in methanol (4 mL) and chloroform (1 mL), a catalytic amount of palladium hydroxide was added, and the mixture was stirred at room temperature under a 1 atm hydrogen atmosphere overnight. After completion of the reaction, palladium hydroxide was filtered off through celite, and the solvent was evaporated under reduced pressure. The obtained residue was dissolved in pyridine (5 mL), M-1 (0.28 g, 1.5 mmol) and WSC hydrochloride (0.41 g, 2.1 mmol) were added, and the mixture was stirred for 3 hours. The solvent was evaporated under reduced pressure, and the residue was purified by high performance liquid chromatography (water-acetonitrile, each containing 0.1% trifluoroacetic acid) and lyophilized. Trifluoroacetic acid (3 mL) was added to the obtained solid, and the mixture was stirred for 1 hour. The solvent was evaporated under reduced pressure, and the residue was purified by high performance liquid chromatography (water-acetonitrile, each containing 0.1% trifluoroacetic acid) to give the title compound (0.11 g, 0.24 mmol).

$^1$H NMR (400 MHz, DMSO-$d_6$) δ 9.41 (2H, br), 9.09 (2H, br), 8.08-7.81 (2H, m), 7.75 (2H, t, J=4.1 Hz), 7.15 (1H, d, J=3.8 Hz), 3.15 (2H, t, J=7.2 Hz), 2.68 (2H, t, J=7.2 Hz).

MS (ESI) m/z 337 (M+H)$^+$

Step 3. Synthesis of N-allyl-N-(3-{5-[(4-amidino-2-fluorophenoxy)carbonyl]thiophen-2-yl}propanoyl) glycine trifluoroacetate The compound (44.8 mg, 0.100 mmol) obtained in step 2 was dissolved in thionyl chloride (0.5 mL), and the mixture was stirred at room temperature for 15 minutes. The reaction mixture was concentrated under reduced pressure, to a solution of the obtained residue and M-5 (20.5 mg, 0.120 mmol) in dichloromethane (0.3 mL) was added pyridine (0.3 mL), and the mixture was stirred at room temperature for 30 minutes. The reaction mixture was concentrated under reduced pressure, trifluoroacetic acid (0.5 mL) was added to the obtained residue, and the mixture was stirred at room temperature for 15 minutes. The reaction mixture was concentrated under reduced pressure and the obtained residue was purified by high performance liquid chromatography (water-acetonitrile, each containing 0.1% trifluoroacetic acid) to give the title compound (23.8 mg, 0.0435 mmol, 44%).

$^1$H NMR (400 MHz, DMSO-$d_6$) δ 9.77-9.10 (4H, br), 8.01-7.86 (2H, m), 7.82-7.66 (2H, m), 7.14 (1H, d, J=3.8 Hz), 5.94-5.63 (1H, m), 5.22-5.05 (2H, m), 4.10-3.86 (4H, m), 3.15 (2H, t, J=7.0 Hz), 2.79 (1H, t, J=7.0 Hz), 2.70 (1H, t, J=7.0 Hz).

MS (ESI) m/z 434 (M+H)$^+$

Step 4. Synthesis of N—[N-allyl-N-(3-{(5-[(4-amidino-2-fluorophenoxy)carbonyl]thiophen-2-yl}propanoyl)glycyl]-L-aspartic acid trifluoroacetate (B-56)

The compound (18 mg, 0.032 mmol) obtained in step 3, L-aspartic acid di-tert-butyl ester (14 mg, 0.048 mmol), and WSC hydrochloride (9.2 mg, 0.048 mmol) were dissolved in pyridine (0.5 mL), and the mixture was stirred at room temperature overnight. The reaction mixture was concentrated under reduced pressure, trifluoroacetic acid (0.5 mL) was added to the obtained residue, and the mixture was stirred at room temperature for 1 hour. The reaction mixture was concentrated under reduced pressure and the obtained residue was purified by high performance liquid chromatography (water-acetonitrile, each containing 0.1% trifluoroacetic acid) to give the title compound (12 mg, 0.019 mmol, 58%).

$^1$H NMR (400 MHz, DMSO-$d_6$) δ 9.51-9.32 (2H, br), 9.26-9.09 (2H, br), 8.47 (0.5H, d, J=8.1 Hz), 8.23 (0.5H, d, J=8.1 Hz), 7.97-7.89 (2H, m), 7.81-7.69 (2H, m), 7.14 (1H, d,

J=3.9 Hz), 5.84 (0.5H, ddd, J=22.4, 10.4, 5.2 Hz), 5.70 (0.5H, ddd, J=16.1, 10.9, 5.8 Hz), 5.21-5.02 (2H, m), 4.63-4.49 (1H, m), 4.06-3.82 (4H, m), 3.20-3.08 (2H, m), 2.88-2.47 (4H, m).
MS (ESI) m/z 549 (M+H)$^+$ Example 28

Synthesis of N-allyl-N—[N-allyl-N-(3-{5-[(4-amidinophenoxy)carbonyl]-3-methylthiophen-2-yl}propanoyl)glycyl]-L-glutamic acid trifluoroacetate (B-57)

Step 1. Synthesis of 3-[5-(4-amidinophenoxycarbonyl)-3-methylthiophen-2-yl]propionic acid trifluoroacetate Using 5-formyl-3-methyl-2-thiophenecarboxylic acid benzyl ester instead of 5-formyl-2-thiophenecarboxylic acid benzyl ester and 4-amidinophenol hydrochloride instead of M-1, and by an operation similar to that in Example 27, steps 1 and 2, the title compound was obtained.
$^1$H NMR (400 MHz, DMSO-d$_6$) δ 9.35 (2H, br), 9.05 (2H, br), 7.93-7.86 (2H, m), 7.81 (1H, s), 7.58-7.51 (2H, m), 3.05 (2H, t, J=7.2 Hz), 2.61 (2H, t, J=7.2 Hz), 2.21 (3H, s).
MS (ESI) m/z 333 (M+H)$^+$ Step 2. Synthesis of N-allyl-N-(3-{5-[(4-amidinophenoxy)carbonyl]-3-methylthiophen-2-yl}propanoyl)glycine trifluoroacetate The compound (100 mg, 0.224 mmol) obtained in step 1, M-5 (49.9 mg, 0.291 mmol), and WSC hydrochloride (64.4 mg, 0.336 mmol) were dissolved in pyridine (0.5 mL), and the mixture was stirred at room temperature overnight. The reaction mixture was concentrated under reduced pressure, trifluoroacetic acid (1.0 ml) was added to the obtained residue, and the mixture was stirred at room temperature for 30 minutes. The reaction mixture was concentrated under reduced pressure and the obtained residue was purified by high performance liquid chromatography (water-acetonitrile, each containing 0.1% trifluoroacetic acid) to give the title compound (98.5 mg, 0.181 mmol, 81%).
$^1$H NMR (400 MHz, DMSO-d$_6$) δ 9.42-9.29 (2H, br), 9.10-8.93 (2H, br), 7.94-7.85 (2H, m), 7.79 (1H, s), 7.53 (2H, d, J=8.6 Hz), 5.94-5.61 (1H, m), 5.22-5.06 (2H, m), 4.12-3.89 (4H, m), 3.04 (2H, dd, J=7.1 Hz), 2.72 (1H, t, J=7.1 Hz), 2.62 (1H, t, J=7.2 Hz), 2.20 (3H, s).
MS (ESI) m/z 430 (M+H)$^+$ Step 3. Synthesis of N-allyl-N—[N-allyl-N-(3-{5-[(4-amidinophenoxy)carbonyl]-3-methylthiophen-2-yl}propanoyl)glycyl]-L-glutamic acid trifluoroacetate (B-57)

The compound (47 mg, 0.086 mmol) obtained in step 2, M-4 (37.8 mg, 0.112 mmol), and WSC hydrochloride (24.9 mg, 0.130 mmol) were dissolved in pyridine (0.5 mL), and the mixture was stirred at room temperature for 4 hours. The reaction mixture was concentrated under reduced pressure, trifluoroacetic acid (0.5 mL) was added to the obtained residue, and the mixture was stirred at room temperature for 2 hours. The reaction mixture was concentrated under reduced pressure and the obtained residue was purified by high performance liquid chromatography (water-acetonitrile, each containing 0.1% trifluoroacetic acid) to give the title compound (44.8 mg, 0.0629 mmol, 73%).
$^1$H NMR (400 MHz, DMSO-d$_6$) δ 9.46-9.22 (2H, br), 9.16-8.91 (2H, br), 7.92-7.86 (2H, m), 7.80-7.76 (1H, m), 7.56-7.49 (1H, m), 5.97-5.61 (2H, m), 5.40-4.97 (4H, m), 4.57-3.77 (7H, m), 3.10-2.97 (2H, m), 2.78-2.65 (1H, m), 2.37-2.19 (4H, m), 2.18-2.04 (1H, m), 2.02-1.84 (1H, m).
MS (ESI) m/z 603 (M+H)$^+$ Example 29

Synthesis of N—[N-{5-[(4-amidino-2-fluorophenoxy)carbonyl]thiophen-2-yl}methyl-N-(2-methylpropyl)carbamoyl]-N-propylglycine trifluoroacetate (B-58)

Step 1. Synthesis of N-(1H-imidazol-1-ylcarbonyl)-allylamine

Allylamine (1.0 g, 17.5 mmol) was dissolved in dichloromethane (30 ml), 1,1'-carbonyldiimidazole (7.37 g, 15 mmol) was added, and the mixture was stirred overnight. The solvent was evaporated under reduced pressure, and the residue was partitioned between ethyl acetate and 1N hydrochloric acid. The organic layer was washed with saturated brine, and dried over anhydrous sodium sulfate, and the solvent was evaporated under reduced pressure to give the title compound.
MS (ESI) m/z 152 (M+H)$^+$ Step 2. Synthesis of 5-{[N-(allylcarbamoyl)-N-(2-methylpropyl)amino]methyl}thiophene-2-carboxylic acid tert-butyl ester 5-{[(2-Methylpropyl)amino]methyl}thiophene-2-carboxylic acid tert-butyl ester (0.55 g, 2.0 mmol) obtained in Example 24, step 1 and N-(1H-imidazol-1-ylcarbonyl)-allylamine (0.49 g, 3.2 mmol) obtained in step 1 were dissolved in acetonitrile (20 ml), N,N-diisopropylethylamine (0.56 mL, 3.2 mmol) was added, and the mixture was stirred at 60° C. overnight. The reaction mixture was concentrated under reduced pressure and the obtained residue was purified by column chromatography (hexane/ethyl acetate) to give the title compound (0.72 g, 2.0 mmol).
$^1$H NMR (400 MHz, DMSO-d$_6$) δ 7.57 (1H, d, J=3.6 Hz), 6.91 (1H, d, J=3.6 Hz), 5.92-5.83 (1H, m), 5.17-5.08 (2H, m), 4.63 (2H, s), 4.44 (1H, t, J=5.6 Hz), 3.88 (2H, m), 3.02 (2H, d, J=7.6 Hz), 1.95 (1H, m), 1.56 (9H, s), 0.94 (6H, d, J=6.8 Hz).
MS (ESI) m/z 353 (M+H)$^+$ Step 3. Synthesis of 5-({N—[N-allyl-N-(benzyloxycarbonylmethyl)carbamoyl]-N-(2-methylpropyl)amino}methyl)thiophene-2-carboxylic acid tert-butyl ester The compound (0.59 g, 1.66 mmol) obtained in step 2 was dissolved in tetrahydrofuran (10 ml), and the mixture was cooled to −78° C. Lithium bis(trimethylsilyl)amide/1.0M tetrahydrofuran solution (2.28 mL, 2.28 mmol) was added dropwise, and the mixture was stirred at −78° C. for 30 minutes. Bromoacetic acid benzyl ester (0.42 g, 1.83 mmol) was added dropwise to the reaction mixture, and the mixture was stirred at room temperature overnight. Ethyl acetate and 1N hydrochloric acid were added to the reaction mixture, the mixture was partitioned, and the organic layer was washed with saturated brine. The solvent was concentrated under reduced pressure and the obtained residue was purified by high performance liquid chromatography (water-acetonitrile, each containing 0.1% trifluoroacetic acid) to give the title compound (0.31 g, 0.62 mmol).

$^1$H NMR (400 MHz, DMSO-d$_6$) δ 7.54 (1H, d, J=3.6 Hz), 7.38-7.28 (5H, m), 6.88 (1H, d, J=3.6 Hz), 5.85-5.75 (1H, m), 5.27-5.19 (2H, m), 5.17 (2H, s), 4.52 (2H, s), 3.95 (2H, d, J=5.2 Hz), 3.93 (2H, s), 2.93 (2H, d, J=7.6 Hz), 1.95 (1H, m), 1.56 (9H, s), 0.84 (6H, d, J=6.8 Hz).

MS (ESI) m/z 501 (M+H)$^+$

Step 4. Synthesis of N-allyl-N—[N-{5-[(4-amidino-2-fluorophenoxy)carbonyl]thiophen-2-yl}methyl-N-(2-methylpropyl)carbamoyl]glycine benzyl ester trifluoroacetate To the compound (0.31 g, 0.62 mmol) obtained in step 3 was added trifluoroacetic acid (3 mL), and the mixture was stirred for 30 minutes. The reaction mixture was concentrated under reduced pressure, the obtained residue, M-1 (120 mg, 0.63 mmol) and WSC hydrochloride (240 mg, 1.25 mmol) were dissolved in pyridine (3 mL), and the mixture was stirred at 50° C. for 3 hours. The reaction mixture was concentrated under reduced pressure and the obtained residue was purified by high performance liquid chromatography (water-acetonitrile, each containing 0.1% trifluoroacetic acid) to give the title compound (67 mg, 0.096 mmol).

MS (ESI) m/z 581 (M+H)$^+$

Step 5. Synthesis of N—[N-{5-[(4-amidino-2-fluorophenoxy)carbonyl]thiophen-2-yl}methyl-N-(2-methylpropyl)carbamoyl]-N-propylglycine trifluoroacetate (B-58)

The compound (67 mg, 0.096 mmol) obtained in step 4 was dissolved in isopropanol (4 mL) and water (4 mL), a catalytic amount of 20% palladium hydroxide/carbon was added, and the mixture was stirred at room temperature for 3 hours under a hydrogen atmosphere. The catalyst was filtered off, the filtrate was concentrated under reduced pressure and the obtained residue was purified by high performance liquid chromatography (water-acetonitrile, each containing 0.1% trifluoroacetic acid) to give the title compound (22 mg, 0.036 mmol).

$^1$H NMR (400 MHz, DMSO-d$_6$) δ 9.46 (2H, br s), 9.22 (2H, br s), 8.00-7.95 (2H, m), 7.80-7.75 (2H, m), 7.25 (1H, d, J=4.0 Hz), 4.55 (2H, s), 3.88 (2H, s), 3.18 (2H, t, J=6.8 Hz), 2.87 (2H, m), 1.93 (1H, m), 1.65-1.45 (2H, m), 0.88 (3H, t, J=6.8 Hz), 0.82 (6H, d, J=6.8 Hz).

MS (ESI) m/z 493 (M+H)$^+$

Example 30

Synthesis of N—(N-{5-[(4-amidino-2-fluorophenoxy)carbonyl]thiophen-2-yl}methyl-N-methyl-D-phenylalanyl)-D-aspartic acid bis(trifluoroacetate) (B-59)

Using M-1 and a commercially available reagent and by an operation similar to that in the above-mentioned Example 16, the title compound was synthesized.

$^1$H NMR (400 MHz, D$_2$O) δ 8.06 (1H, d, J=3.6 Hz), 7.75 (1H, dd, J=10.4, 2.4 Hz), 7.68 (1H, dd, J=8.8, 1.6 Hz), 7.56 (1H, t, J=3.6 Hz), 7.46 (1H, d, J=4.0 Hz), 7.35-7.25 (3H, m), 7.22-7.15 (2H, m), 4.75 (2H, s), 4.38 (1H, dd, J=8.0, 3.6 Hz), 4.16 (1H, dd, J=10.8, 5.2 Hz), 3.51 (1H, dd, J=12.8, 5.2 Hz), 3.10 (1H, t, J=12.8 Hz), 2.99 (3H, s), 2.85 (1H, dd, J=17.2, 4.8 Hz), 2.50 (1H, dd, J=17.2, 8.0 Hz).

MS (ESI) m/z 571 (M+H)$^+$

Example 31

Synthesis of N-{5-[(4-amidino-2-fluorophenoxy)carbonyl]thiophen-2-yl}methyl-D-proline N-(2-carboxyethyl)-N-carboxymethylamide bis(trifluoroacetate) (B-60)

Step 1. Synthesis of 3-(methoxycarbonylmethylamino)propanoic acid methyl ester hydrochloride 3-Aminopropanoic acid methyl ester (4.0 g, 28.7 mmol) was dissolved in methanol (40 ml), bromoacetic acid methyl ester (0.8 mL, 8.6 mmol) and N,N-diisopropylethylamine (7 mL, 41 mmol) were added, and the mixture was stirred overnight. The solvent was evaporated under reduced pressure, and the obtained residue was purified by high performance liquid chromatography (water-acetonitrile, each containing 0.1% trifluoroacetic acid), and lyophilized. 0.1N Hydrochloric acid (100 ml) was added to the obtained residue, and the mixture was lyophilized to give the title compound (2.26 g, 10.7 mmol).

$^1$H NMR (400 MHz, CDCl$_3$) δ 3.94 (2H, s), 3.84 (3H, s), 3.75 (3H, s), 3.42 (2H, t, J=7.2 Hz), 2.95 (2H, t, J=7.2 Hz).

MS (ESI) m/z 176 (M+H)$^+$

Step 2. Synthesis of N-tert-butoxycarbonyl-D-proline N-(2-methoxycarbonylethyl)-N-methoxycarbonylmethylamide trifluoroacetate N-tert-Butoxycarbonyl-D-proline (1.1 g, 5.1 mmol) was dissolved in dichloromethane (30 ml), WSC hydrochloride (1.25 g, 6.5 mmol) and 1-hydroxybenzotriazole monohydrate (0.84 g, 5.5 mmol) were added, and the mixture was stirred at room temperature for 30 minutes. 3-(Methoxycarbonylmethylamino)propanoic acid methyl ester hydrochloride (1.06 g, 5.0 mmol) obtained in step 1 and N,N-diisopropylethylamine (1.1 mL, 6.5 mmol) were added to the reaction mixture, and the mixture was stirred overnight. The solvent was evaporated under reduced pressure, and the residue was partitioned between ethyl acetate and water. The organic layer was washed successively with 5% aqueous sodium hydrogen carbonate solution and saturated brine, and dried over anhydrous sodium sulfate, and the solvent was evaporated under reduced pressure. Trifluoroacetic acid (20 ml) was added to the obtained residue, the mixture was stirred for 1 hour, and the solvent was evaporated under reduced pressure. The obtained residue was dissolved in acetonitrile (15 mL), M-6 (0.69 g, 3.0 mmol), sodium iodide (445 mg, 3.0 mmol), and N,N-diisopropylethylamine (1.2 ml, 6.8 mmol) were added, and the mixture was stirred at 60° C. overnight. The solvent was evaporated under reduced pressure, and the residue was partitioned between ethyl acetate and 5% aqueous sodium hydrogen carbonate solution. The organic layer was washed with saturated brine, and dried over anhydrous sodium sulfate, and the solvent was evaporated under reduced pressure. The obtained residue was purified by silica gel column chromatography to give the title compound (0.21 g, 0.45 mmol).

MS (ESI) m/z 469 (M+H)$^+$

Step 3. Synthesis of N-{5-[(4-amidino-2-fluorophenoxy)carbonyl]thiophen-2-yl}methyl-D-proline N-(2-methoxycarbonylethyl)-N-methoxycarbonylmethylamide bis(trifluoroacetate)

To the compound (0.21 g, 0.45 mmol) obtained in step 2 was added trifluoroacetic acid (10 ml), the mixture was stirred for 1 hour, and the solvent was evaporated under reduced pressure. The obtained residue was dissolved in pyridine (10 ml), M-1 (86 mg, 0.45 mmol) and WSC hydrochloride (86 mg, 0.45 mmol) were added, and the mixture was stirred at 50° C. for 3 hours. The reaction mixture was concentrated under reduced pressure and the obtained residue was purified by high performance liquid chromatography (water-acetonitrile, each containing 0.1% trifluoroacetic acid) to give the title compound (306 mg, 0.39 mmol).

MS (ESI) m/z 549 (M+H)$^+$

Step 4. Synthesis of N-{5-[(4-amidino-2-fluorophenoxy)carbonyl]thiophen-2-yl}methyl-D-proline N-(2-carboxyethyl)-N-carboxymethylamide bis(trifluoroacetate) (B-60)

The compound (306 mg, 0.39 mmol) obtained in step 3 was dissolved in 4N hydrochloric acid (4 mL), and the mixture was stirred at 60° C. for 3 hours. The reaction mixture was purified by high performance liquid chromatography (water-acetonitrile, each containing 0.1% trifluoroacetic acid) to give the title compound (153 mg, 0.20 mmol).

MS (ESI) m/z 521 (M+H)$^+$

The compounds A-2 and A-16 shown in the following Table 2 were each synthesized using commercially available reagents and by an operation in the same manner as in the above-mentioned Example 7.

The compounds B-2 to 4 and B-19 shown in the following Table 2 were each synthesized using M-1 and commercially available reagents and by an operation in the same manner as in the above-mentioned Example 14.

The compounds A-7, A-9, A-13, A-17, B-5, B-7, B-8, B-11, B-13, B-16, B-20, and B-21 shown in the following Table 2 were each synthesized using M-5, A-2, A-12, A-16, B-1, B-3, B-4, B-19 and commercially available reagents and by an operation in the same manner as in the above-mentioned Example 8.

The compounds A-5, A-6, A-8, A-10, A-11, B-6, B-9, B-10, B-12, B-14, and B-15 shown in the following Table 2 were each synthesized using M-2, A-1, A-2, B-1 to 3 and commercially available reagents and by an operation in the same manner as in the above-mentioned Example 9.

The compound A-15 shown in the following Table 2 was synthesized using commercially available reagents and by an operation in the same manner as in the above-mentioned Example 11.

The compound B-18 shown in the following Table 2 was synthesized using M-1 and commercially available reagents and by an operation in the same manner as in the above-mentioned Example 15.

The compounds B-23 to 25, B-28 to 31, and B-38 to 40 shown in the following Table 2 were each synthesized using M-1 and commercially available reagents and by an operation in the same manner as in the above-mentioned Example 16.

The compounds B-26 and B-41 shown in the following Table 2 were each synthesized using M-1 and commercially available reagents and by an operation in the same manner as in the above-mentioned Example 17.

The compounds B-32, B-33, B-35, and B-36 shown in the following Table 2 were each synthesized using M-1 and commercially available reagents and by an operation in the same manner as in the above-mentioned Example 18.

The compounds A-20, A-21, B-46 to 48, B-50, B-53, and B-54 shown in the following Table 2 were each synthesized using M-1 and commercially available reagents and by an operation in the same manner as in the above-mentioned Example 24.

The compound B-51 shown in the following Table 2 was synthesized using M-1 and commercially available reagents and by an operation in the same manner as in the above-mentioned Example 25.

The structural formulas and physical properties of the synthesis intermediate compounds M-1 to M-6 are shown in Table 1.

TABLE 1

| Compound No. | Structure | Analysis data | Example No. |
|---|---|---|---|
| M-1 | 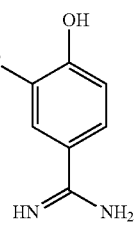 | 1H-NMR (300 MHz, DMSO-d6) δ 11.28 (1H, br s), 9.19 (2H, br s), 9.02 (2H, br s), 7.75 (1H, dd, J = 2.4, 12.0 Hz), 7.59 (1H, m), 7.18 (1H, dd, J = 8.4, 8.7 Hz). MS (ESI) m/z 155 (M + H) + | 1 |

TABLE 1-continued

| Compound No. | Structure | Analysis data | Example No. |
|---|---|---|---|
| M-2 | (structure) | 1H-NMR (300 MHz, DMSO-d6) δ 8.26 (3H, br s), 4.23 (1H, m), 3.72 (3H, s), 3.00 (1H, dd, J = 14.3, 3.5 Hz), 2.92 (1H, dd, J = 14.3, 8.0 Hz). MS (ESI) m/z 184 (M + H) + | 2 |
| M-3 | (structure) | 1H-NMR (400 MHz, DMSO-d6) δ 9.25 (2H, br s), 5.84-5.94 (1H, m), 5.48 (1H, d, J = 17.2 Hz), 5.41 (1H, d, J = 9.6 Hz), 4.11 (1H, br s), 3.65 (1H, br s), 2.83-2.98 (2H, m), 1.45 (9H, s), 1.44 (9H, s). MS (ESI) m/z 286 (M + H) + | 3 |
| M-4 | (structure) | 1H-NMR (400 MHz, CDCl3) δ 5.84 (1H, ddt, J = 17.1, 10.2, 6.0 Hz), 5.21-5.13 (1H, m), 5.11-5.04 (1H, m), 3.30-3.22 (1H, m), 3.16-3.04 (2H, m), 2.34 (2H, ddd, J = 8.3, 6.9, 3.3 Hz), 1.95-1.72 (2H, m), 1.47 (9H, s), 1.44 (9H, s) MS (ESI) m/z 300 (M + H) + | 4 |
| M-5 | (structure) | 1H-NMR (400 MHz, DMSO-d6) δ 5.87 (1H, ddt, J = 17.1, 10.2, 6.1 Hz), 5.19 (1H, ddt, J = 17.1, 3.2, 1.7 Hz), 5.11 (1H, ddt, J = 10.2, 3.2, 1.2 Hz), 3.29 (2H, s), 3.25 (2H, ddd, J = 6.1, 1.7, 1.2 Hz), 1.47 (9H, s). MS (ESI) m/z 172 (M + H) + | 5 |
| M-6 | (structure) | 1H-NMR (400 MHz, CDCl3) δ 7.56 (1H, d, J = 3.8 Hz), 7.03 (1H, d, J = 3.8 Hz), 4.75 (2H, s), 1.57 (9H, s) | 6 |

The structural formulas and physical properties of the compounds A-1 to A-21 and B-1 to B-60 are shown in Table 2.

TABLE 2-1

| Compound No. | Structure | Analysis data | Similar Example |
|---|---|---|---|
| A-1 | (structure) | 1H-NMR (400 MHz, D2O) δ 7.84 (2H, d, J = 8.8 Hz), 7.49 (1H, d, J = 3.6 Hz), 7.44 (2H, d, J = 8.8 Hz), 6.87 (1H, d, J = 3.6 Hz), 4.58 (1H, d, J = 14.3 Hz), 4.52 (1H, d, J = 14.3 Hz), 4.12 (1H, dd, J = 9.6, 6.6 Hz), 3.71-3.76 (1H, m), 3.28-3.35 (1H, m), 2.40-2.50 (1H, m), 1.90-2.14 (3H, m). MS (ESI) m/z 358 (M + H) + | — |

TABLE 2-1-continued

| Compound No. | Structure | Analysis data | Similar Example |
|---|---|---|---|
| A-2 | 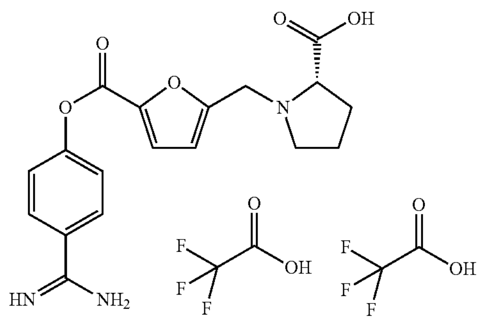 | 1H-NMR (400 MHz, D2O) δ 7.84 (2H, d, J = 8.8 Hz), 7.49 (1H, d, J = 3.6 Hz), 7.44 (2H, d, J = 8.8 Hz), 6.87 (1H, d, J = 3.6 Hz), 4.58 (1H, d, J = 14.3 Hz), 4.52 (1H, d, J = 14.3 Hz), 4.12 (1H, dd, J = 9.6, 6.6 Hz), 3.71-3.76 (1H, m), 3.28-3.35 (1H, m), 2.40-2.50 (1H, m), 1.90-2.14 (3H, m). MS (ESI) m/z 358 (M + H) + | 7 |
| A-3 | 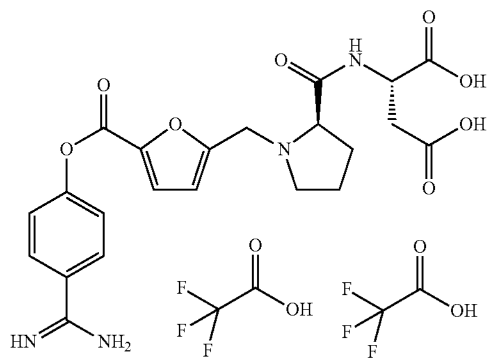 | 1H-NMR (400 MHz, D2O) δ 7.84 (2H, d, J = 8.9 Hz), 7.46 (1H, d, J = 3.6 Hz), 7.44 (2H, d, J = 8.9 Hz), 6.88 (1H, d, J = 3.6 Hz), 4.73 (1H, d, J = 14.3 Hz), 4.53 (1H, d, J = 14.3 Hz), 4.52 (1H, dd, J = 7.5, 4.9 Hz), 4.42 (1H, dd, J = 9.5, 6.8 Hz), 3.79-3.85 (1H, m), 3.36-3.43 (1H, m), 2.86 (1H, dd, J = 16.9, 4.9 Hz), 2.74 (1H, dd, J = 16.9, 7.5 Hz), 2.49-2.56 (1H, m), 2.14-2.22 (1H, m), 1.95-2.06 (2H, m). MS (ESI) m/z 473 (M + H) + | — |
| A-4 | 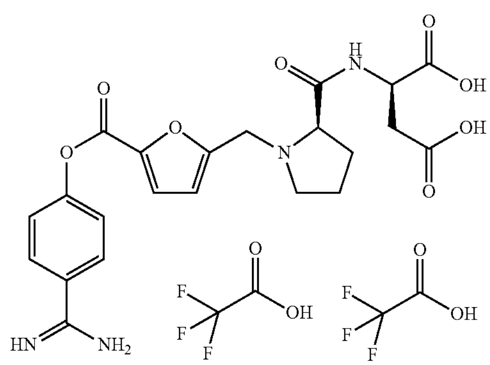 | 1H-NMR (400 MHz, D2O) δ 7.85 (2H, d, J = 8.8 Hz), 7.49 (1H, d, J = 3.6 Hz), 7.45 (2H, d, J = 8.8 Hz), 6.87 (1H, d, J = 3.6 Hz), 4.68 (1H, d, J = 14.6 Hz), 4.51 (1H, d, J = 14.6 Hz), 4.49 (1H, dd, J = 6.4, 5.0 Hz), 4.42 (1H, dd, J = 9.5, 6.9 Hz), 3.81-3.86 (1H, m), 3.36-3.43 (1H, m), 2.79 (1H, dd, J = 17.2, 6.5 Hz), 2.69 (1H, dd, J = 17.2, 5.0 Hz), 2.52-2.62 (1H, m), 1.97-2.22 (3H, m). MS (ESI) m/z 473 (M + H) + | — |
| A-5 | 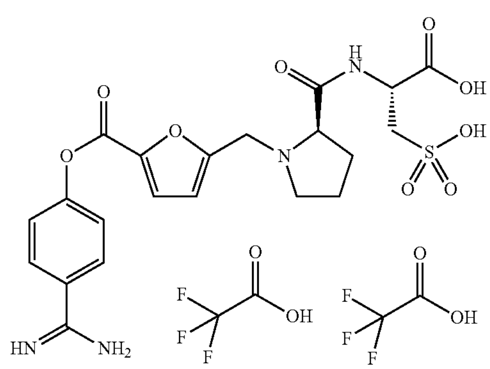 | 1H-NMR (400 MHz, D2O) δ 7.85 (2H, d, J = 8.9 Hz), 7.46 (1H, d, J = 3.7 Hz), 7.45 (2H, d, J = 8.9 Hz), 6.88 (1H, d, J = 3.7 Hz), 4.65 (1H, d, J = 14.4 Hz), 4.63 (1H, dd, J = 8.7, 3.7 Hz), 4.54 (1H, d, J = 14.4 Hz), 4.45 (1H, dd, J = 9.4, 6.9 Hz), 3.78-3.84 (1H, m), 3.35-3.42 (1H, m), 3.36 (1H, dd, J = 14.6, 3.7 Hz), 3.16 (1H, dd, J = 14.6, 8.7 Hz), 2.47-2.55 (1H, m), 1.96-2.20 (3H, m). MS (ESI) m/z 509 (M + H) + | 9 |

TABLE 2-1-continued

| Compound No. | Structure | Analysis data | Similar Example |
|---|---|---|---|
| A-6 | 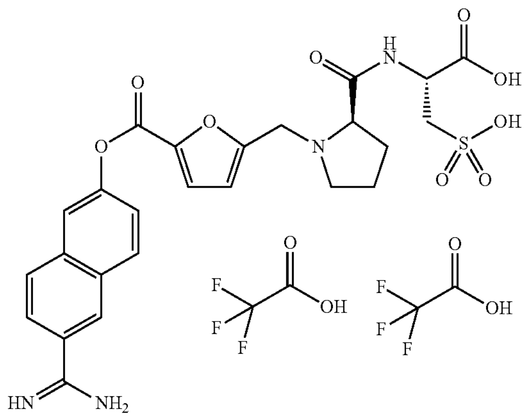 | MS (ESI) m/z 559 (M + H) + | 9 |
| A-7 | 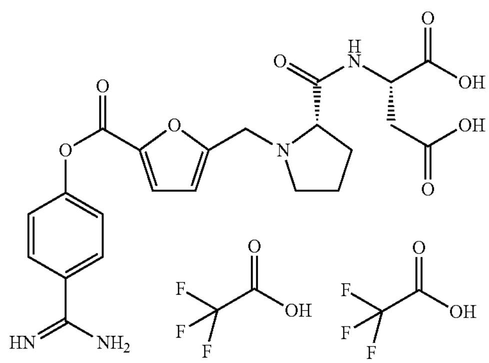 | 1H-NMR (400 MHz, D2O) δ 7.85 (2H, d, J = 8.8 Hz), 7.49 (1H, d, J = 3.6 Hz), 7.45 (2H, d, J = 8.8 Hz), 6.87 (1H, d, J = 3.6 Hz), 4.68 (1H, d, J = 14.6 Hz), 4.51 (1H, d, J = 14.6 Hz), 4.49 (1H, dd, J = 6.4, 5.0 Hz), 4.42 (1H, dd, J = 9.5, 6.9 Hz), 3.81-3.86 (1H, m), 3.36-3.43 (1H, m), 2.79 (1H, dd, J = 17.2, 6.5 Hz), 2.69 (1H, dd, J = 17.2, 5.0 Hz), 2.52-2.62 (1H, m), 1.97-2.22 (3H, m). MS (ESI) m/z 473 (M + H) + | 8 |
| A-8 | 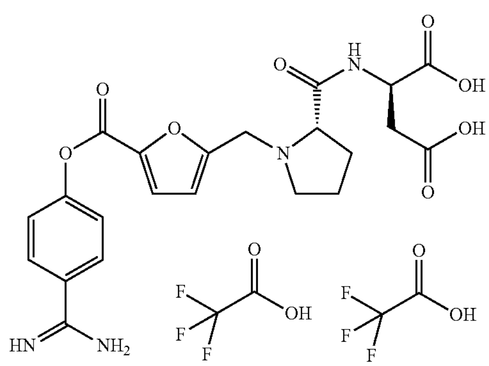 | 1H-NMR (400 MHz, D2O) δ 7.84 (2H, d, J = 8.9 Hz), 7.46 (1H, d, J = 3.6 Hz), 7.44 (2H, d, J = 8.9 Hz), 6.88 (1H, d, J = 3.6 Hz), 4.73 (1H, d, J = 14.3 Hz), 4.53 (1H, d, J = 14.3 Hz), 4.52 (1H, dd, J = 7.5, 4.9 Hz), 4.42 (1H, dd, J = 9.5, 6.8 Hz), 3.79-3.85 (1H, m), 3.36-3.43 (1H, m), 2.86 (1H, dd, J = 16.9, 4.9 Hz), 2.74 (1H, dd, J = 16.9, 7.5 Hz), 2.49-2.56 (1H, m), 2.14-2.22 (1H, m), 1.95-2.06 (2H, m). MS (ESI) m/z 473 (M + H) + | 9 |
| A-9 | 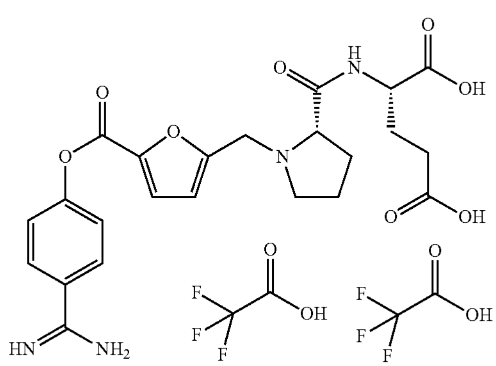 | MS (ESI) m/z 487 (M + H) + | 8 |

TABLE 2-1-continued

| Compound No. | Structure | Analysis data | Similar Example |
|---|---|---|---|
| A-10 | 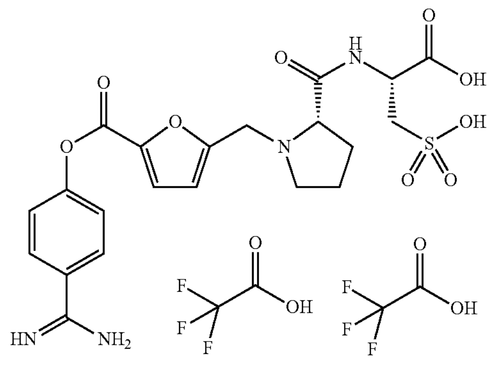 | MS (ESI) m/z 509 (M + H) + | 9 |
| A-11 | 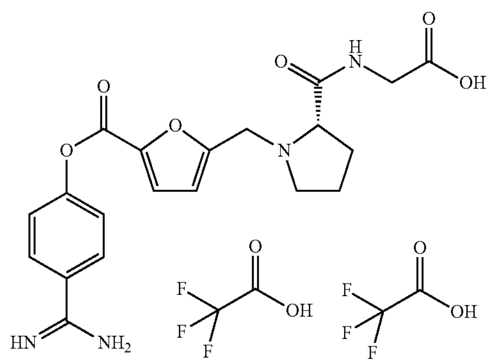 | MS (ESI) m/z 415 (M + H) + | 9 |
| A-12 | 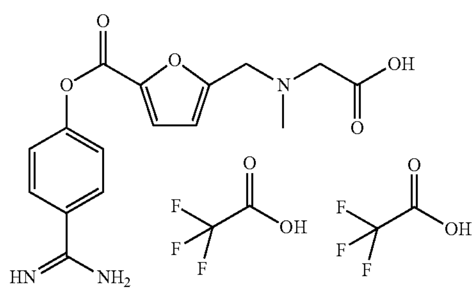 | 1H-NMR (400 MHz, D2O) δ 7.85 (2H, d, J = 8.9 Hz), 7.53 (1H, d, J = 3.6 Hz), 7.44 (2H, d, J = 8.9 Hz), 6.93 (1H, d, J = 3.6 Hz), 4.54 (2H, s), 3.79 (2H, s), 2.93 (3H, s).<br>MS (ESI) m/z 332 (M + H) + | — |
| A-13 | 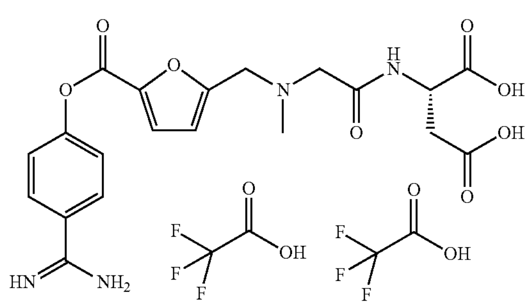 | 1H-NMR (400 MHz, D2O) δ 7.85 (2H, d, J = 8.9 Hz), 7.53 (1H, d, J = 3.6 Hz), 7.44 (1H, d, J = 8.9 Hz), 6.95 (1H, d, J = 3.6 Hz), 4.61 (1H, dd, J = 6.3, 5.6 Hz), 4.57 (2H, s), 4.12 (1H, d, J = 15.9 Hz), 4.06 (1H, d, J = 15.9 Hz), 2.97 (3H, s), 2.85 (1H, dd, J = 17.4, 5.6 Hz), 2.81 (1H, dd, J = 17.4, 6.3 Hz).<br>MS (ESI) m/z 447 (M + H) + | 8 |

TABLE 2-1-continued

| Compound No. | Structure | Analysis data | Similar Example |
|---|---|---|---|
| A-14 | 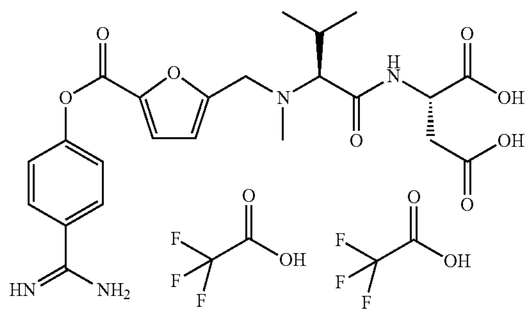 | 1H-NMR (400 MHz, D2O) δ 7.84 (2H, d, J = 8.8 Hz), 7.55 (1H, d, J = 3.6 Hz), 7.44 (2H, d, J = 8.8 Hz), 6.95 (1H, d, J = 3.6 Hz), 4.75 (1H, dd, J = 10.3, 4.6 Hz), 4.57 (1H, d, J = 15.0 Hz), 4.47 (1H, d, J = 15.0 Hz), 3.77 (1H, d, J = 5.3 Hz), 2.99 (1H, dd, J = 17.0, 4.6 Hz), 2.90 (3H, s), 2.86 (1H, dd, J = 17.0, 10.3 Hz), 2.46-2.51 (1H, m), 1.08 (3H, d, J = 6.9 Hz), 0.96 (3H, d, J = 6.7 Hz).<br>MS (ESI) m/z 489 (M + H) + | — |
| A-15 | 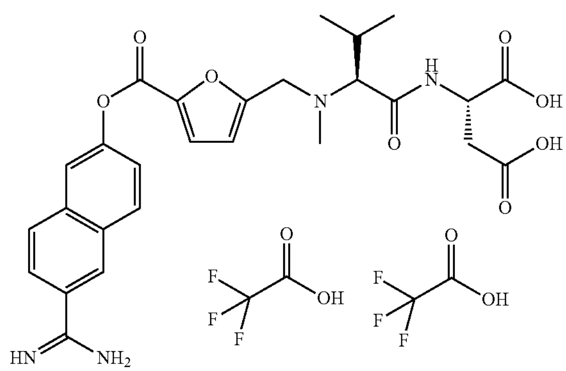 | MS (ESI) m/z 539 (M + H) + | 11 |
| A-16 | 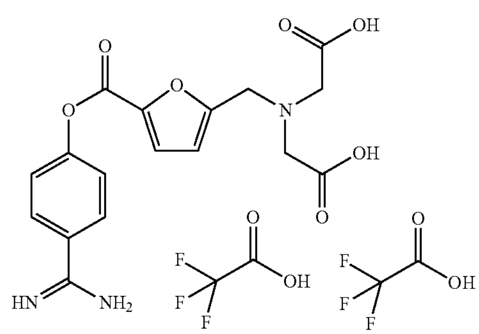 | 1H-NMR (400 MHz, DMSO-d6) δ 9.34 (2H, s), 8.95 (2H, s), 7.90 (2H, d, J = 8.8 Hz), 7.564 (2H, d, J = 8.8 Hz), 7.563 (1H, d, J = 3.5 Hz), 6.66 (1H, d, J = 3.5 Hz), 4.02 (2H, s), 3.49 (4H, s).<br>MS (ESI) m/z 376 (M + H) + | 7 |
| A-17 | 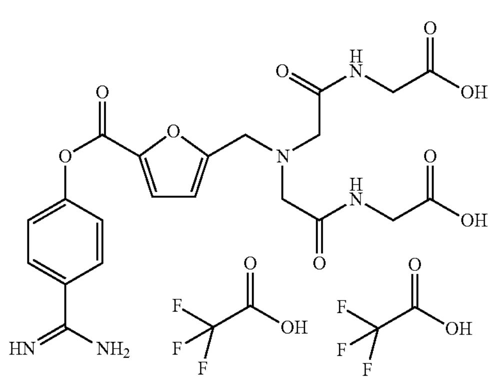 | 1H-NMR (400 MHz, D2O) δ 7.84 (2H, d, J = 8.8 Hz), 7.48 (1H, d, J = 3.6 Hz), 7.43 (2H, d, J = 8.8 Hz), 6.70-6.79 (1H, m), 4.14-4.27 (2H, m), 3.80 (4H, s), 3.65-3.83 (2H, m).<br>MS (ESI) m/z 490 (M + H) + | 8 |

TABLE 2-1-continued

| Compound No. | Structure | Analysis data | Similar Example |
|---|---|---|---|
| A-18 | 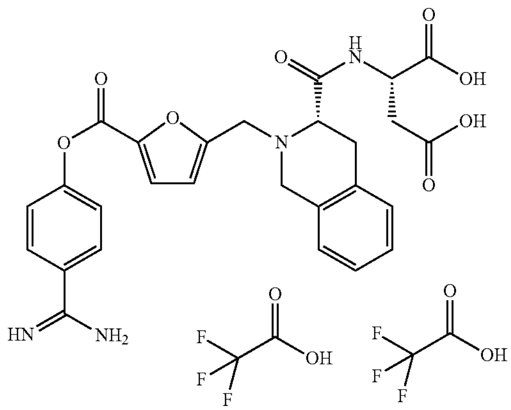 [SMILES: N=C(N)c1ccc(OC(=O)c2ccc(CN3Cc4ccccc4C[C@H]3C(=O)N[C@@H](CC(=O)O)C(=O)O)o2)cc1 ; O=C(O)C(F)(F)F ; O=C(O)C(F)(F)F] | MS (ESI) m/z 535 (M + H) + | — |
| A-19 | 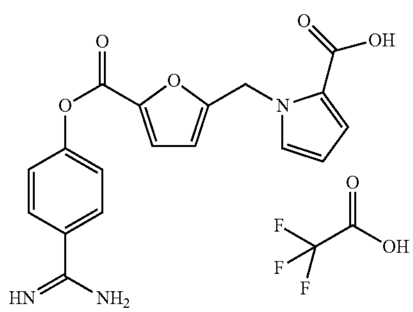 | 1H-NMR (400 MHz, DMSO-d6) δ 9.45-9.24 (2H, br), 9.12-8.93 (2H, br), 7.89 (2H, d, J = 8.8 Hz), 7.55 (2H, d, J = 8.8 Hz), 7.54 (1H, d, J = 3.5 Hz), 7.24 (1H, dd, J = 2.6, 1.8 Hz), 6.87 (1H, dd, J = 3.9, 1.8 Hz), 6.45 (1H, d, J = 3.5 Hz), 6.18 (1H, dd, J = 3.9, 2.6 Hz), 5.70 (2H, s).<br>MS (ESI) m/z 354 (M + H) + | — |
| A-20 | 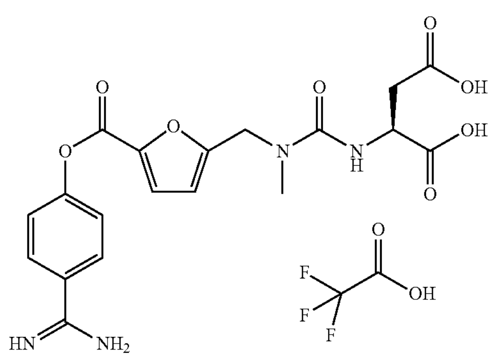 [SMILES: CN(Cc1ccc(C(=O)Oc2ccc(C(=N)N)cc2)o1)C(=O)N[C@@H](CC(=O)O)C(=O)O ; O=C(O)C(F)(F)F] | 1H-NMR (400 MHz, DMSO-d6) δ 9.34 (2H, s), 9.08 (2H, s), 7.96-7.84 (2H, m), 7.62-7.47 (3H, m), 6.77 (1H, d, J = 8.1 Hz), 6.56 (1H, d, J = 3.5 Hz), 4.55 (2H, s), 4.50-4.36 (1H, m), 2.88 (3H, s), 2.74 (1H, dd, J = 16.3, 5.8 Hz), 2.60 (1H, dd, J = 16.3, 7.6 Hz).<br>MS (ESI) m/z 433 (M + H) + | 24 |
| A-21 | 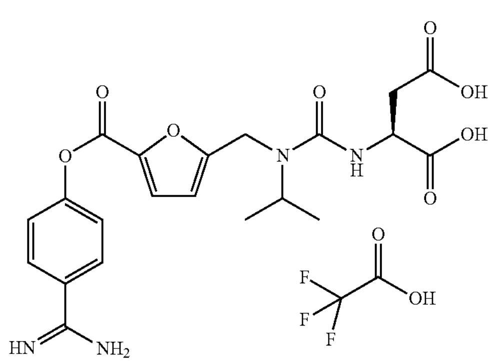 | 1H-NMR (400 MHz, DMSO-d6) δ 9.33 (2H, s), 8.96 (2H, s), 7.89 (2H, d, J = 7.8 Hz), 7.61-7.37 (3H, m), 6.67 (1H, d, J = 8.0 Hz), 6.50 (1H, d, J = 3.6 Hz), 4.46 (2H, s), 4.32-4.12 (1H, m), 3.45 (1H, m), 2.72 (1H, dd, J = 16.3, 5.8 Hz), 2.60 (1H, dd, J = 16.3, 7.4 Hz), 1.09 (6H, t, J = 6.3 Hz).<br>MS (ESI) m/z 461 (M + H) + | 24 |

TABLE 2-1-continued

| Compound No. | Structure | Analysis data | Similar Example |
|---|---|---|---|
| B-1 | 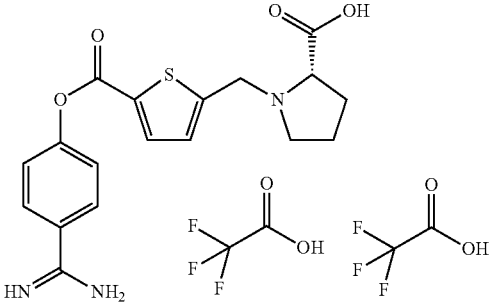 | 1H-NMR (400 MHz, D2O) δ 7.95 (1H, d, J = 3.9 Hz), 7.84 (2H, d, J = 8.9 Hz), 7.44 (2H, d, J = 8.9 Hz), 7.38 (1H, d, J = 3.9 Hz), 4.67 (2H, s), 4.07 (1H, dd, J = 9.6, 6.4 Hz), 3.71-3.77 (1H, m), 3.28-3.35 (1H, m), 2.41-2.50 (1H, m), 1.90-2.16 (3H, m). MS (ESI) m/z 374 (M + H) + | — |
| B-2 | 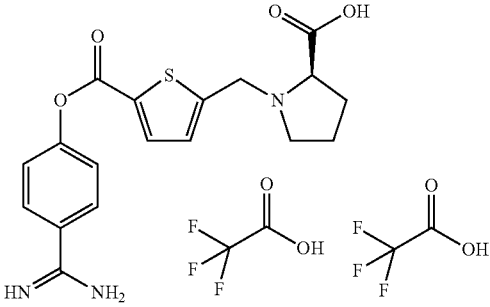 | 1H-NMR (400 MHz, D2O) δ 7.95 (1H, d, J = 3.9 Hz), 7.84 (2H, d, J = 8.9 Hz), 7.44 (2H, d, J = 8.9 Hz), 7.38 (1H, d, J = 3.9 Hz), 4.67 (2H, s), 4.07 (1H, dd, J = 9.6, 6.4 Hz), 3.71-3.77 (1H, m), 3.28-3.35 (1H, m), 2.41-2.50 (1H, m), 1.90-2.16 (3H, m). MS (ESI) m/z 374 (M + H) + | 14 |
| B-3 | 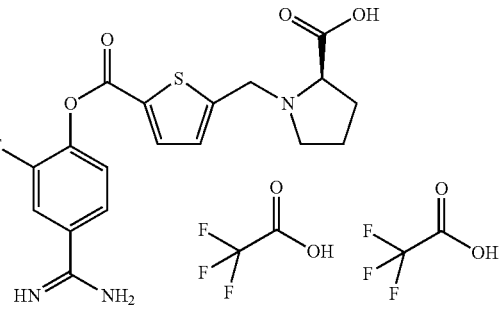 | 1H-NMR (400 MHz, D2O) δ 7.99 (1H, d, J = 3.9 Hz), 7.73 (1H, dd, J = 10.3, 2.1 Hz), 7.65 (1H, ddd, J = 8.4, 2.1, 1.0 Hz), 7.54 (1H, dd, J = 8.4, 7.5 Hz), 4.69 (2H, s), 4.07-4.12 (1H, m), 3.71-3.77 (1H, m), 3.29-3.35 (1H, m), 2.42-2.51 (1H, m), 1.91-2.16 (3H, m). MS (ESI) m/z 392 (M + H) + | 14 |
| B-4 | 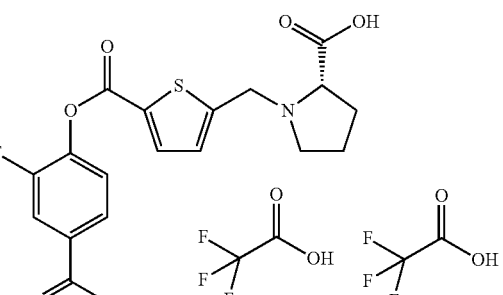 | 1H-NMR (400 MHz, D2O) δ 7.99 (1H, d, J = 3.9 Hz), 7.73 (1H, dd, J = 10.3, 2.1 Hz), 7.65 (1H, ddd, J = 8.4, 2.1, 1.0 Hz), 7.54 (1H, dd, J = 8.4, 7.5 Hz), 4.69 (2H, s), 4.07-4.12 (1H, m), 3.71-3.77 (1H, m), 3.29-3.35 (1H, m), 2.42-2.51 (1H, m), 1.91-2.16 (3H, m). MS (ESI) m/z 392 (M + H) + | 14 |

TABLE 2-1-continued

| Compound No. | Structure | Analysis data | Similar Example |
|---|---|---|---|
| B-5 | 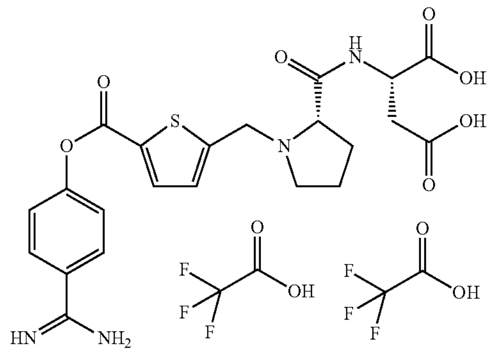 | 1H-NMR (400 MHz, D2O) δ 7.92 (1H, d, J = 3.9 Hz), 7.84 (2H, d, J = 8.8 Hz), 7.46 (2H, d, J = 8.8 Hz), 7.36 (1H, d, J = 3.9 Hz), 4.83 (1H, d, J = 14.0 Hz), 4.62 (1H, d, J = 14.0 Hz), 4.35-4.40 (2H, m), 3.84-3.89 (1H, m), 3.36-3.43 (1H, m), 2.70 (1H, dd, J = 17.2, 6.0 Hz), 2.54-2.61 (1H, m), 2.47 (1H, dd, J = 17.2, 4.8 Hz), 2.15-2.21 (1H, m), 1.99-2.12 (2H, m). MS (ESI) m/z 489 (M + H) + | 8 |
| B-6 | 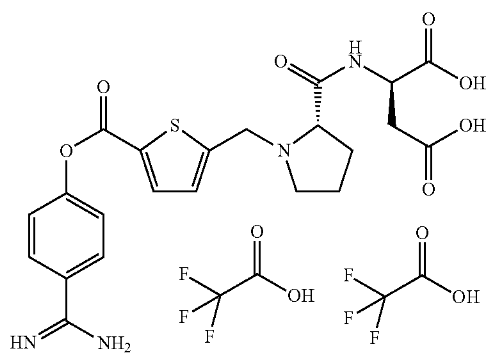 | 1H-NMR (400 MHz, D2O) δ 7.92 (1H, d, J = 3.9 Hz), 7.84 (2H, d, J = 8.9 Hz), 7.46 (2H, d, J = 8.9 Hz), 7.37 (1H, d, J = 3.9 Hz), 4.78 (1H, d, J = 14.1 Hz), 4.66 (1H, d, J = 14.1 Hz), 4.32-4.40 (2H, m), 3.78-3.83 (1H, m), 3.35-3.42 (1H, m), 2.80 (1H, dd, J = 16.5, 4.8 Hz), 2.62 (1H, dd, J = 16.5, 7.8 Hz), 2.47-2.54 (1H, m), 2.14-2.21 (1H, m), 1.94-2.04 (2H, m). MS (ESI) m/z 489 (M + H) + | 9 |
| B-7 | 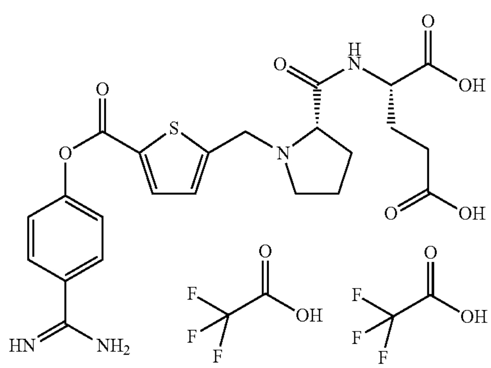 | 1H-NMR (400 MHz, D2O) δ 7.95 (1H, d, J = 3.9 Hz), 7.84 (2H, d, J = 8.8 Hz), 7.45 (2H, d, J = 8.8 Hz), 7.39 (1H, d, J = 3.9 Hz), 4.85 (1H, d, J = 14.0 Hz), 4.61 (1H, d, J = 14.0 Hz), 4.39 (1H, dd, J = 9.6, 6.2 Hz), 4.39 (1H, dd, J = 8.5, 5.0 Hz), 3.85-3.89 (1H, m), 3.36-3.42 (1H, m), 2.53-2.59 (1H, m), 1.97-2.22 (5H, m), 1.84-1.92 (1H, m), 1.67-1.77 (1H, m). MS (ESI) m/z 503 (M + H) + | 8 |
| B-8 | 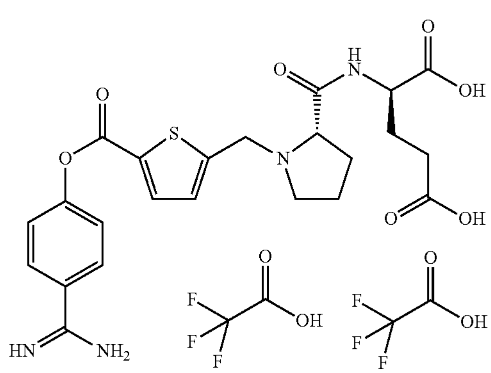 | 1H-NMR (400 MHz, D2O) δ 7.90 (1H, d, J = 3.9 Hz), 7.84 (2H, d, J = 8.8 Hz), 7.46 (2H, d, J = 8.8 Hz), 7.36 (1H, d, J = 3.9 Hz), 4.79 (1H, d, J = 13.9 Hz), 4.64 (1H, d, J = 13.9 Hz), 4.37 (1H, dd, J = 9.3, 7.1 Hz), 4.04 (1H, dd, J = 8.4, 5.1 Hz), 3.79-3.84 (1H, m), 3.39 (1H, ddd, J = 11.4, 8.5, 7.8 Hz), 2.51-2.56 (1H, m), 2.17-2.29 (3H, m), 2.00-2.08 (3H, m), 1.79-1.89 (1H, m). MS (ESI) m/z 503 (M + H) + | 8 |

TABLE 2-1-continued

| Compound No. | Structure | Analysis data | Similar Example |
|---|---|---|---|
| B-9 | 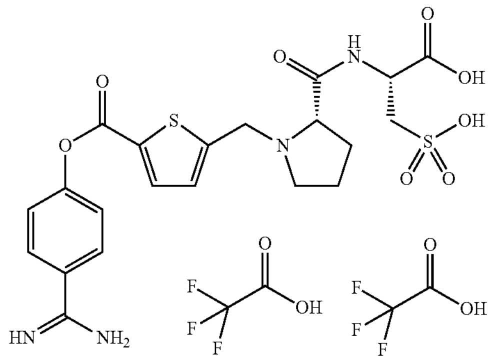 | MS (ESI) m/z 525 (M + H)+ | 9 |
| B-10 | 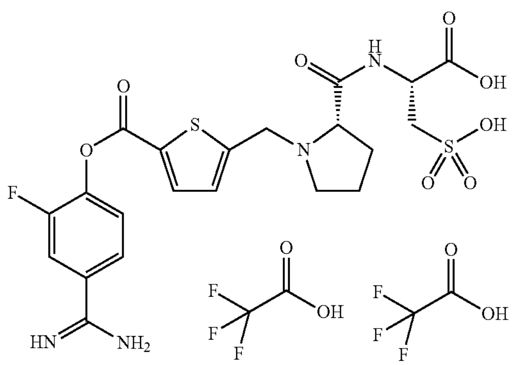 | MS (ESI) m/z 543 (M + H)+ | 9 |
| B-11 | 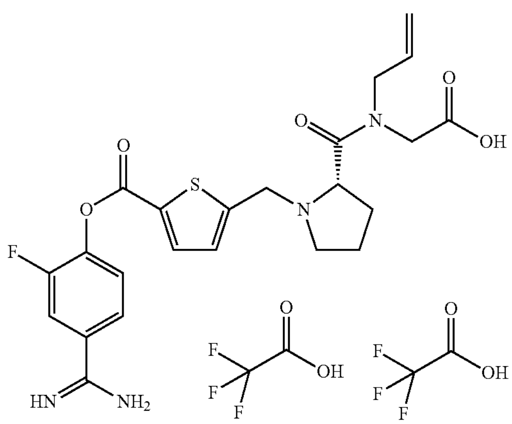 | 1H-NMR (400 MHz, DMSO-d6) δ 9.54-9.38 (2H, br), 9.38-9.05 (2H, br), 8.04 (1H, dd, J = 6.5, 3.9 Hz), 7.95 (1H, d, J = 10.3 Hz), 7.86-7.70 (2H, m), 7.59-7.37 (1H, m), 5.89-5.46 (1H, m), 5.30-4.98 (2H, m), 4.83-4.41 (3H, m), 4.27-3.74 (6H, m), 2.19-1.99 (2H, m), 1.98-1.73 (2H, m).<br>MS (ESI) m/z 489 (M + H)+ | 8 |
| B-12 | 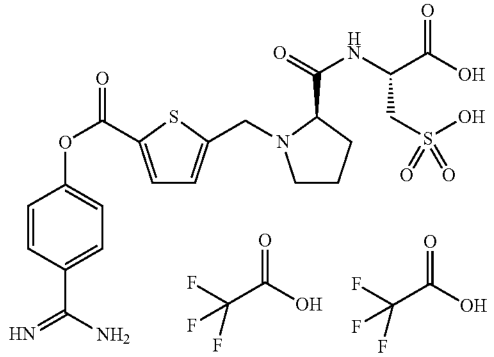 | 1H-NMR (400 MHz, D2O) δ 7.92 (1H, d, J = 3.9 Hz), 7.84 (2H, d, J = 8.8 Hz), 7.46 (2H, d, J = 8.8 Hz), 7.38 (1H, d, J = 3.9 Hz), 4.79 (1H, d, J = 14.0 Hz), 4.66 (1H, d, J = 14.0 Hz), 4.58 (1H, dd, J = 8.8, 3.6 Hz), 4.41 (1H, dd, J = 9.5, 6.9 Hz), 3.78-3.84 (1H, m), 3.35-3.42 (1H, m), 3.34 (1H, dd, J = 14.1, 3.6 Hz), 3.11 (1H, dd, J = 14.1, 8.8 Hz), 2.46-2.54 (1H, m), 1.97-2.21 (3H, m).<br>MS (ESI) m/z 525 (M + H)+ | 9 |

TABLE 2-1-continued

| Compound No. | Structure | Analysis data | Similar Example |
|---|---|---|---|
| B-13 | 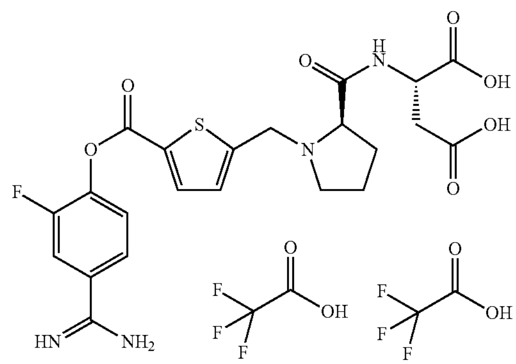 | 1H-NMR (400 MHz, D2O) δ 7.95 (1H, J = 3.9 Hz), 7.73 (1H, dd, J = 10.2, 2.1 Hz), 7.66 (1H, ddd, J = 8.4, 2.1, 0.9 Hz), 7.56 (1H, dd, J = 8.4, 7.5 Hz), 7.39 (1H, d, J = 3.9 Hz), 4.80 (1H, d, J = 14.2 Hz), 4.66 (1H, d, J = 14.2 Hz), 4.44 (1H, dd, J = 7.6, 4.9 Hz), 4.39 (1H, dd, J = 9.5, 6.8 Hz), 3.82 (1H, ddd, J = 11.3, 7.1, 4.5 Hz), 3.39 (1H, ddd, J = 11.3, 8.5, 7.7 Hz), 2.84 (1H, dd, J = 16.9, 4.9 Hz), 2.68 (1H, dd, J = 16.9, 7.6 Hz), 2.48-2.55 (1H, m), 2.15-2.22 (1H, m), 1.94-2.05 (2H, m).<br>MS (ESI) m/z 507 (M + H) + | 8 |
| B-14 | 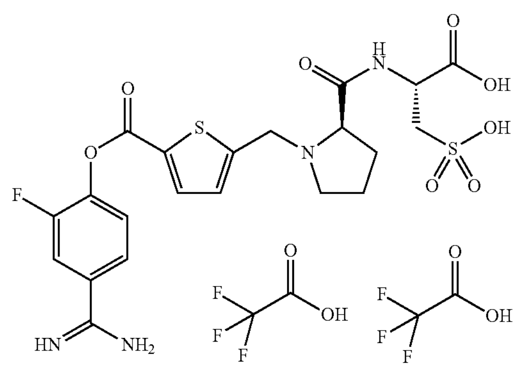 | 1H-NMR (400 MHz, D2O) δ 7.95 (1H, d, J = 3.9 Hz), 7.73 (1H, dd, J = 10.2, 2.1 Hz), 7.66 (1H, ddd, J = 8.5, 2.1, 0.9 Hz), 7.57 (1H, dd, J = 8.5, 7.4 Hz), 7.39 (1H, d, J = 3.9 Hz), 4.79 (1H, d, J = 14.0 Hz), 4.74 (1H, d, J = 14.0 Hz), 4.62 (1H, dd, J = 8.6, 3.6 Hz), 4.41 (1H, dd, J = 9.5, 6.9 Hz), 3.79-3.84 (1H, m), 3.36-3.43 (1H, m), 3.35 (1H, dd, J = 14.6, 3.7 Hz), 3.14 (1H, dd, J = 14.6, 8.6 Hz), 2.47-2.54 (1H, m), 1.97-2.21 (3H, m).<br>MS (ESI) m/z 543 (M + H) + | 9 |
| B-15 | 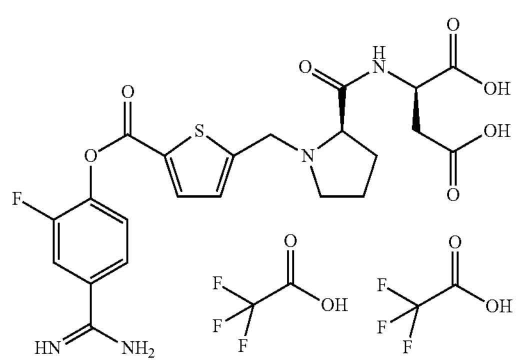 | 1H-NMR (400 MHz, D2O) δ 7.96 (1H, d, J = 3.9 Hz), 7.73 (1H, dd, J = 10.3, 1.7 Hz), 7.66 (1H, dd, J = 8.5, 1.7 Hz), 7.56 (1H, dd, J = 10.3, 8.5 Hz), 7.38 (1H, d, J = 3.9 Hz), 4.84 (1H, d, J = 14.1 Hz), 4.63 (1H, d, J = 14.1 Hz), 4.54-4.43 (1H, m), 4.39 (1H, dd, J = 9.6, 6.4 Hz), 3.93-3.79 (1H, m), 3.49-3.32 (1H, m), 2.87-2.70 (1H, m), 2.65-2.46 (2H, m), 2.27-2.13 (1H, m), 2.13-1.94 (2H, m).<br>MS (ESI) m/z 507 (M + H) + | 9 |
| B-16 | 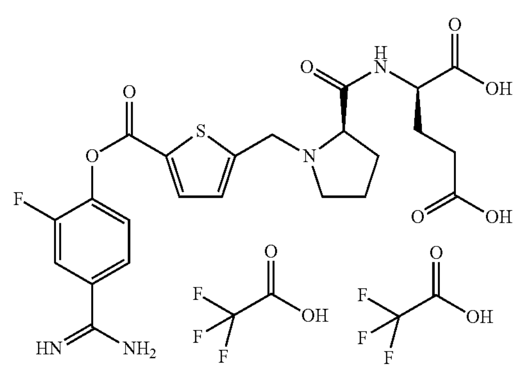 | 1H-NMR (400 MHz, D2O) δ 8.00 (1H, d, J = 3.9 Hz), 7.72 (1H, dd, J = 9.1, 1.5 Hz), 7.66 (1H, dd, J = 8.2, 1.5 Hz), 7.55 (1H, dd, J = 9.1, 8.2 Hz), 7.41 (1H, d, J = 3.9 Hz), 4.87 (1H, d, J = 14.1 Hz), 4.63 (1H, d, J = 14.1 Hz), 4.40 (1H, dd, J = 9.7, 6.2 Hz), 4.21-4.06 (1H, m), 3.94-3.78 (1H, m), 3.50-3.32 (1H, m), 2.66-2.48 (1H, m), 2.31-2.12 (3H, m), 2.12-1.90 (3H, m), 1.87-1.69 (1H, m).<br>MS (ESI) m/z 521 (M + H) + | 8 |

TABLE 2-1-continued

| Compound No. | Structure | Analysis data | Similar Example |
|---|---|---|---|
| B-17 | 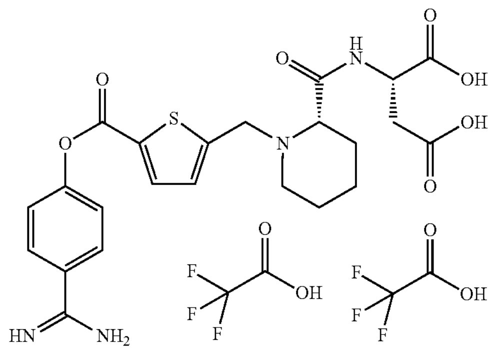 | 1H-NMR (400 MHz, D2O) δ 7.99 (1H, d, J = 3.9 Hz), 7.85 (2H, d, J = 8.8 Hz), 7.45 (2H, d, J = 8.8 Hz), 7.36 (1H, d, J = 3.9 Hz), 4.67 (1H, dd, J = 8.1, 4.5 Hz), 4.59 (1H, d, J = 14.3 Hz), 4.51 (1H, d, J = 14.3 Hz), 3.90 (1H, dd, J = 11.9, 3.4 Hz), 3.62 (1H, br d, J = 11.3 Hz), 3.14 (1H, br dd, J = 12.8, 9.8 Hz), 2.95 (1H, dd, J = 16.8, 4.5 Hz), 2.83 (1H, dd, J = 16.8, 8.1 Hz), 2.22 (1H, br d, J = 13.4 Hz), 1.68-1.92 (4H, m), 1.46-1.51 (1H, m). MS (ESI) m/z 503 (M + H) + | — |
| B-18 | 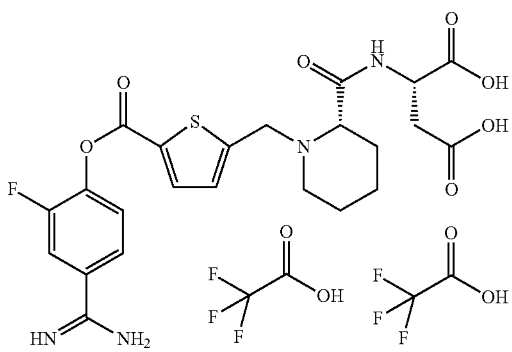 | 1H-NMR (400 MHz, D2O) δ 8.02 (1H, d, J = 3.9 Hz), 7.73 (1H, dd, J = 10.3, 2.2 Hz), 7.66 (1H, ddd, J = 8.5, 2.2, 1.0 Hz), 7.56 (1H, dd, J = 8.5, 7.4 Hz), 7.38 (1H, d, J = 3.9 Hz), 4.64-4.69 (1H, m), 4.60 (1H, d, J = 14.4 Hz), 4.51 (1H, d, J = 14.4 Hz), 3.90 (1H, dd, J = 11.8, 3.0 Hz), 3.61 (1H, br d, J = 12.2 Hz), 3.14 (1H, br dd, J = 12.2, 9.9 Hz), 2.80-2.98 (2H, m), 2.23 (1H, br d, J = 13.2 Hz), 1.68-1.92 (4H, m), 1.45-1.52 (1H, m). MS (ESI) m/z 521 (M + H) + | 15 |
| B-19 | 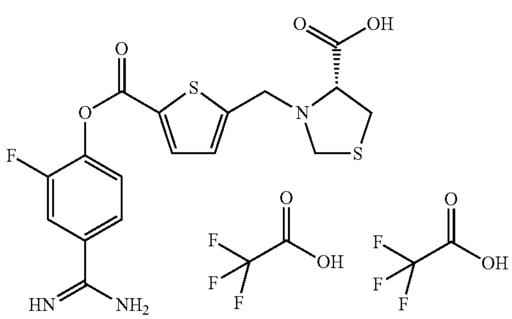 | MS (ESI) m/z 410 (M + H) + | 14 |
| B-20 | 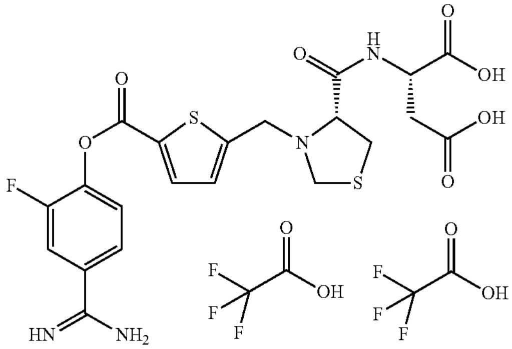 | 1H-NMR (400 MHz, DMSO-d6) δ 9.42 (2H, br), 9.10 (2H, br), 8.15 (1H, d, J = 8.1 Hz), 8.01 (1H, d, J = 3.9 Hz), 7.82-7.71 (2H, m), 7.33 (1H, d, J = 3.9 Hz), 4.60-4.48 (2H, m), 4.24-3.86 (4H, m), 3.14-2.99 (2H, m), 2.82-2.67 (2H, m). MS (ESI) m/z 525 (M + H) + | 8 |

TABLE 2-1-continued

| Compound No. | Structure | Analysis data | Similar Example |
|---|---|---|---|
| B-21 | 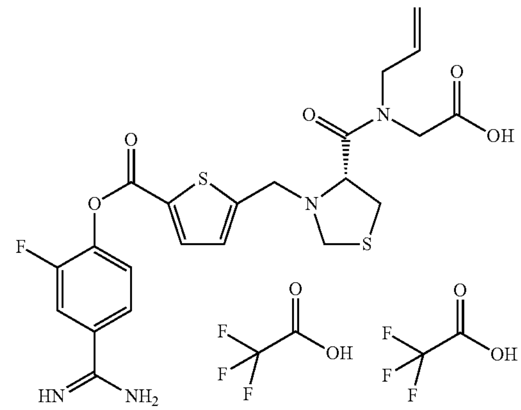 | 1H-NMR (400 MHz, DMSO-d6) δ 9.47-9.36 (2H, br), 9.16-9.03 (2H, br), 7.99 (1H, d, J = 3.8 Hz), 7.94 (1H, dd, J = 10.7, 1.4 Hz), 7.82-7.70 (2H, m), 7.29-7.23 (1H, m), 5.96-5.59 (1H, m), 5.30-5.04 (2H, m), 4.57-4.27 (2H, m), 4.20-3.71 (5H, m), 3.39-3.14 (2H, m), 3.10-2.93 (2H, m). MS (ESI) m/z 507 (M + H) + | 8 |
| B-22 | 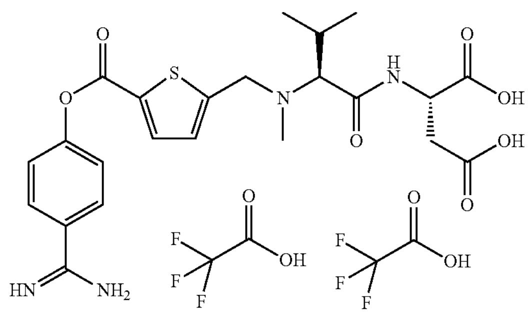 | 1H-NMR (400 MHz, D2O) δ 8.00 (1H, d, J = 3.9 Hz), 7.85 (2H, d, J = 8.8 Hz), 7.45 (2H, d, J = 8.8 Hz), 7.41 (1H, d, J = 3.9 Hz), 4.72-4.79 (1H, m), 4.69 (1H, d, J = 14.6 Hz), 4.60 (1H, d, J = 14.6 Hz), 3.79 (1H, d, J = 5.3 Hz), 3.02 (1H, dd, J = 17.3, 4.4 Hz), 2.90 (3H, s), 2.89 (1H, dd, J = 17.3, 8.3 Hz), 2.45-2.50 (1H, m), 1.10 (3H, d, J = 6.8 Hz), 0.96 (3H, d, J = 6.7 Hz). MS (ESI) m/z 505 (M + H) + | — |
| B-23 | 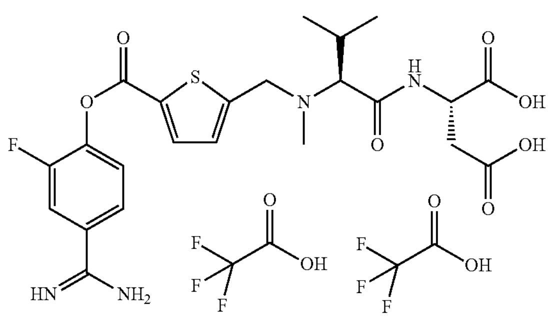 | 1H-NMR (400 MHz, D2O) δ 8.04 (1H, d, J = 3.9 Hz), 7.73 (1H, dd, J = 10.3, 2.2 Hz), 7.66 (1H, ddd, J = 8.5, 2.2, 1.0 Hz), 7.55 (1H, dd, J = 8.5, 7.5 Hz), 7.42 (1H, d, J = 3.9 Hz), 4.75-4.79 (1H, m), 4.70 (1H, d, J = 14.4 Hz), 4.60 (1H, d, J = 14.4 Hz), 3.79 (1H, d, J = 5.3 Hz), 3.02 (1H, dd, J = 17.3, 4.3 Hz), 2.91 (3H, s), 2.90 (1H, dd, J = 17.3, 8.5 Hz), 2.43-2.51 (1H, m), 1.09 (3H, d, J = 6.8 Hz), 0.96 (3H, d, J = 6.7 Hz). MS (ESI) m/z 523 (M + H) + | 16 |
| B-24 | 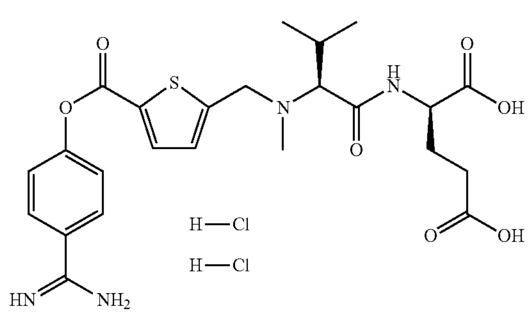 | 1H-NMR (400 MHz, D2O) δ 8.00 (1H, d, J = 3.9 Hz), 7.93-7.73 (2H, m), 7.54-7.36 (3H, m), 4.70 (2H, s), 4.32 (1H, dd, J = 9.1, 5.3 Hz), 3.79 (1H, d, J = 5.6 Hz), 2.93 (3H, s), 2.66-2.39 (3H, m), 2.31-2.05 (1H, m), 2.05-1.83 (1H, m), 1.07 (3H, d, J = 6.8 Hz), 0.96 (3H, d, J = 6.7 Hz). MS (ESI) m/z 519 (M + H) + | 16 |

TABLE 2-1-continued

| Compound No. | Structure | Analysis data | Similar Example |
|---|---|---|---|
| B-25 | 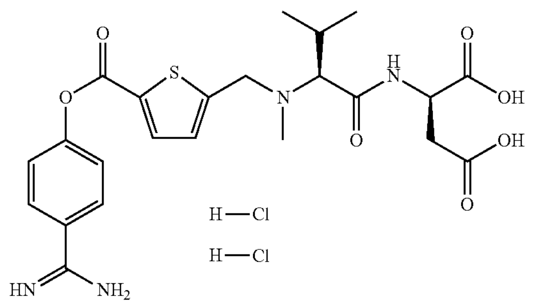 | 1H-NMR (400 MHz, D2O) δ 8.00 (1H, d, J = 3.9 Hz), 7.84 (2H, d, J = 8.8 Hz), 7.48 (1H, d, J = 3.9 Hz), 7.45 (2H, d, J = 8.8 Hz), 4.70 (2H, s), 4.67-4.62 (1H, m), 3.79 (1H, d, J = 5.4 Hz), 3.00-2.91 (1H, m), 2.93 (3H, s), 2.82 (1H, dd, J = 16.9, 8.5 Hz), 2.46 (1H, m), 1.02 (3H, d, J = 6.8 Hz), 0.94 (3H, d, J = 6.7 Hz). MS (ESI) m/z 505 (M + H) + | 16 |
| B-26 | 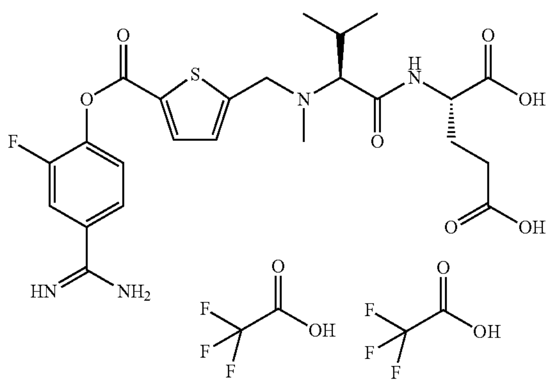 | 1H-NMR (400 MHz, D2O) δ 8.04 (1H, d, J = 3.9 Hz), 7.73 (1H, dd, J = 10.2, 2.1 Hz), 7.69-7.62 (1H, m), 7.59-7.50 (1H, m), 7.43 (1H, d, J = 3.9 Hz), 4.70 (2H, s), 4.49-4.26 (1H, m), 3.80 (1H, d, J = 5.3 Hz), 2.92 (3H, s), 2.54-2.46 (1H, m), 2.46 (2H, t, J = 8.0 Hz), 2.30-2.04 (1H, m), 2.08-1.81 (1H, m), 1.12 (3H, d, J = 6.8 Hz), 0.95 (3H, d, J = 6.7 Hz). MS (ESI) m/z 537 (M + H) + | 17 |
| B-27 | 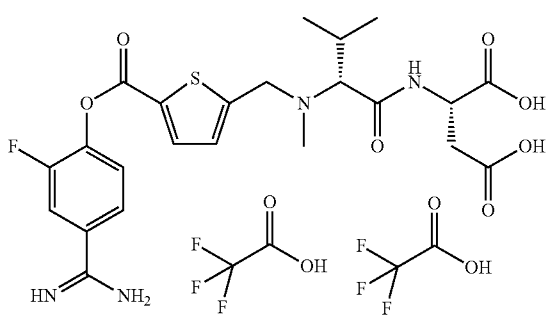 | 1H-NMR (400 MHz, D2O) δ 8.04 (1H, d, J = 4.0 Hz), 7.73 (1H, dd, J = 10.2, 2.1 Hz), 7.69-7.62 (1H, m), 7.60-7.50 (1H, m), 7.49 (1H, d, J = 4.0 Hz), 4.81-4.74 (1H, m), 4.70 (2H, s), 3.80 (1H, d, J = 5.5 Hz), 3.06-2.95 (1H, m), 2.94 (3H, s), 2.87 (1H, dd, J = 17.1, 8.4 Hz), 2.51-2.40 (1H, m), 1.02 (3H, d, J = 6.8 Hz), 0.94 (3H, d, J = 6.7 Hz). MS (ESI) m/z 523 (M + H) + | — |
| B-28 | 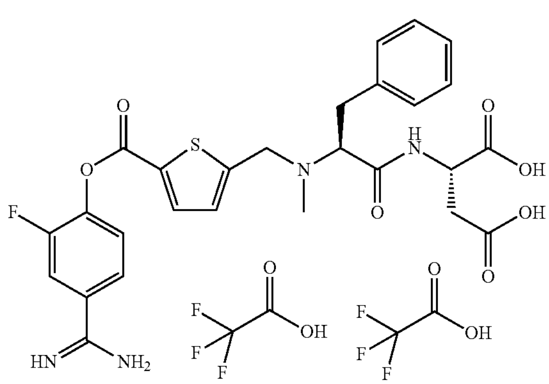 | 1H-NMR (400 MHz, D2O) δ 8.05 (1H, d, J = 3.9 Hz), 7.73 (1H, dd, J = 10.3, 2.1 Hz), 7.69-7.61 (1H, m), 7.62-7.50 (1H, m), 7.45 (1H, d, J = 3.9 Hz), 7.38-7.24 (3H, m), 7.23-7.13 (2H, m), 4.70 (2H, s), 4.33 (1H, dd, J = 8.1, 4.9 Hz), 4.16 (1H, dd, J = 10.8, 5.3 Hz), 3.50 (1H, dd, J = 13.1, 5.3 Hz), 3.21-3.03 (1H, m), 2.98 (3H, s), 2.83 (1H, dd, J = 17.1, 4.9 Hz), 2.49 (1H, dd, J = 17.1, 8.1 Hz). MS (ESI) m/z 571 (M + H) + | 16 |

TABLE 2-1-continued
| Compound No. | Structure | Analysis data | Similar Example |
|---|---|---|---|
| B-29 | 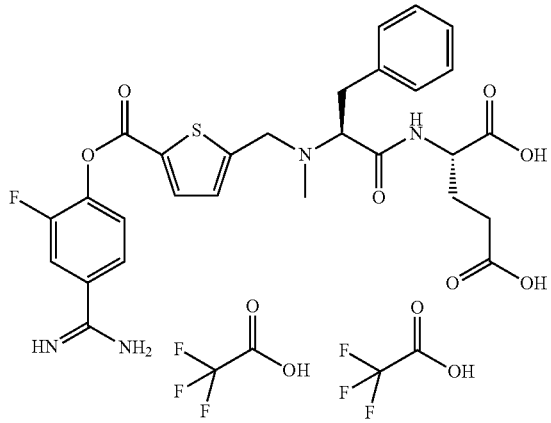 | 1H-NMR (400 MHz, D2O) δ 8.05 (1H, d, J = 3.9 Hz), 7.73 (1H, dd, J = 10.2, 2.1 Hz), 7.69-7.62 (1H, m), 7.61-7.50 (1H, m), 7.45 (1H, d, J = 3.9 Hz), 7.37-7.25 (3H, m), 7.24-7.14 (2H, m), 4.73-4.66 (2H, m), 4.26-4.12 (1H, m), 3.95 (1H, dd, J = 8.6, 4.9 Hz), 3.50 (1H, dd, J = 12.9, 5.4 Hz), 3.18-3.03 (1H, m), 2.98 (3H, s), 2.17-2.01 (1H, m), 2.03-1.85 (2H, m), 1.82-1.65 (1H, m). MS (ESI) m/z 584 (M + H) + | 16 |
| B-30 | 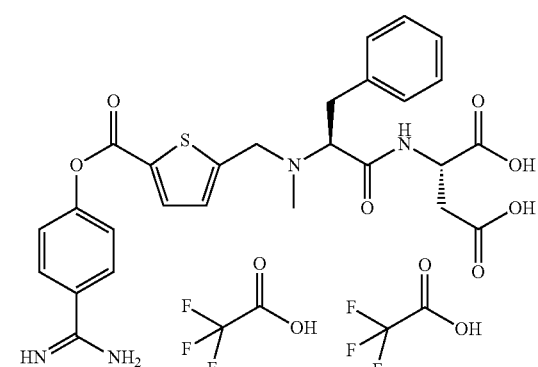 | 1H-NMR (400 MHz, D2O) δ 8.01 (1H, d, J = 3.9 Hz), 7.85 (2H, d, J = 8.7 Hz), 7.53-7.40 (3H, m), 7.35-7.24 (3H, m), 7.19 (2H, d, J = 8.0 Hz), 4.71 (2H, s), 4.36-4.24 (1H, m), 4.22-4.02 (1H, m), 3.61-3.39 (1H, m), 3.23-3.05 (1H, m), 2.97 (3H, s), 2.82 (1H, dd, J = 17.0, 4.9 Hz), 2.48 (1H, dd, J = 17.0, 8.1 Hz). MS (ESI) m/z 553 (M + H) + | 16 |
| B-31 | 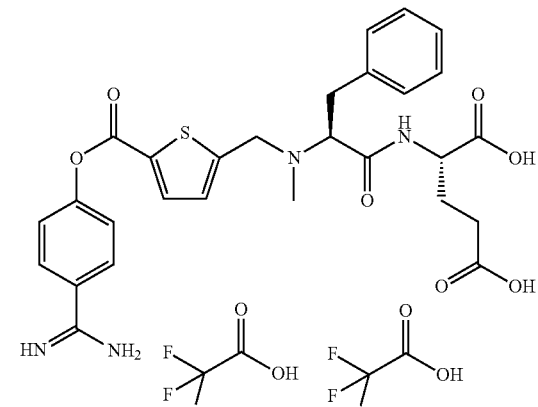 | 1H-NMR (400 MHz, D2O) δ 8.01 (1H, d, J = 3.9 Hz), 7.85 (1H, d, J = 8.9 Hz), 7.52-7.40 (3H, m), 7.36-7.25 (3H, m), 7.25-7.10 (2H, m), 4.70 (2H, s), 4.27-4.12 (1H, m), 3.96 (1H, dd, J = 8.8, 4.8 Hz), 3.51 (2H, dd, J = 13.2, 5.0 Hz), 3.20-3.02 (1H, m), 2.99 (3H, s), 2.13-2.01 (1H, m), 2.02-1.85 (2H, m), 1.74 (1H, d, J = 8.6 Hz). MS (ESI) m/z 567 (M + H) + | 16 |

TABLE 2-1-continued

| Compound No. | Structure | Analysis data | Similar Example |
|---|---|---|---|
| B-32 | 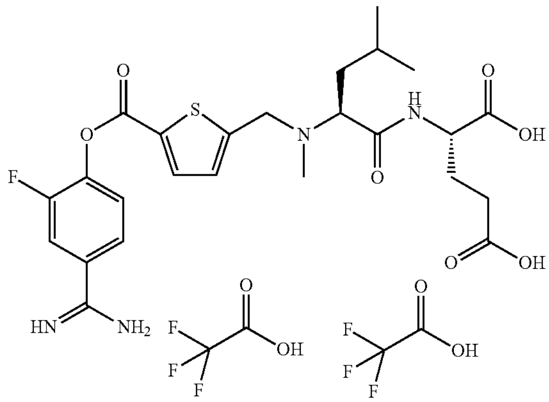 | 1H-NMR (400 MHz, D2O) δ 8.04 (1H, d, J = 3.9 Hz), 7.73 (1H, dd, J = 10.3, 2.1 Hz), 7.69-7.61 (1H, m), 7.60-7.48 (1H, m), 7.43 (1H, d, J = 4.0 Hz), 4.70 (2H, s), 4.31 (1H, dd, J = 8.5, 5.6 Hz), 4.01-3.82 (1H, m), 2.90 (3H, s), 2.42 (2H, t, J = 7.7 Hz), 2.27-2.08 (1H, m), 2.08-1.75 (3H, m), 1.70-1.46 (1H, m), 0.91 (3H, d, J = 6.6 Hz), 0.90 (3H, d, J = 6.7 Hz). MS (ESI) m/z 551 (M + H) + | 18 |
| B-33 | 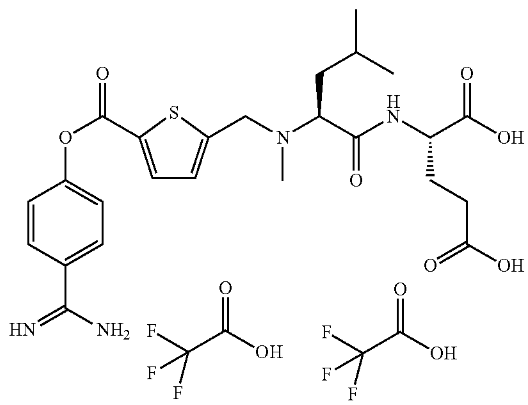 | 1H-NMR (400 MHz, D2O) δ 8.00 (1H, d, J = 3.9 Hz), 7.84 (2H, d, J = 8.9 Hz), 7.45 (2H, d, J = 8.9 Hz), 7.41(1H, d, J = 3.9 Hz), 4.70 (2H, s), 4.36-4.16 (1H, m), 3.94 (1H, dd, J = 10.6, 4.4 Hz), 2.89 (3H, s), 2.40 (2H, t, J = 7.2 Hz), 2.11 (1H, s), 2.05-1.72 (3H, m), 1.72-1.44 (1H, m), 0.91 (3H, d, J = 6.7 Hz), 0.90 (3H, d, J = 6.8 Hz). MS (ESI) m/z 533 (M + H) + | 18 |
| B-34 | 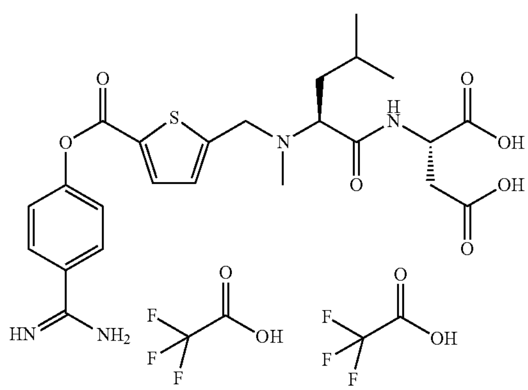 | 1H-NMR (400 MHz, D2O) δ 8.00 (1H, d, J = 3.9 Hz), 7.84 (2H, d, J = 8.9 Hz), 7.45 (2H, d, J = 8.9 Hz), 7.41 (1H, d, J = 3.9 Hz), 4.71 (2H, s), 4.65-4.59 (1H, m), 3.92 (1H, dd, J = 10.9, 4.4 Hz), 2.97 (1H, dd, J = 16.9, 4.5 Hz), 2.88 (3H, s), 2.83 (1H, dd, J = 16.9, 8.8 Hz), 2.03-1.74 (2H, m), 1.62 (1H, s), 0.90 (6H, d, J = 6.5 Hz). MS (ESI) m/z 519 (M + H) + | — |
| B-35 | 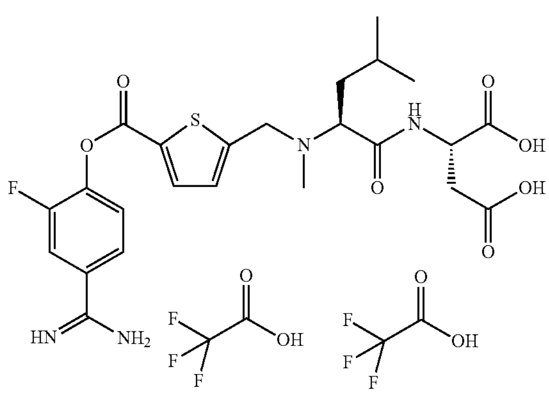 | 1H-NMR (400 MHz, D2O) δ 8.03 (1H, d, J = 4.0 Hz), 7.73 (1H, dd, J = 10.3, 2.1 Hz), 7.69-7.60 (1H, m), 7.60-7.48 (1H, m), 7.42 (1H, d, J = 4.0 Hz), 4.70 (2H, s), 4.67-4.63 (1H, m), 3.93 (1H, dd, J = 10.9, 4.4 Hz), 3.01 (1H, dd, J = 17.1, 4.6 Hz), 2.93-2.79 (4H, m), 2.01-1.71 (2H, m), 1.70-1.51 (1H, m), 0.90 (6H, d, J = 6.5 Hz). MS (ESI) m/z 537 (M + H) + | 18 |

TABLE 2-1-continued
| Compound No. | Structure | Analysis data | Similar Example |
|---|---|---|---|
| B-36 | 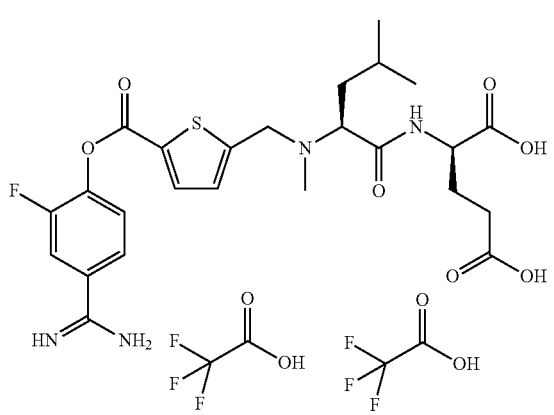 | 1H-NMR (400 MHz, D2O) δ 8.03 (1H, d, J = 4.0 Hz), 7.73 (1H, dd, J = 10.2, 2.1 Hz), 7.68-7.63 (1H, m), 7.58-7.51 (1H, m), 7.45 (1H, d, J = 4.0 Hz), 4.70 (2H, s), 4.37 (1H, dd, J = 9.7, 5.0 Hz), 3.96 (1H, dd, J = 11.1, 4.4 Hz), 2.90 (3H, s), 2.52-2.32 (2H, m), 2.27-2.09 (1H, m), 2.05-1.69 (3H, m), 1.54-1.43 (1H, m), 0.93 (3H, d, J = 3.9 Hz), 0.91 (3H, d, J = 3.9 Hz). MS (ESI) m/z 551 (M + H) + | 18 |
| B-37 | 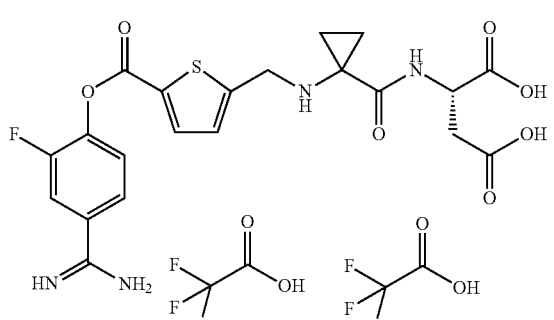 | MS (ESI) m/z 493 (M + H) + | — |
| B-38 | 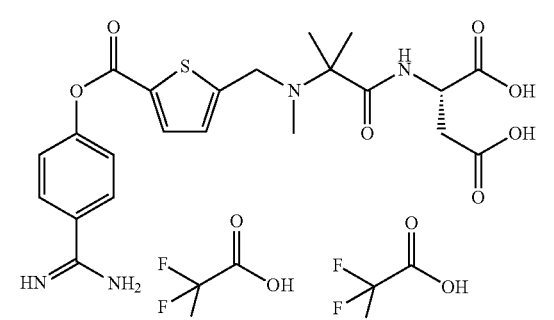 | 1H-NMR (400 MHz, D2O) δ 7.99 (1H, d, J = 3.9 Hz), 7.85 (2H, d, J = 8.9 Hz), 7.46 (2H, d, J = 8.9 Hz), 7.42 (1H, d, J = 3.9 Hz), 4.70 (2H, s), 4.54-4.36 (1H, m), 3.03 (1H, dd, J = 16.8, 5.0 Hz), 2.89 (1H, dd, J = 16.8, 8.5 Hz), 2.83 (3H, s), 1.67 (3H, s), 1.64 (3H, s). MS (ESI) m/z 491 (M + H) + | 16 |
| B-39 | 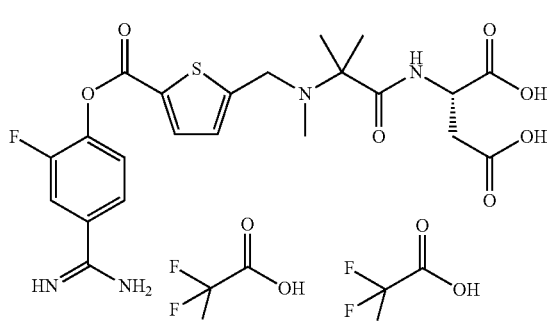 | 1H-NMR (400 MHz, D2O) δ 8.02 (1H, d, J = 3.9 Hz), 7.73 (1H, dd, J = 10.3, 2.1 Hz), 7.69-7.61 (1H, m), 7.60-7.50 (1H, m), 7.43 (1H, d, J = 3.9 Hz), 4.71 (2H, s), 4.52-4.35 (1H, m), 3.02 (1H, dd, J = 16.7, 4.9 Hz), 2.87 (1H, dd, J = 16.7, 8.5 Hz), 2.83 (3H, s), 1.67 (3H, s), 1.63 (3H, s). MS (ESI) m/z 509 (M + H) + | 16 |

TABLE 2-1-continued

| Compound No. | Structure | Analysis data | Similar Example |
|---|---|---|---|
| B-40 | 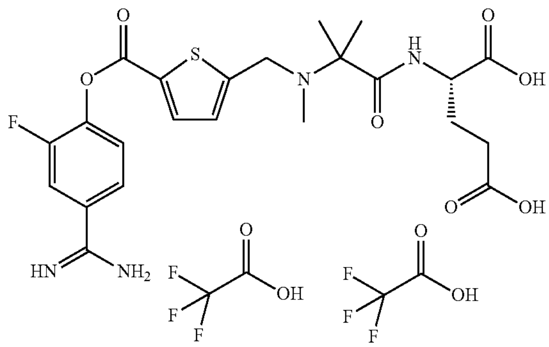 | 1H-NMR (400 MHz, D2O) δ 8.02 (1H, d, J = 3.9 Hz), 7.73 (1H, dd, J = 10.3, 2.1 Hz), 7.68-7.62 (1H, m), 7.61-7.50 (1H, m), 7.43 (1H, d, J = 3.9 Hz), 4.70 (2H, s), 4.50-4.38 (1H, m), 2.83 (3H, s), 2.48 (2H, t, J = 7.0 Hz), 2.35-2.20 (1H, m), 2.17-1.99 (1H, m), 1.66 (6H, s). MS (ESI) m/z 523 (M + H) + | 16 |
| B-41 | 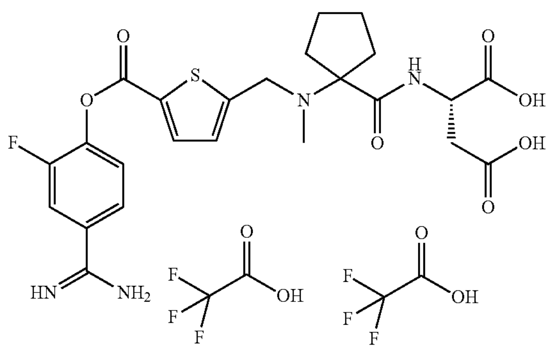 | 1H-NMR (400 MHz, D2O) δ 8.02 (1H, d, J = 3.9 Hz), 7.73 (1H, dd, J = 10.2, 2.1 Hz), 7.69-7.62 (1H, m), 7.58-7.51 (1H, m), 7.41 (1H, d, J = 3.9 Hz), 4.75 (1H, m), 4.51 (1H, d, J = 14.2 Hz), 4.47 (1H, d, J = 14.1 Hz), 3.04 (1H, dd, J = 16.7, 5.0 Hz), 2.90 (1H, dd, J = 16.7, 8.4 Hz), 2.85 (3H, s), 2.43-2.11 (4H, m), 1.99-1.72 (4H, m), 1.00-0.96 (1H, m). MS (ESI) m/z 493 (M + H) + | 17 |
| B-42 | 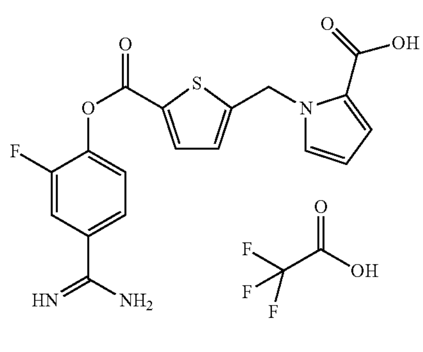 | 1H-NMR (400 MHz, DMSO-d6) δ 9.63-9.07 (4H, br), 7.93 (1H, d, J = 3.6 Hz), 7.87 (1H, dd, J = 13.2, 1.2 Hz), 7.73-7.63 (2H, mm), 7.28-7.20 (2H, m), 6.88-6.78 (1H, m), 6.17-6.11 (1H, m), 5.81 (2H, s). MS (ESI) m/z 388 (M + H) + | — |
| B-43 | 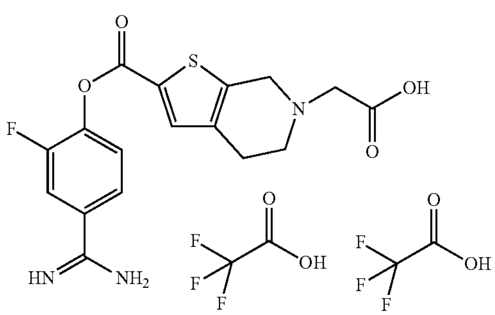 | 1H-NMR (400 MHz, DMSO-d6) δ 9.53-9.33 (2H, br), 9.33-9.12 (2H, br), 8.00-7.88 (2H, m), 7.82-7.70 (2H, m), 4.40 (2H, s), 4.07-3.84 (2H, m), 3.47-3.24 (2H, m), 3.05-2.81 (2H, m). MS (ESI) m/z 378 (M + H) + | — |

TABLE 2-1-continued

| Compound No. | Structure | Analysis data | Similar Example |
|---|---|---|---|
| B-44 | 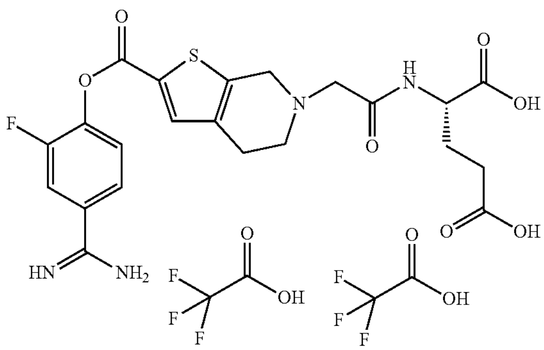 | MS (ESI) m/z 507 (M + H) + | — |
| B-45 | 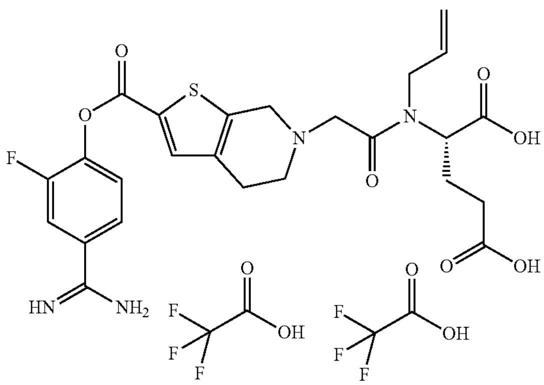 | 1H-NMR (400 MHz, DMSO-d6) δ 9.48-9.35 (2H, br), 9.25-9.08 (2H, br), 8.02-7.84 (1H, m), 7.82-7.69 (1H, m), 7.62 (1H, s), 7.12-7.01 (1H, m), 5.99-5.74 (1H, m), 5.45-5.02 (2H, m), 4.59-4.20 (3H, m), 4.17-3.97 (2H, m), 3.96-3.83 (2H, m), 3.14-2.83 (2H, m), 2.40-2.25 (2H, m), 2.25-2.12 (2H, m), 2.12-1.89 (2H, m). MS (ESI) m/z 547 (M + H) + | — |
| B-46 | 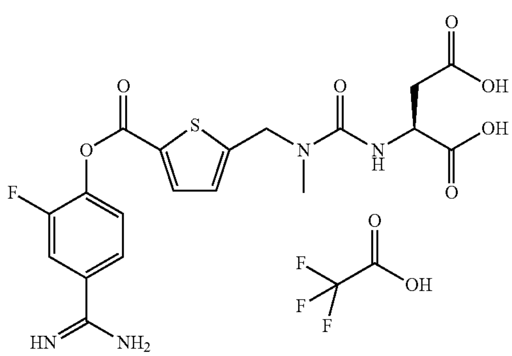 [SMILES: CN(Cc1ccc(C(=O)Oc2ccc(C(=N)N)cc2F)s1)C(=O)N[C@@H](CC(=O)O)C(=O)O ; O=C(O)C(F)(F)F] | 1H-NMR (400 MHz, DMSO-d6) δ 9.41 (2H, s), 9.10 (2H, s), 7.97 (1H, d, J = 3.8 Hz), 7.96-7.90 (1H, m), 7.80-7.70 (2H, m), 7.21 (1H, d, J = 3.9 Hz), 6.79 (1H, d, J = 8.1 Hz), 4.66 (2H, s), 4.56-4.35 (1H, m), 2.86 (3H, s), 2.75 (1H, dd, J = 16.3, 5.9 Hz), 2.60 (1H, dd, J = 16.2, 7.6 Hz). MS (ESI) m/z 467 (M + H) + | 24 |
| B-47 | 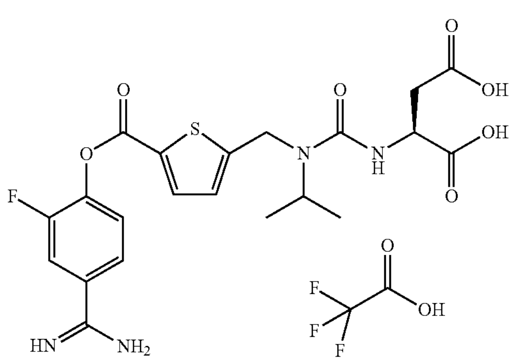 | 1H-NMR (400 MHz, DMSO-d6) δ 9.40 (2H, s), 9.06 (2H, s), 8.02-7.86 (2H, m), 7.88-7.65 (2H, m), 7.21 (1H, d, J = 3.8 Hz), 6.74 (1H, s), 4.60 (2H, s), 4.53-4.34 (1H, m), 4.25-4.01 (1H, m), 2.74 (1H, dd, J = 16.3, 7.4 Hz), 2.61 (1H, dd, J = 16.3, 7.6 Hz), 1.22-1.00 (6H, m). MS (ESI) m/z 495 (M + H) + | 24 |

TABLE 2-1-continued

| Compound No. | Structure | Analysis data | Similar Example |
|---|---|---|---|
| B-48 | 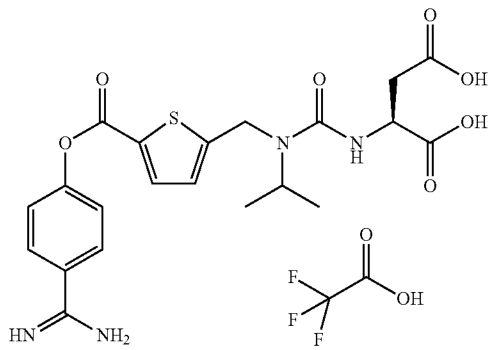 | 1H-NMR (400 MHz, DMSO-d6) δ 9.34 (2H, s), 8.94 (2H, s), 7.97-7.73 (3H, m), 7.56 (2H, d, J = 8.8 Hz), 7.19 (1H, d, J = 3.8 Hz), 6.63 (1H, s), 4.60 (2H, s), 4.47-4.26 (1H, m), 4.26-3.91 (1H, m), 2.75-2.63 (1H, m), 2.63-2.54 (1H, m), 1.11 (6H, t, J = 7.0 Hz). MS (ESI) m/z 477 (M + H) + | 24 |
| B-49 | 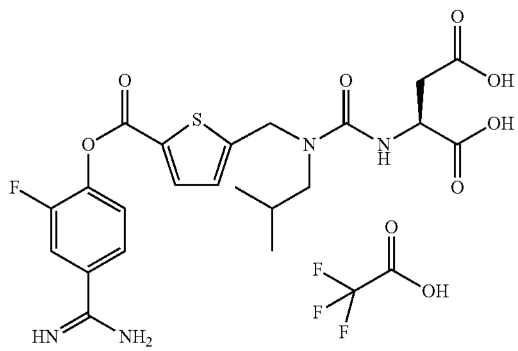 | 1H-NMR (400 MHz, DMSO-d6) δ 9.41 (2H, s), 9.13 (2H, s), 7.96-7.89 (2H, m), 7.80-7.71 (2H, m), 7.22 (1H, d, J = 3.9 Hz), 6.61 (1H, br s), 4.67 (2H, s), 4.53-4.36 (1H, m), 3.11-2.93 (2H, m), 2.78-2.64 (1H, m), 2.58 (1H, dd, J = 16.2, 7.0 Hz), 2.01-1.85 (1H, m), 0.91-0.76 (6H, m). MS (ESI) m/z 509 (M + H) + | — |
| B-50 | 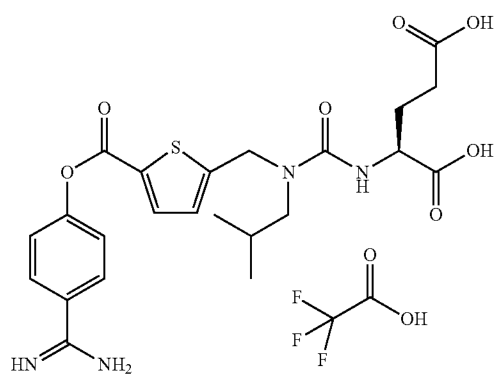 | 1H-NMR (400 MHz, D2O) δ 7.89 (1H, d, J = 3.9 Hz), 7.83 (2H, d, J = 8.9 Hz), 7.41 (2H, d, J = 8.9 Hz), 7.08 (1H, d, J = 3.9 Hz), 4.71 (2H, s), 4.22 (1H, dd, J = 9.7, 4.6 Hz), 3.21 (1H, dd, J = 14.8, 7.7 Hz), 3.08 (1H, dd, J = 14.8, 7.5 Hz), 2.30 (2H, t, J = 7.2 Hz), 2.10 (2H, dd, J = 13.3, 5.8 Hz), 2.00-1.77 (3H, m), 0.85 (3H, d, J = 6.2 Hz), 0.83 (3H, d, J = 6.2 Hz). MS (ESI) m/z 505 (M + H) + | 24 |
| B-51 | 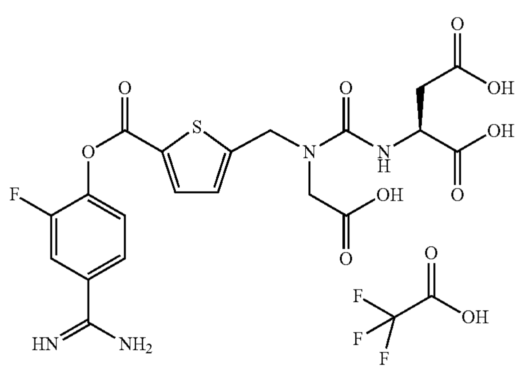 | 1H-NMR (400 MHz, DMSO-d6) δ 9.41 (2H, s), 9.12 (2H, s), 7.99-7.87 (2H, m), 7.80-7.67 (2H, m), 7.24 (1H, d, J = 3.9 Hz), 6.98 (1H, d, J = 7.9 Hz), 4.69 (2H, s), 4.49-4.39 (1H, m), 3.97 (2H, s), 2.71 (1H, dd, J = 16.4, 6.3 Hz), 2.59-2.52 (1H, m). MS (ESI) m/z 511 (M + H) + | 25 |

TABLE 2-1-continued

| Compound No. | Structure | Analysis data | Similar Example |
|---|---|---|---|
| B-52 | 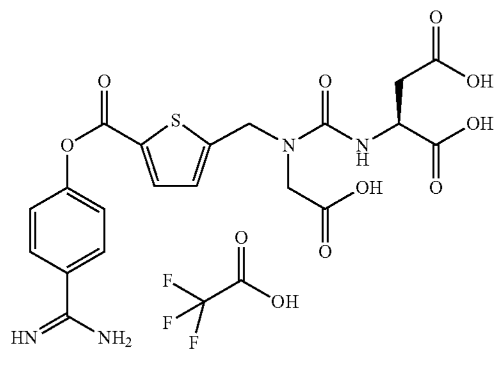 [SMILES: N=C(N)c1ccc(OC(=O)c2ccc(CN(CC(=O)O)C(=O)N[C@@H](CC(=O)O)C(=O)O)s2)cc1 ; O=C(O)C(F)(F)F] | 1H-NMR (400 MHz, DMSO-d6) δ 9.34 (2H, s), 8.96 (2H, s), 8.01-7.74 (3H, m), 7.57 (2H, d, J = 8.8 Hz), 7.22 (1H, d, J = 3.8 Hz), 6.96 (1H, d, J = 7.5 Hz), 4.69 (2H, s), 4.58-4.28 (1H, m), 3.96 (2H, s), 2.87-2.60 (1H, m), 2.62-2.51 (1H, m). MS (ESI) m/z 493 (M + H) + | — |
| B-53 | 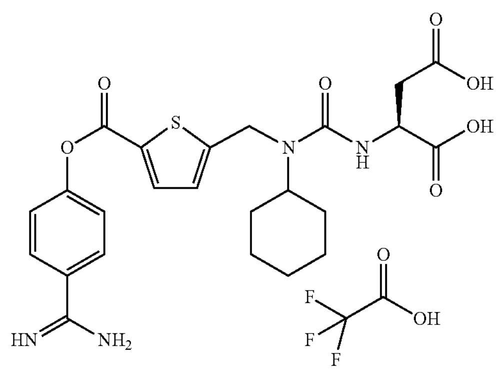 | MS (ESI) m/z 517 (M + H) + | 24 |
| B-54 | 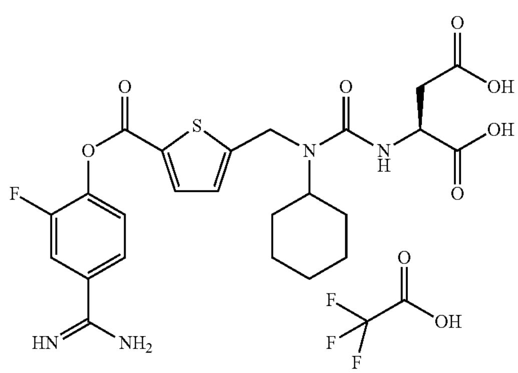 | MS (ESI) m/z 535 (M + H) + | 24 |
| B-55 | 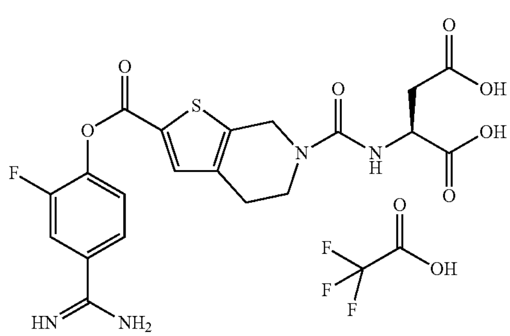 | 1H-NMR (400 MHz, DMSO-d6) δ 9.50-9.24 (2H, br), 9.24-8.99 (2H, br), 7.93-7.78 (2H, m), 7.74-7.62 (2H, m), 6.96 (1H, d, J = 7.5 Hz), 4.62 (2H, s), 4.42-4.31 (1H, m), 3.64-3.54 (2H, m), 2.74-2.62 (2H, m), 2.58-2.45 (2H, m). MS (ESI) m/z 479 (M + H) + | — |

TABLE 2-1-continued

| Compound No. | Structure | Analysis data | Similar Example |
|---|---|---|---|
| B-56 | 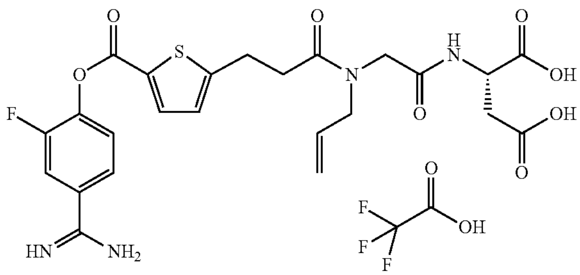 [SMILES: C=CCN(CC(=O)N[C@@H](CC(=O)O)C(=O)O)C(=O)CCc1ccc(C(=O)Oc2ccc(C(=N)N)cc2F)s1 ; O=C(O)C(F)(F)F] | 1H-NMR (400 MHz, DMSO-d6) δ 9.51-9.32 (2H, br), 9.26-9.09 (2H, br), 8.47 (0.5H, d, J = 8.1 Hz), 8.23 (0.5H, d, J = 8.1 Hz), 7.97-7.89 (2H, m), 7.81-7.69 (2H, m), 7.14 (1H, d J = 3.9 Hz), 5.84 (0.5H, ddd, J = 22.4, 10.4, 5.2 Hz), 5.70 (0.5H, ddd, J = 16.1, 10.9, 5.8 Hz), 5.21-5.02 (2H, m), 4.63-4.49 (1H, m), 4.06-3.82 (4H, m), 3.20-3.08 (2H, m), 2.88-2.47 (4H, m). MS (ESI) m/z 549 (M + H) + | — |
| B-57 | 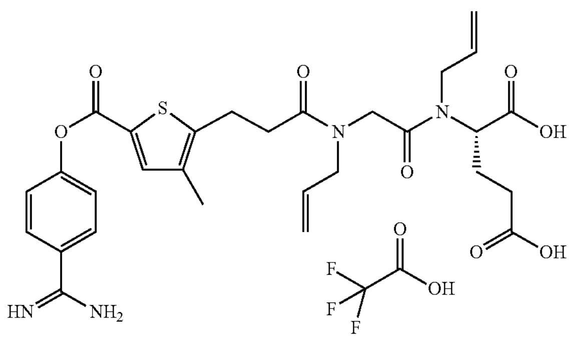 | 1H-NMR (400 MHz, DMSO-d6) δ 9.46-9.22 (2H, br), 9.16-8.91 (2H, br), 7.92-7.86 (2H, m), 7.80-7.76 (1H, m), 7.56-7.49 (1H, m), 5.97-5.61 (2H, m), 5.40-4.97 (4H, m), 4.57-3.77 (7H, m), 3.10-2.97 (2H, m), 2.78-2.65 (1H, m), 2.37-2.19 (4H, m), 2.18-2.04 (1H, m), 2.02-1.84 (1H, m). MS (ESI) m/z 603 (M + H) + | — |
| B-58 | 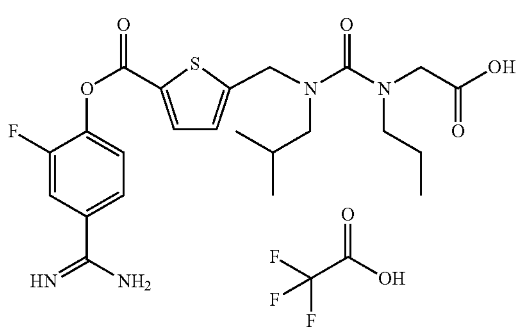 [SMILES: CCCN(CC(=O)O)C(=O)N(Cc1ccc(C(=O)Oc2ccc(C(=N)N)cc2F)s1)CC(C)C ; O=C(O)C(F)(F)F] | 1H NMR (400 MHz, DMSO-d6) δ 9.46 (2H, br s), 9.22 (2H, br s), 8.00-7.95 (2H, m), 7.80-7.75 (2H, m), 7.25 (1H, d, J = 4.0 Hz), 4.55 (2H, s), 3.88 (2H, s), 3.18 (2H, t, J = 6.8 Hz), 2.87 (2H, m), 1.93 (1H, m), 1.65-1.45 (2H, m), 0.88 (3H, t, J = 6.8 Hz), 0.82 (6H, d, J = 6.8 Hz). MS (ESI) m/z 493 (M + H) + | — |
| B-59 | 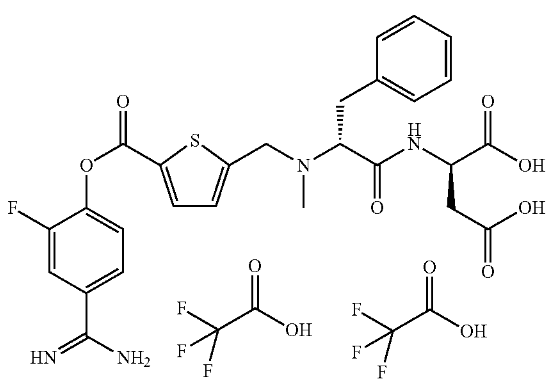 | 1H NMR (400 MHz, D2O) δ 8.06 (1H, d, J = 3.6 Hz), 7.75 (1H, dd, J = 10.4, 2.4 Hz), 7.68 (1H, dd, J = 8.8, 1.6 Hz), 7.56 (1H, t, J = 3.6 Hz), 7.46 (1H, d, J = 4.0 Hz), 7.35-7.25 (3H, m), 7.22-7.15 (2H, m), 4.75 (2H, s), 4.38 (1H, dd, J = 8.0, 3.6 Hz), 4.16 (1H, dd, J = 10.8, 5.2 Hz), 3.51 (1H, dd, J = 12.8, 5.2 Hz), 3.10 (1H, t, J = 12.8 Hz), 2.99 (3H, s), 2.85 (1H, dd, J = 17.2, 4.8 Hz), 2.50 (1H, dd, J = 17.2, 8.0 Hz). MS (ESI) m/z 571 (M + H) + | 16 |

TABLE 2-1-continued

| Compound No. | Structure | Analysis data | Similar Example |
|---|---|---|---|
| B-60 | 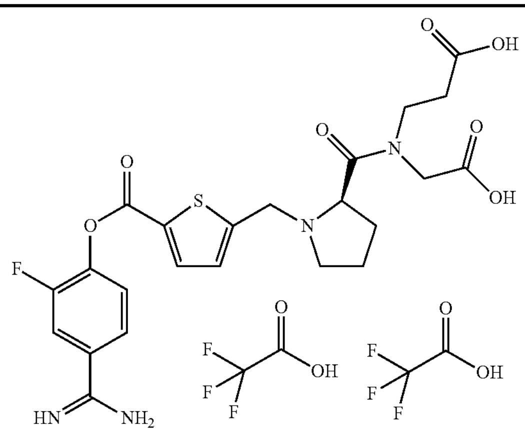 | MS (ESI) m/z 521 (M + H) + | — |

Experimental Example 1

Measurement of Trypsin Inhibitory Activity

Using a 96 well plate (#3915, Costar), a test compound (25 µL) was mixed with 20 µM fluorescence enzyme substrate (Boc-Phe-Ser-Arg-AMC, 50 µL) mixed with 200 mM Tris-HCl buffer (pH 8.0), and human trypsin (Sigma, 25 µL) was added. Using a fluorescence plate reader fmax (Molecular Devices, Inc.), the reaction rate was measured from the time-course changes at excitation wavelength 355 nm and fluorescence wavelength 460 nm. The Ki value was calculated from the concentration of the test compound, reciprocal of reaction rate, and Km value of the enzyme substrate, and by using Dixon plot. The results are shown in Table 3.

Experimental Example 2

Measurement of Enteropeptidase Inhibitory Activity

Using a 96 well plate (#3915, Costar), a test compound (25 µL), 400 mM Tris-HCl buffer (pH 8.0, 25 µL) and 0.5 mg/mL fluorescence enzyme substrate (Gly-Asp-Asp-Asp-Asp-Lys-β-Naphtylamide, 25 µL) were mixed, and recombinant human enteropeptidase (R&D Systems, Inc., 25 µL) was added. Using a fluorescence plate reader fmax (Molecular Devices, Inc.), the reaction rate was measured from the time-course changes at excitation wavelength 320 nm and fluorescence wavelength 405 nm. The Ki value was calculated from the concentration of the test compound, reciprocal of reaction rate, and Km value of the enzyme substrate, and by using Dixon plot. The results are shown in Table 3.

TABLE 3

| compound No. | enteropeptidase inhibitory activity Ki (nM) | trypsin inhibitory activity Ki (nM) |
|---|---|---|
| A-5 | 0.82 | 0.24 |
| A-6 | 0.67 | 0.08 |
| A-10 | 0.65 | 0.97 |
| A-14 | 0.56 | 0.45 |
| A-20 | 0.94 | 0.54 |
| A-21 | 0.38 | 0.84 |
| B-10 | 0.24 | 0.25 |

TABLE 3-continued

| compound No. | enteropeptidase inhibitory activity Ki (nM) | trypsin inhibitory activity Ki (nM) |
|---|---|---|
| B-11 | 0.78 | 0.64 |
| B-12 | 0.95 | 1.14 |
| B-13 | 0.43 | 0.29 |
| B-14 | 0.24 | 0.19 |
| B-15 | 0.69 | 0.52 |
| B-18 | 0.44 | 0.92 |
| B-20 | 0.15 | 0.21 |
| B-21 | 1.00 | 0.38 |
| B-23 | 0.75 | 0.44 |
| B-26 | 1.00 | 0.38 |
| B-27 | 0.78 | 0.68 |
| B-29 | 0.38 | 0.70 |
| B-32 | 0.90 | 0.70 |
| B-35 | 0.53 | 0.81 |
| B-36 | 0.61 | 0.89 |
| B-37 | 1.27 | 1.57 |
| B-41 | 0.97 | 1.56 |
| B-42 | 0.61 | 0.82 |
| B-43 | 0.69 | 0.56 |
| B-45 | 0.62 | 0.71 |
| B-46 | 0.38 | 0.87 |
| B-47 | 0.33 | 0.69 |
| B-55 | 0.20 | 0.24 |
| B-56 | 0.77 | 0.43 |
| B-59 | 0.98 | 3.31 |
| B-60 | 0.53 | 0.42 |

Thus, the compound of the present invention was confirmed to show superior enteropeptidase inhibitory activity and superior trypsin inhibitory activity. Therefore, it has been shown that the compound of the present invention having an inhibitory activity on enteropeptidase and trypsin decreases digestive capacity for protein, lipid, and carbohydrates, and is effective as a therapeutic and prophylactic drug for obesity and hyperlipidemia.

Experimental Example 3

Evaluation of Anti-Diabetes Action

KK-$A^y$/JCL mice (male, 5- to 7-week-old, CLEA Japan, Inc.) known to spontaneously develop obese type 2 diabetes are purchased and, after one week of preliminary rearing period, grouped (6 per group) with the body weight and blood glucose in full feeding as indices. The animals are individually housed in a polycarbonate cage and allowed to drink water freely from a water bottle. During the test period, they are allowed to freely ingest a mixture of powder feed CRF-1 (Oriental Yeast Co., Ltd.) and a test compound (1 to 50 mg/100 g). CRF-1 alone is given to the control group. After one week of dosing period, the blood (6 μL) is drawn from the tail vein of the animals, and the blood glucose level is measured by ACCU-CHEK Aviva (Roche Diagnostics K.K.). A significant difference from the control group is detected by Dunnett's multiple comparison test or Student's t-test (significant level less than 5%). Thus, the test compound can be confirmed to show a significant hypoglycemic action.

The compound of the present invention having an enteropeptidase inhibitory activity and a trypsin inhibitory activity can be confirmed to show a blood glucose elevation suppressive or hypoglycemic action. In addition, it can be confirmed that the compound of the present invention shows an insulin sensitizing activity, and is also useful as a therapeutic or prophylactic agent for obesity, diabetic complications, or metabolic syndrome, since it shows a blood glucose elevation suppressive or hypoglycemic action.

Reference Example 1

Synthesis of reference compound A (N-{3-[5-(4-amidino-2-fluorophenoxycarbonyl)thiophen-2-yl]propanoyl}-L-aspartic acid trifluoroacetate)

Step 1. Synthesis of 5-(2-tert-butoxycarbonylethenyl)thiophene-2-carboxylic acid benzyl ester To a suspension of 60% sodium hydride (1.64 g, 41 mmol) in tetrahydrofuran (50 ml) was added dropwise diethylphosphonoacetic acid tert-butyl ester (12.0 g, 47.6 mmol) at 0° C. After stirring at room temperature for 20 minutes, a solution of 5-formyl-2-thiophenecarboxylic acid benzyl ester (8.75 g, 35.5 mmol) in tetrahydrofuran (10 ml) was added, and the mixture was stirred at room temperature for 1 hour. The reaction mixture was diluted with ethyl acetate, and washed successively with 1N hydrochloric acid and saturated brine. The organic layer was dried over anhydrous magnesium sulfate, and the solvent was evaporated and the residue was purified by column chromatography (10 to 30% ethyl acetate/hexane mixed solvent) to give the title compound (10.6 g).

$^1$H NMR (400 MHz, CDCl$_3$) δ 7.72 (1H, d, J=4.0 Hz), 7.61 (1H, d, J=16.0 Hz), 7.43-7.30 (5H, m), 7.18 (1H, d, J=4.0 Hz), 6.28 (1H, d, J=16.0 Hz), 5.38 (2H, s), 1.52 (9H, s).

Step 2. Synthesis of 5-(2-tert-butoxycarbonylethyl)thiophene-2-carboxylic acid

The compound (0.5 g, 1.45 mmol) obtained in step 1 was dissolved in methanol (5 mL) and chloroform (0.5 mL), palladium hydroxide (0.1 g) was added, and the mixture was dried at room temperature under a hydrogen atmosphere overnight. The reaction mixture was filtered through celite, and the solvent was evaporated under reduced pressure to give the title compound.

$^1$H NMR (300 MHz, DMSO-d$_6$) δ 7.54 (1H, d, J=3.3 Hz), 6.94 (1H, d, J=3.3 Hz), 3.04 (2H, t, J=7.5 Hz), 2.59 (2H, t, J=7.5 Hz), 1.38 (9H, s).

MS (ESI) m/z 257 (M+H)$^+$

Step 3. Synthesis of N-{3-[5-(4-amidino-2-fluorophenoxycarbonyl)thiophen-2-yl]propanoyl}-L-aspartic acid trifluoroacetate The compound (112 mg, 0.44 mmol) obtained in step 2 and 4-amidino-2-fluorophenol trifluoroacetate (118 mg, 0.44 mmol) were suspended in pyridine (3 mL), WSC hydrochloride (169 mg, 0.88 mmol) was added, and the mixture was stirred at room temperature for 2 hours. The reaction mixture was concentrated under reduced pressure, trifluoroacetic acid (3 mL) was added to the obtained residue, and the mixture was stirred at room temperature for 20 minutes. The reaction mixture was concentrated under reduced pressure and the obtained residue was purified by high performance liquid chromatography (water-acetonitrile, each containing 0.1% trifluoroacetic acid), and lyophilized to give a white solid (170 mg). The obtained white solid (50 mg, 0.11 mmol) and L-aspartic acid di-tert-butyl ester hydrochloride (39 mg, 0.12 mmol) were suspended in pyridine (3 mL), WSC hydrochloride (83 mg, 0.43 mmol) was added, and the mixture was stirred at room temperature for 5 hours. The reaction mixture was concentrated under reduced pressure, trifluoroacetic acid (3 mL) was added to the obtained residue, and the mixture was stirred at room temperature for 50 minutes. The reaction mixture was concentrated under reduced pressure and the obtained residue was purified by high performance liquid chromatography (water-acetonitrile, each containing 0.1% trifluoroacetic acid) and lyophilized to give the title compound (73 mg).

$^1$H NMR (400 MHz, DMSO-d$_6$) δ 9.41 (2H, s), 9.11 (2H, s), 8.33 (1H, d, J=8.0 Hz), 7.93 (2H, m), 7.73 (2H, m), 7.12 (1H, d, J=3.6 Hz), 4.55 (1H, m), 3.13 (2H, t, J=7.2 Hz), 2.68 (1H, dd, J=12.4, 6.0 Hz), 2.62-2.55 (3H, m).

MS (ESI) m/z 452 (M+H)$^+$

Reference Example 2

The Ki values of the enteropeptidase inhibitory activity and trypsin inhibitory activity of reference compound A were measured in the same manner as in Experimental Examples 1 and 2, and the results were 1.36 nM and 1.76 nM, respectively. The reference compound was confirmed to have a superior enteropeptidase inhibitory activity and trypsin inhibitory activity.

Experimental Example 4

Evaluation of Antidiabetic Action

KK-A$^y$/JCL mice (male, 5- to 7-week-old, CLEA Japan, Inc.) known to spontaneously develop obese type 2 diabetes were purchased and, after one week of preliminary rearing period, grouped (6 per group) with the body weight and non-fasting blood glucose levels as indices. The animals were individually housed in a polycarbonate cage and allowed to drink water freely from a watering bottle. During the test period, they were allowed to freely ingest a mixture of hydrochloride of reference compound A (5.6 mg/100 g) and powder feed CRF-1 (Oriental Yeast Co., Ltd.). CRF-1 alone was given to the control group. After one week of dosing period, the blood (6 μL) was drawn from the tail vein of the animals, and the blood glucose level was measured by ACCU-CHEK Aviva (Roche Diagnostics K.K.). The results are shown in Table 4. A significant difference from the control group was detected by Dunnett's multiple comparison test or Student's t-test (significance level less than 5%). Thus, reference compound A having a structure similar to that of the compound of the present invention, and further having an enteropeptidase inhibitory activity and trypsin inhibitory activity in the same manner as in the compound of the present invention showed a significant hypoglycemic action. The compound of the present invention having an enteropeptidase inhibitory activity and a trypsin inhibitory activity was shown to have a blood glucose elevation suppressing or hypoglycemic action. In addition, it has also been shown that the compound of the present invention shows an insulin sensitizing activity and is also useful as a therapeutic or prophylactic agent for obesity, diabetic complications or metabolic syndrome, since it shows a blood glucose elevation suppressing or hypoglycemic action.

TABLE 4

|  | dose (mg/100 g) | average value of blood glucose level (mg/dL) | standard error | p value |
| --- | --- | --- | --- | --- |
| control group |  | 478 | 28 |  |
| hydrochloride of reference compound A | 5.6 | 249 | 39 | <0.001 |

INDUSTRIAL APPLICABILITY

The trypsin and enteropeptidase inhibitory compound of the present invention can be used as an active ingredient of a therapeutic or prophylactic agent for obesity or diabetic complications.

This application is based on a patent application No. 2011-127700 filed in Japan, the entire contents of which are incorporated by reference herein.

The invention claimed is:
1. A compound represented by formula (I), or a pharmaceutically acceptable salt thereof:

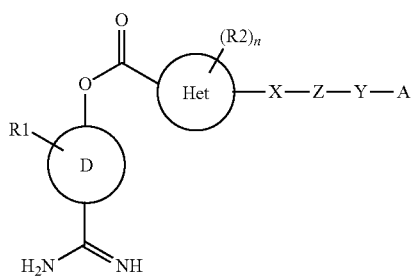

(I)

wherein
D is a benzene ring, a naphthalene ring or a pyridine ring;
Het is a hetero ring represented by formula (III-1)

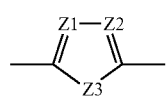

(III-1)

wherein Z1 and Z2 may be the same or different and is each independently CRa and Z3 is an oxygen atom, wherein Ra is independently a hydrogen atom, a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group or a sulfamoyl group;

R1 is a hydrogen atom, a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, or a sulfamoyl group;

n is an integer of 0 to 3;

each R2 is independently a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, or a sulfamoyl group;

X is a lower alkylene group optionally having one or more substituents selected from the group consisting of a halogen atom, a hydroxyl group, an amino group, a lower alkoxyl group, a lower acyl group, and an oxo group, provided when said lower alkylene group has one or more substituents and A is $CO_2R6$, then said one or more substituents is other than an oxo group;

Z is —N(R3)- wherein R3 is a hydrogen atom, a lower alkyl group optionally having substituent(s) selected from the group consisting of a a carboxyl group and —CONH—CH$_2$—CO$_2$H; a lower alkenyl group optionally having substituent(s) selected from the group consisting of a a carboxyl group and —CONH—CH2-CO2H; or a lower cycloalkyl group optionally having substituent(s) selected from the group consisting of a carboxyl group and —CONH—CH2-CO2H;

Y is a single bond or —(CH$_2$)$_p$—C(R4a)(R4b)-(CH$_2$)$_q$— wherein R4a and R4b are each independently a hydrogen atom, a lower alkyl group, or an aralkyl group, p and q are each an integer of 0 to 5, and p+q is an integer of 0 to 5;

A is —CO$_2$R6 wherein R6 is a hydrogen atom, or a group represented by the formula (II)

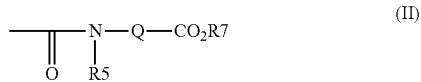

(II)

wherein
R5 is a hydrogen atom, a lower alkyl group optionally having substituent(s) selected from the group consisting of a nitro group, a halogen atom, a cyano group, a hydroxyl group, a thiol group, an amino group, a guanidino group, a formyl group, a phenyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and —CONH—CH$_2$—CO$_2$H, a lower alkenyl group optionally having substituent(s) selected from the group consisting of a nitro group, a halogen atom, a cyano group, a hydroxyl group, a thiol group, an amino group, a guanidino group, a formyl group, a phenyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and —CONH—CH$_2$—CO$_2$H, or a lower alkynyl group optionally having substituent(s) selected from the group consisting of a nitro group, a halogen atom, a cyano group, a hydroxyl group, a thiol group, an amino group, a guanidino group, a formyl group, a phenyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and —CONH—CH$_2$—CO$_2$H;

Q is a lower alkylene group optionally having one or more substituents selected from the group consisting of a nitro group, a halogen atom, a cyano group, a hydroxyl group, a thiol group, an amino group, a guanidino group, a formyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, an arylsulfonylamino group optionally having substituent(s) selected from the group consisting of a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and —CONH—CH$_2$—CO$_2$H, a lower cycloalkyl group optionally having substituent(s) selected from the group consisting of a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and —CONH—CH$_2$—CO$_2$H, an aryl group optionally having substituent(s) selected from the group consisting of a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and —CONH—CH$_2$—CO$_2$H, an aryloxy group optionally having substituent(s) selected from the group consisting of a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and —CONH—CH$_2$—CO$_2$H, an arylthio group optionally having substituent(s) selected from the group consisting of a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and —CONH—CH$_2$—CO$_2$H, an aralkyl group optionally having substituent(s) selected from the group consisting of a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and —CONH—CH$_2$—CO$_2$H, an aralkyloxy group optionally having substituent(s) selected from the group consisting of a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and —CONH—CH$_2$—CO$_2$H, an aralkylthio group optionally having substituent(s) selected from the group consisting of a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and —CONH—CH$_2$—CO$_2$H, a heterocyclic group optionally having substituent(s) selected from the group consisting of a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and —CONH—CH$_2$—CO$_2$H, a heterocyclic oxy group optionally having substituent(s) selected from the group consisting of a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and —CONH—CH$_2$—CO$_2$H, a heterocyclic thio group optionally having substituent(s) selected from the group consisting of a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and —CONH—CH$_2$—CO$_2$H, and an oxo group; and R7 is a hydrogen atom, or R2 and R3 are optionally bonded together to form tetrahydropyridine;

R3 and R4a are optionally bonded together to form a hetero ring selected from the group consisting of pyrrolidine, piperidine, thiazolidine, and tetrahydroisoquinoline;

R3 and R4a and R4b are optionally bonded together to form pyrrole; and

R4a and R4b are optionally bonded together to form lower cycloalkane.

2. A compound or pharmaceutically acceptable salt thereof according to claim 1, wherein D is a benzene ring or a naphthalene ring.

3. A compound or pharmaceutically acceptable salt thereof according to claim 1, wherein D is a benzene ring.

4. A compound or pharmaceutically acceptable salt thereof according to claim 1, wherein R1 is a hydrogen atom or a halogen atom.

5. A compound or pharmaceutically acceptable salt thereof according to claim 1, wherein n is 0, or n is 1 or 2, and R2 is a lower alkyl group.

6. A compound or pharmaceutically acceptable salt thereof according to claim 1, wherein Y is a single bond or —C(R4a)(R4b)-, wherein R4a and R4b are each independently a hydrogen atom, a lower alkyl group, or an aralkyl group.

7. A compound or pharmaceutically acceptable salt thereof according to claim 1, wherein Y is —C(R4a)(R4b)-, R4b is a hydrogen atom, and R3 and R4a are bonded together to form a hetero ring selected from the group consisting of pyrrolidine, piperidine, thiazolidine, and tetrahydroisoquinoline.

8. A compound or pharmaceutically acceptable salt thereof according to claim 1, wherein Y is —C(R4a)(R4b)-, and R3 and R4a and R4b are bonded together to form pyrrole.

9. A compound or pharmaceutically acceptable salt thereof according to claim 1, wherein Y is —C(R4a)(R4b)-, and R4a and R4b are bonded together to form lower cycloalkane.

10. A compound or pharmaceutically acceptable salt thereof according to claim 1, wherein A is —CO$_2$R6, wherein R6 is a hydrogen atom.

11. A compound or pharmaceutically acceptable salt thereof according to claim 1, wherein A is a group represented by formula (II):

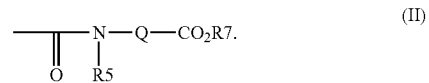

12. A compound or pharmaceutically acceptable salt thereof according to claim 11, wherein X is a lower alkylene group substituted by an oxo group.

13. A compound or pharmaceutically acceptable salt thereof according to claim 1, wherein R5 is a hydrogen atom, a lower alkyl group optionally having substituent(s), or a lower alkenyl group optionally having substituent(s), wherein said substituent(s) is selected from the group consisting of a hydroxyl group, a carboxyl group, a sulfo group, and a phosphono group.

14. A compound or pharmaceutically acceptable salt thereof according to claim 1, wherein Q is a lower alkylene group optionally having one or more substituents selected from the group consisting of a carboxyl group, and a sulfo group.

15. A pharmaceutical composition, comprising a compound or pharmaceutically acceptable salt thereof according to claim 1, as an active ingredient, and at least one pharmaceutically acceptable carrier or excipient.

16. A method of inhibiting serine protease, comprising administering an effective amount of a compound or pharmaceutically acceptable salt thereof according to claim 1 to a subject in need thereof.

17. A method of inhibiting intestinal serine protease, comprising administering an effective amount of a compound or pharmaceutically acceptable salt thereof according to claim 1 to a subject in need thereof.

18. A method of inhibiting trypsin and enteropeptidase, comprising administering an effective amount of a compound or pharmaceutically acceptable salt thereof according to claim 1 to a subject in need thereof.

19. A method of treating hyperglycemia, comprising administering an effective amount of a compound or pharmaceutically acceptable salt thereof according to claim 1 to a subject in need thereof.

20. A method for the treatment of type II diabetes, comprising administering an effective amount of a compound or pharmaceutically acceptable salt thereof according to claim 1 to a subject in need thereof.

21. A compound of any of the formulae described below:
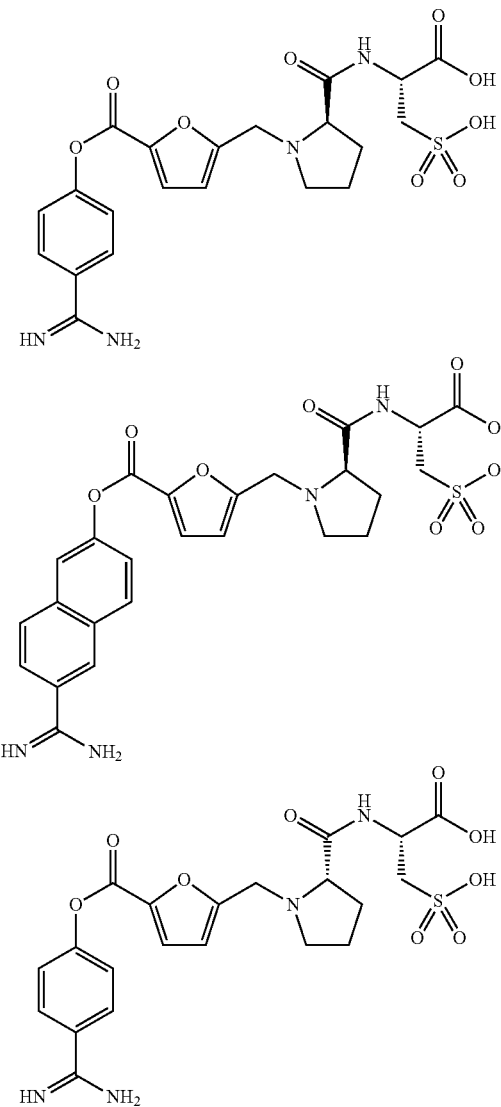
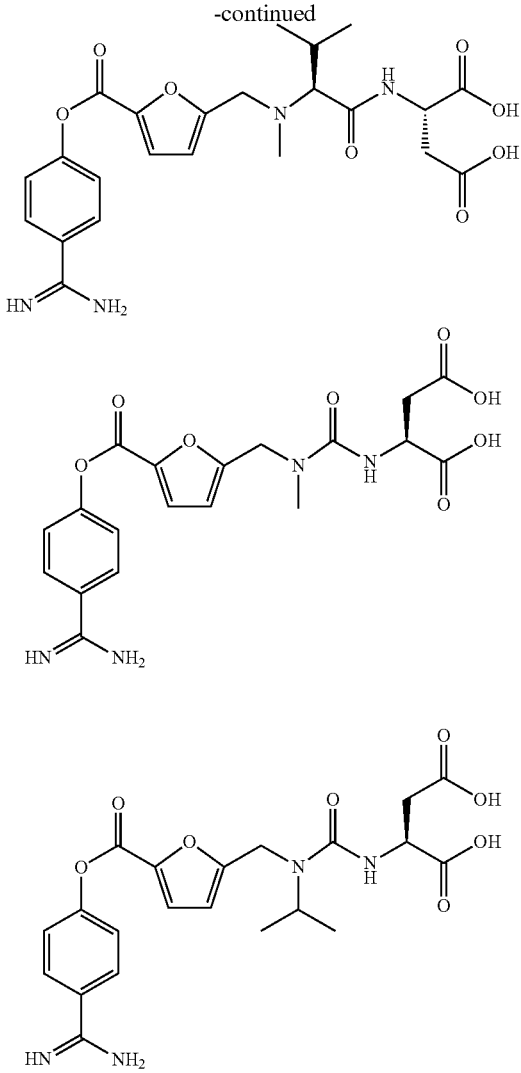
or a pharmaceutically acceptable salt of said compound.
* * * * *